(12) United States Patent
Liautaud et al.

(10) Patent No.: US 9,056,082 B2
(45) Date of Patent: Jun. 16, 2015

(54) MULTIPLEXER FOR A PIEZO CERAMIC IDENTIFICATION DEVICE

(75) Inventors: Christian Liautaud, Boca Raton, FL (US); Rainer M. Schmitt, Palm Beach Gardens, FL (US)

(73) Assignee: SONAVATION, INC., Palm Beach Gardens, FL (US)

( * ) Notice: Subject to any disclaimer, the term of this patent is extended or adjusted under 35 U.S.C. 154(b) by 524 days.

(21) Appl. No.: 12/729,609

(22) Filed: Mar. 23, 2010

(65) Prior Publication Data

US 2010/0237992 A1 Sep. 23, 2010

Related U.S. Application Data

(60) Provisional application No. 61/162,599, filed on Mar. 23, 2009.

(51) Int. Cl.
| | |
|---|---|
| *G06K 9/00* | (2006.01) |
| *H01L 41/00* | (2013.01) |
| *A61K 38/18* | (2006.01) |
| *H01L 27/20* | (2006.01) |

(52) U.S. Cl.
CPC .......... *A61K 38/1808* (2013.01); *G06K 9/0002* (2013.01); *H01L 27/20* (2013.01)

(58) Field of Classification Search
CPC ............ G06K 9/0002; G06K 9/00006; G06K 9/00013; G06K 9/00067; G06K 9/00073; G06K 9/0008; G06K 9/001; H01L 27/20; A61K 38/1808
USPC ...... 310/311, 312, 313 R, 313 A, 313 B, 327; 367/180, 155, 157; 73/35.11, 35.12, 73/35.13; 382/124–127, 312–315
See application file for complete search history.

(56) References Cited

U.S. PATENT DOCUMENTS

| | | | |
|---|---|---|---|
| 7,489,066 B2 | 2/2009 | Scott et al. | |
| 7,795,997 B2 * | 9/2010 | Larson et al. | ................. 333/187 |
| 2005/0189848 A1 | 9/2005 | Byers et al. | |
| 2005/0275309 A1 * | 12/2005 | Oshio | ........................ 310/313 A |
| 2008/0315718 A1 * | 12/2008 | Edmonson et al. | ....... 310/313 B |

OTHER PUBLICATIONS

Search Report and Written Opinion for International Application No. PCT/US10/00845 mailed Jun. 22, 2010, 6 pages.

* cited by examiner

*Primary Examiner* — Brian Le
(74) *Attorney, Agent, or Firm* — Kenneth J. Lukacher Law Group

(57) ABSTRACT

Provided is a Fingerprint sensor using Acoustic Impediography. The sensor includes an Application Specific Integrated Circuit (ASIC or IC) and an array of mechanical resonator used as sensing elements. The array of sensing elements contains multiple sensing elements arranged in rows and columns.

6 Claims, 49 Drawing Sheets

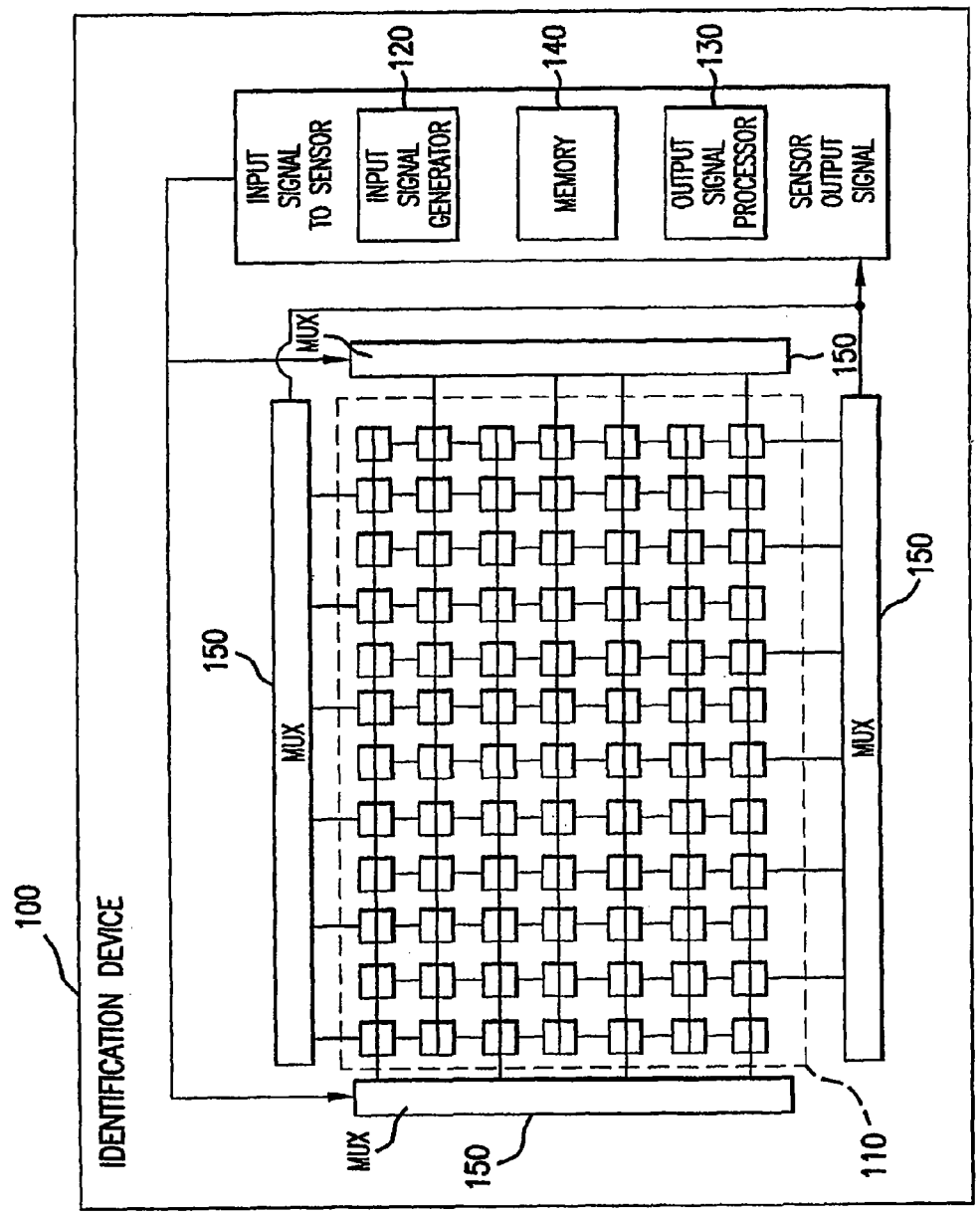

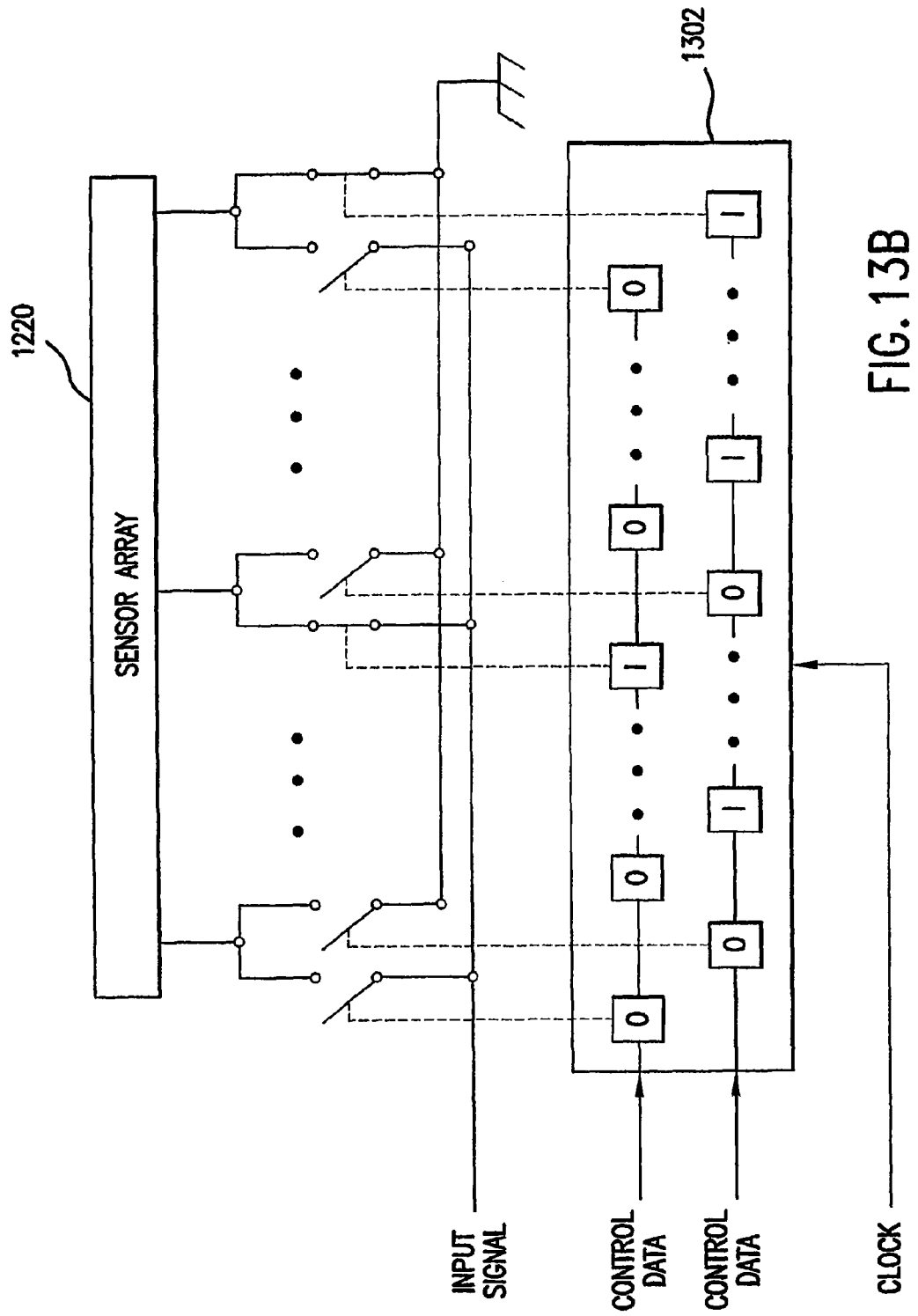

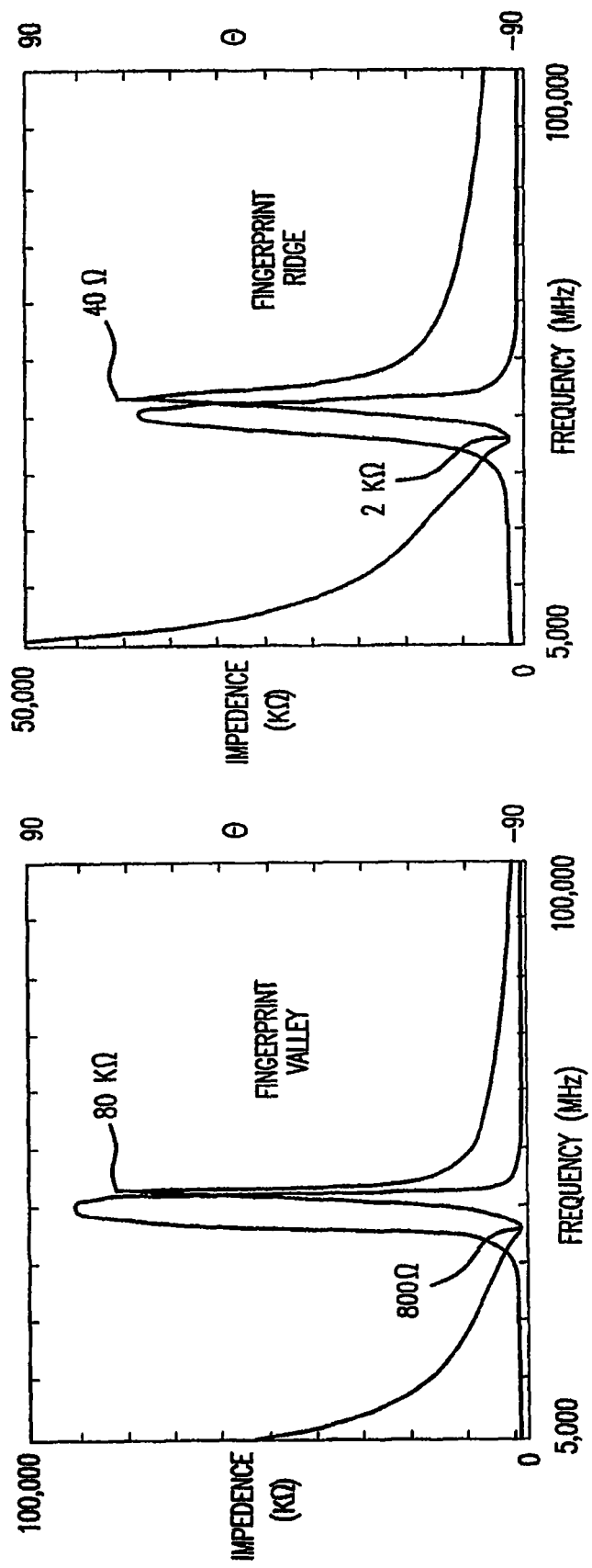

MULTIPLEXER FOR A PIEZO CERAMIC IDENTIFICATION DEVICE

CROSS-REFERENCE TO RELATED APPLICATIONS

This application claims benefit to U.S. Provisional Application No. 61/162,599, filed on Mar. 23, 2009, which is incorporated by reference herein in its entirety.

BACKGROUND OF THE INVENTION

1. Field of the Invention

The present invention relates generally to a piezoelectric identification device and applications thereof. More particularly, it relates to a piezoelectric device for obtaining biometric information, such as a fingerprint, and using the obtained information to recognize and/or identify an individual.

2. Background Art

Biometrics are a group of technologies that provide a high level of security. Fingerprint capture and recognition is an important biometric technology. Law enforcement, banking, voting, and other industries increasingly rely upon fingerprints as a biometric to recognize or verify identity. See, Biometrics Explained, v. 2.0, G. Roethenbaugh, International Computer Society Assn. Carlisle, Pa. 1998, pages 1-34 (incorporated herein by reference in its entirety).

Optical fingerprint scanners are available which detect a reflected optical image of a fingerprint. To capture a quality image at a sufficiently high resolution, optical fingerprint scanners require at minimum optical components (e.g., lenses), an illumination source, and an imaging camera. Such components add to the overall cost of a fingerprint scanner. Mechanical structures to maintain alignment also increase manufacturing and maintenance costs.

Solid-state silicon-based transducers are also available in fingerprint scanners sold commercially. Such silicon transducers measure capacitance. This requires the brittle silicon transducers to be within a few microns of the fingerprint sensing circuit reducing their durability. To detect a rolled fingerprint, the sensing array of the solid-state transducer needs to have an area of 1 inch.times.1 inch and a thickness of about 50 microns. This is a big geometry for silicon that increases the base cost of a fingerprint scanner and leads to greater maintenance costs. Durability and structural integrity are also more likely to suffer in such a large silicon geometry.

What is needed is an inexpensive, durable fingerprint scanner with low maintenance costs. What is also needed is a low cost biometric device that can protect individuals and the general populace against physical danger, fraud, and theft (especially in the realm of electronic commerce).

BRIEF SUMMARY OF THE INVENTION

The present invention provides a Fingerprint sensor using Acoustic Impediography. The sensor includes an Application Specific Integrated Circuit (ASIC or IC) and an array of mechanical resonator used as sensing elements. The array of sensing elements contains multiple sensing elements arranged in rows and columns.

Further features and advantages of the present invention, as well as the structure and operation of various embodiments of the present invention, are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the pertinent art to make and use the invention.

FIG. 1 illustrates a piezoelectric identification device according to an embodiment of the invention.

FIG. 13B illustrates how to control the switches of FIG. 13A according to an embodiment of the invention.

FIG. 19 illustrates the impedance of a piezoelectric element loaded by a fingerprint valley according to an embodiment of the invention.

FIG. 20 illustrates the impedance of a piezoelectric element loaded by a fingerprint ridge according to an embodiment of the invention.

DETAILED DESCRIPTION OF THE INVENTION

Overview of the Invention

Figure 3:
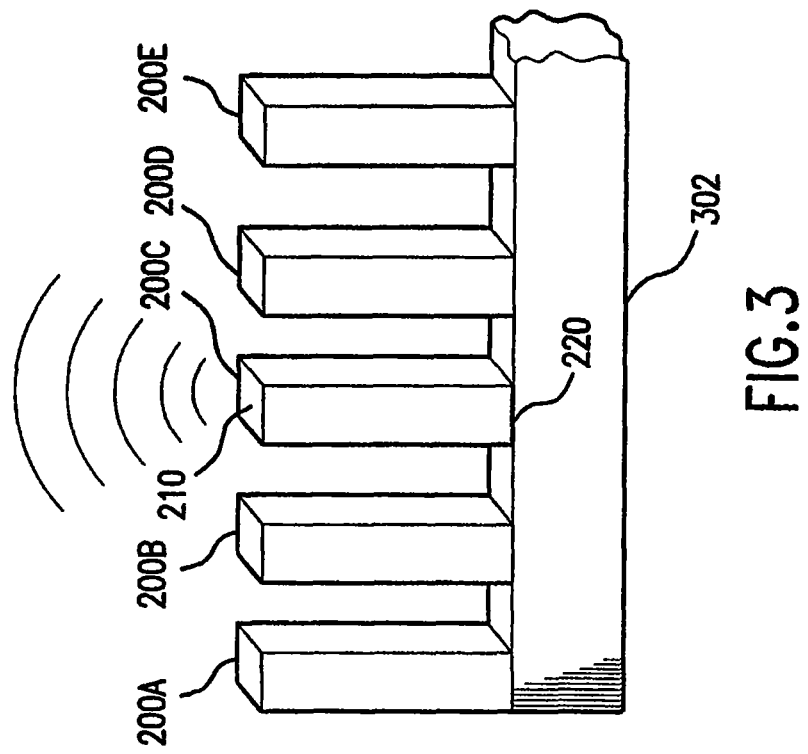
FIG. 3 illustrates a row of piezoelectric elements according to an embodiment of the invention.

The present invention relates generally to a piezoelectric identification device and applications thereof. More particularly, it relates to a piezoelectric device for obtaining biometric data or information, such as a fingerprint, and using the obtained information to recognize and/or verify the identity of an individual.

Example Devises and Systems According to the Invention

FIG. 1 is a schematic diagram of a piezoelectric identification device 110 according to an embodiment of the invention. Identification device 100 has a piezoelectric sensor 100, a sensor input signal generator 120, a sensor output signal processor 130, and a memory 140. The input signal generated by input signal generator 120 is coupled to sensor 110 by two multiplexers 150. The output signal of sensor 110 is similarly coupled to output signal processor 130 by two multiplexers 150.

Piezo Ceramic Sensors

Sensor 110 is preferably an array of piezo ceramic elements. For example, sensor 110 can comprise an array of polycrystalline ceramic elements that are chemically inert and immune to moisture and other atmospheric conditions. Polycrystalline ceramics can be manufactured to have specific desired physical, chemical, and/or piezoelectric characteristics. Sensor 110 is not limited to comprising an array of piezo ceramic elements, however. Sensor 110 can comprise, for example, a piezoelectric film. A polarized fluoropolymer film, such as, polyvinylidene flouride (PVDF) film or its copolymers can be used.

Figure 2:
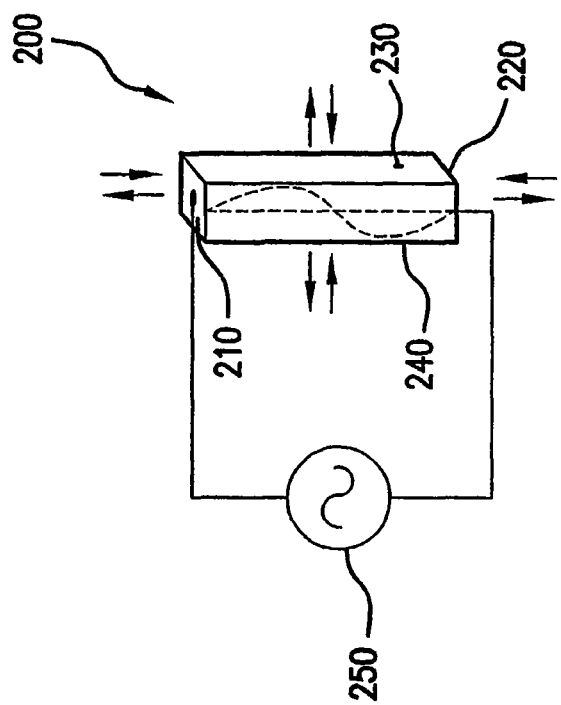
FIG. 2 illustrates a piezoelectric element according to an embodiment of the invention.

FIG. 2 illustrates the operating characteristics of a single rectangular piezo ceramic element 200 having surfaces 210, 220, 230, and 240. When force is applied to surfaces 210 and 220, a voltage proportional to the applied force is developed between surfaces 210 and 220. When this occurs, surfaces 230 and 240 move away from one another. When a voltage is applied to surfaces 210 and 220, surfaces 230 and 240 move towards one another, and surfaces 210 and 220 move away from one another. When an alternating voltage is applied to surfaces 210 and 220, piezo ceramic element 200 oscillates in a manner that would be known to a person skilled in the relevant art.

FIG. 3 illustrates a row of five rectangular piezo ceramic elements 200A, 200B, 200C, 200D, and 200E. Each of these rectangular piezo ceramic elements 200 is attached or integral to support 302. Support 302 inhibits the movement of one surface of each rectangular piezo ceramic elements 200. Thus, when an alternating voltage is applied to surfaces 210 and 220 of piezo ceramic element 200C, a sonic wave is generated at surface 210 of piezo ceramic element 200C. The frequency of the generated sonic wave is dependent on the physical characteristics of piezo ceramic element 200C.

Figure 5:
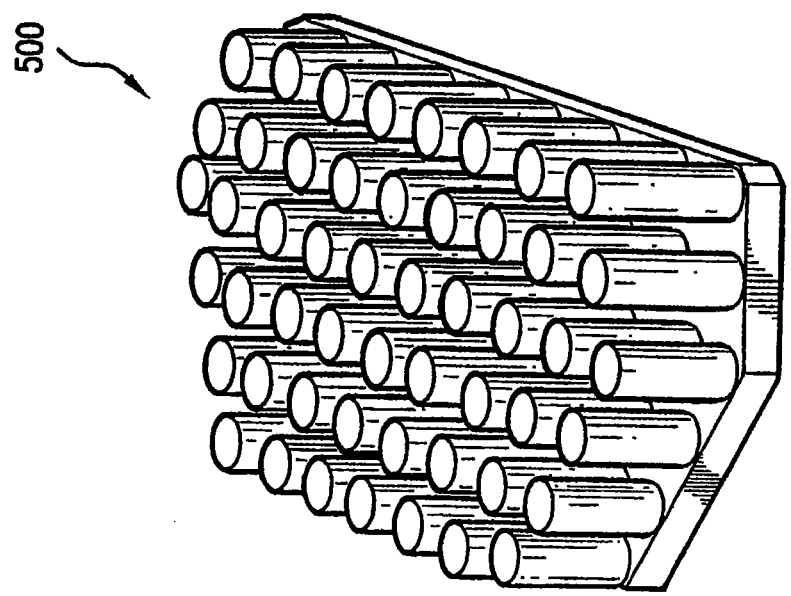
FIG. 5 illustrates an array of circular piezoelectric elements according to an embodiment of the invention.
Figure 4:
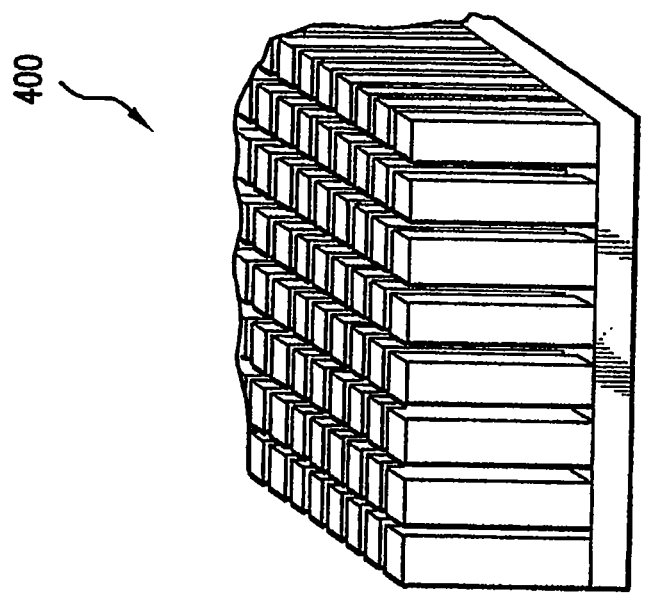
FIG. 4 illustrates an array of rectangular piezoelectric elements according to an embodiment of the invention.

FIG. 4 illustrates a two-dimensional array 400 of rectangular piezo ceramic elements 200. Array 400 can be made from lead zirconate titanate (PZT). PZT is an inexpensive material. In an embodiment, array 400 is similar to a PZT 1-3 composite used in medical applications. The piezo ceramic elements of sensor 110 according to the invention can have shapes other than rectangular. As illustrated in FIG. 5, sensor 110 can comprise an array 500 of circular piezo ceramic elements.

In one embodiment, array 400 can comprise rectangular piezo ceramic elements that are from about 40 microns square by 100 microns deep, thereby yielding a 20 MHz fundamental frequency sonic wave. A spacing of 10 microns is used between elements in this embodiment in order to provide a 50-micron pitch between elements. A pitch of 50-micron enables an identification device according to the invention to meet the Federal Bureau of Investigation's quality standards for fingerprints.

Other embodiments of the invention use geometries different than the preferred embodiment. For example, a pitch of greater than 50 microns can be used. Other embodiments also operate at frequencies other than 20 MHz. For example, embodiments can operate at frequencies of 30 MHz and 40 MHz, in addition to other frequencies.

Also, for example, in another embodiment, array 400 can comprise cuboid (rectangular parallelepiped) piezo ceramic elements that are from about 80 square by 220 microns deep. A spacing of about 20 microns is used between elements in this embodiment in order to provide about In yet another embodiment, array 400 can comprise rectangular piezo ceramic elements that are from about 200 microns square by 500 microns deep. The cuboids can be modified to prisms or extruded stars, or have chamfered corners or be a to reduce cross talk, facilitate molding respectively.

Figure 6:
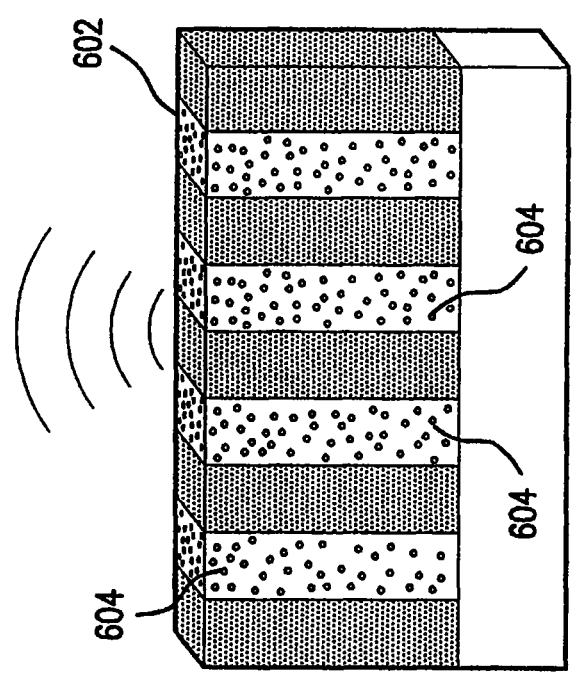
FIG. 6 illustrates a row of rectangular piezoelectric elements having a fill material between elements according to an embodiment of the invention.

As shown in FIG. 6, the spacing between the elements of a sensor array according to the invention can be filled-in with a flexible type material or filler 602 to suppress any shear waves and give the sensor improved mechanical characteristics. Micro-spheres 604 can be added to the filler 602 (e.g., vinyl micro-spheres) to reduce weight and/or increase the suppression of shear waves. In order to optimize the signal-to-noise ratio of an identification device, and the device sensitivity, fillers (e.g., araldite filled with air filled vinyl micro-spheres) that provide high acoustical attenuating and electrical isolation should be used.

At least four fabrication methods exist for producing array 400. These methods include: laser cutting, dicing, molding, and screen-printing. Laser cutting involves using an excimer laser to cut small groves and thereby form the elements of array 400. Dicing involves using high performance dicing equipment to form groves and the elements of array 400. Molding involves using injection molding equipment to form array 400. Screen-printing is a technique similar to that of solder printing in the assembly of printed circuit boards, where highly automated screen printing machines are adapted with laser cut stencils. This method is particularly suited to producing 20 MHz sonic wave elements since the ceramic elements are only 100 microns thick.

This method involves producing a ceramic slurry of appropriate consistency, and has the advantage of not requiring surface grinding as may be required with the molding method.

Figure 7A:
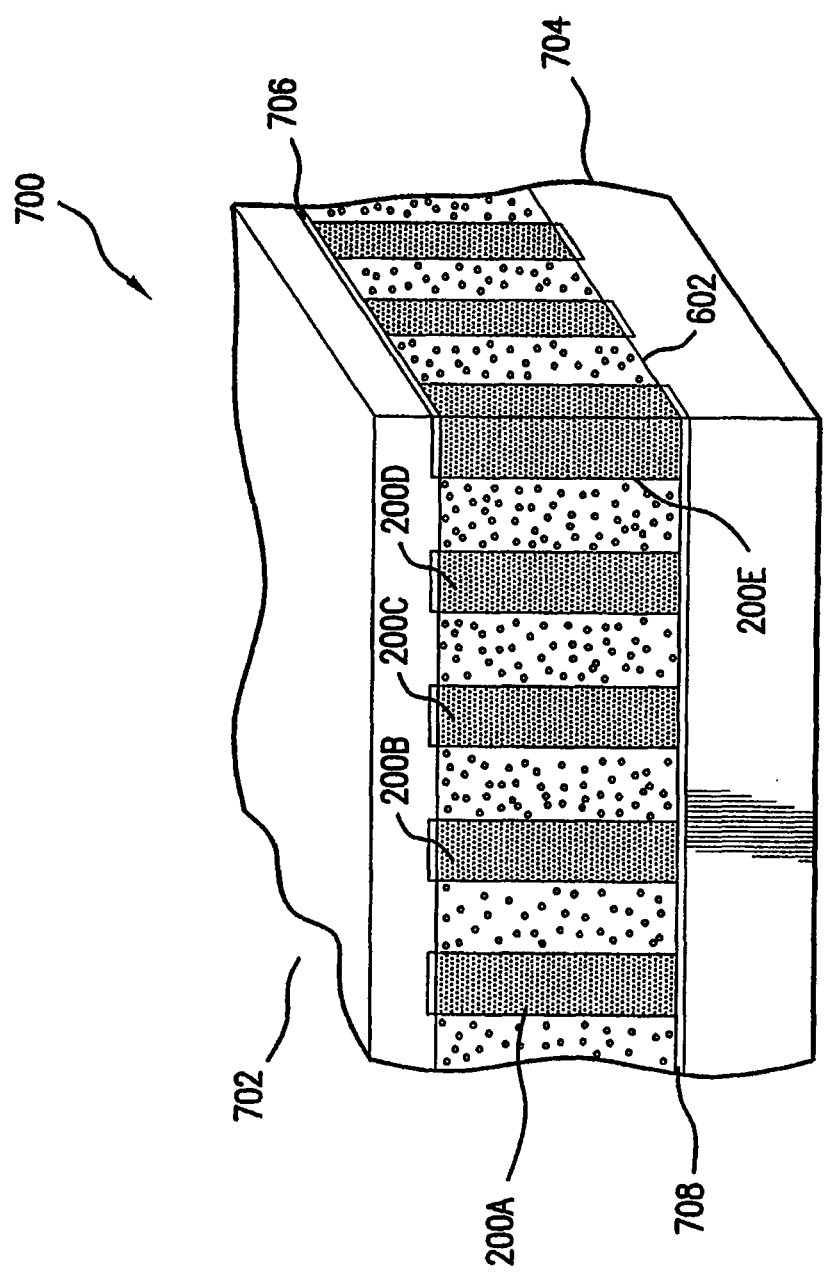
FIGS. 7A and 7B illustrate sensor arrays according to embodiments of the invention.

FIG. 7A illustrates a sensor array 700 comprising rectangular piezo ceramic elements according to a preferred embodiment of the invention. Sensor array 700 is a multi-layer structure that includes a two-dimensional array of rectangular piezo ceramic elements 200, similar to array 400. Conductors (such as conductors 706 and 708) are connected to each of the rectangular piezo ceramic elements 200. The conductors connected to one end of each element 200 (e.g., conductor 706) are oriented orthogonal with respect to the conductors connected to another end of each element 200 (e.g., conductor 708). A shield layer 702 can be added to one side to provide a protective coating where a finger can be placed proximate to sensor array 700. A support 704 can be attached to the opposite end of the sensor array. Sensor array 700 is described in more detail below.

Piezo Film Sensors

Figure 7B:
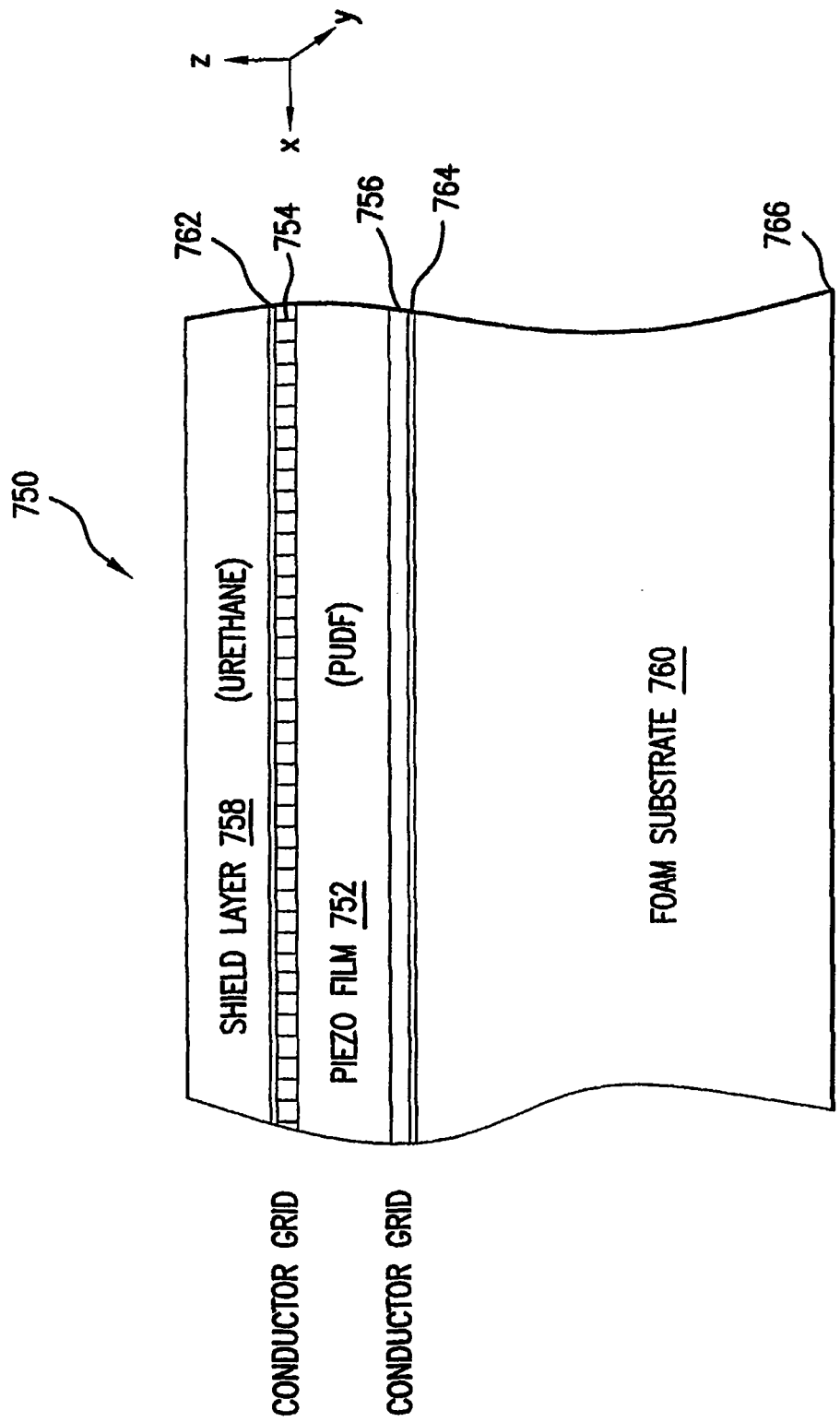

FIG. 7B illustrates a sensor array 750 comprising piezoelectric film (piezo film) according to an embodiment of the invention. FIG. 7B is a cross-sectional view of sensor array 750. Sensor array 750 is a multi-layer structure that includes a piezoelectric layer 752 sandwiched by two conductor grids 754 and 756. Conductor grids 754 and 756 each consist of rows of parallel electrically conductive lines. Preferably, the lines of grid 754 are oriented orthogonal with respect to the lines of grid 756 (that is, in x and y directions, respectively). This orientation creates a plurality of individually addressable regions or elements in the piezo film. As used herein, the term element refers to any region of a sensor array that can be addressed, either individually or as part of a larger region, using the rows of parallel electrically conductive lines (conductors). Piezoelectric polymer film sensors are further described in Piezo Film Sensors: Technical Manual, available from Measurement Specialities, Inc. Norristown, Pa. Apr. 2, 1999 REVB (incorporated by reference herein in its entirety).

Shield layer 758 can be added to one side where a finger is placed to provide a protective coating. Foam substrate 760 can be used as a support. As shown in FIG. 7B, the multiple layers of sensor array 750 are stacked along one direction (e.g., a z-direction).

In an embodiment, piezo layer 752 is a polarized fluoropolymer film, such as, polyvinylidene flouride (PVDF) film or its copolymers. Conductor grids 754 and 756 are silver ink electrodes printed on opposite sides of the PVDF film 752. Shield layer 758 is made of urethane or other plastic. Foam substrate 760 is made of TEFLON. An adhesive 762, 764 holds shield layer 758 and foam substrate 760 on opposite sides of the printed PVDF film 752 as shown in FIG. 7B.

In an embodiment, the PVDF film, including the printed electrodes, can be peeled off like a label for easy replacement. As shown in FIG. 7B, sensor array 750 can be mounted by adhesive 766 onto wax paper or other material (not shown) for easy peel off. This allows the piezo sensor to be installed and/or replaced simply and easily at minimum cost. Compared to optical and silicon technologies, maintenance of the piezo sensor array 750 is trivial.

Sensor Array Address Lines

Figure 8:
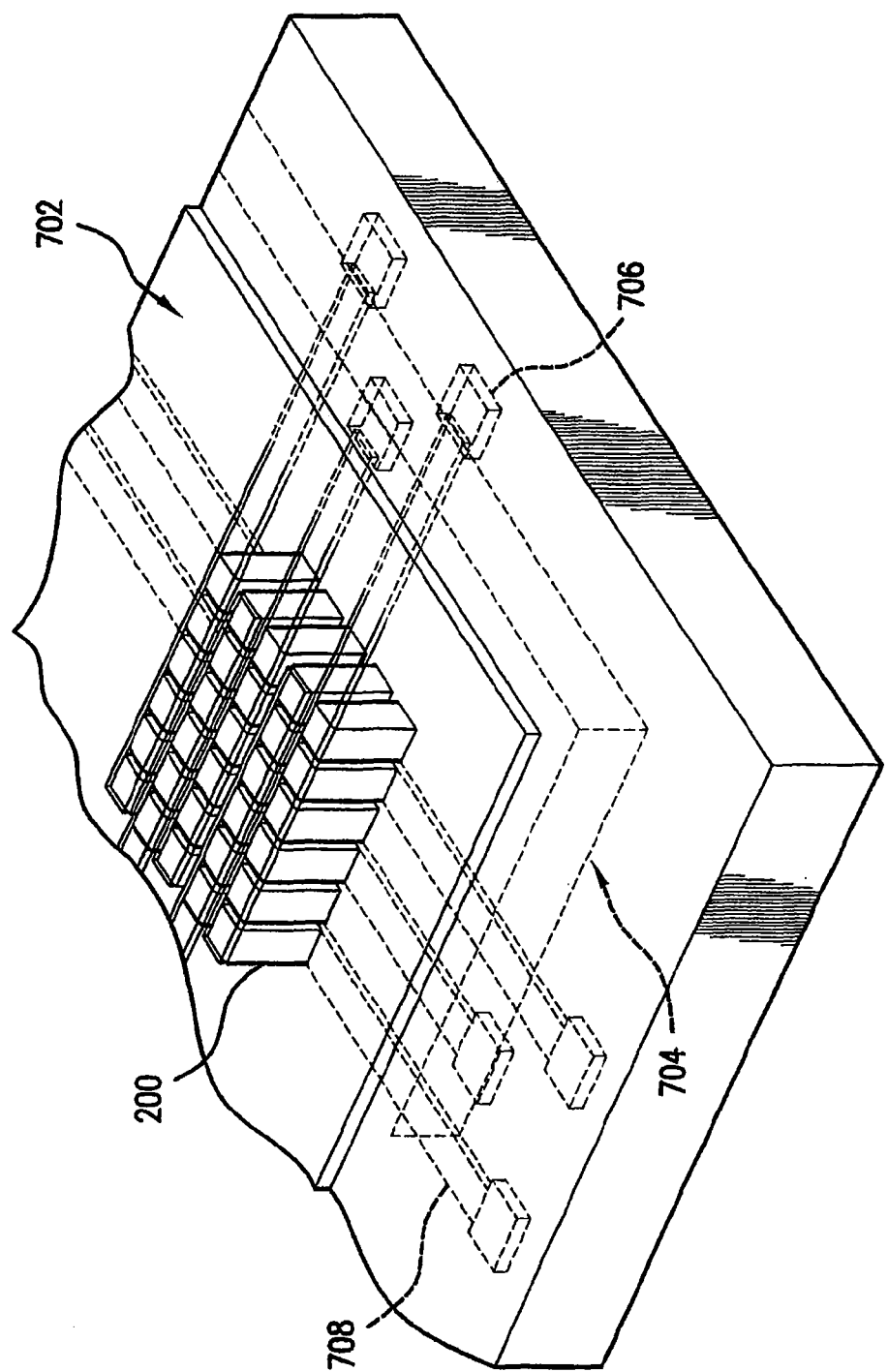
FIG. 8 illustrates a more detailed view of the sensor array of FIG. 7A.

FIG. 8 illustrates a more detailed view of sensor array 700. As described above, sensor array 700 comprises piezo ceramic elements having an filler 602. Filler 602 preferably contains micro-spheres 604. This structure is then sandwiched between several layers. This central composite layer is an active structure that can be used, for example, to map fingerprint mechanical impedances into a matrix of electrical impedance values.

Each rectangular piezo ceramic element 200 of sensor array 700 is connected to two electrode lines (e.g., conductors 706 and 708). The electrode lines on one end of sensor array 700 run perpendicular to the electrode lines on opposite end of sensor array 700. Thus, any single element 200 of the array can be addressed by selecting the two electrode lines connected to it. The electrode lines are preferably created by vacuum despoliation and lithography, and they are connected to the switching electronics via an interconnect technique described below.

On top of the one set of electrode lines is a protection layer 702. Protective layer 702 is preferably made of urethane. This protecting layer 702 is intended to be in contact with a finger during operation of the sensor.

A support 704 or backing layer serves as a rear acoustical impedance for each of the rectangular piezo ceramic elements 200. In a preferred embodiment, support 704 is made of TEFLON foam. In order to provide a large variation of the electrical impedance of an element when loaded and unloaded, the acoustical impedance support 704 should be acoustically mismatched to the sensor element material. Either a very low or a very high acoustic impedance material can be used. For embodiments using piezo ceramic materials, the preferred impedance mismatch can be obtained by an air backing rather than by a hard backing. This is because the sensor has a high acoustic impedance.

The materials described herein for constructing sensor array 700 are illustrative and not intended to limit the present invention. Other materials can be used, as would be known to a person skilled in the relevant art.

Figure 9:
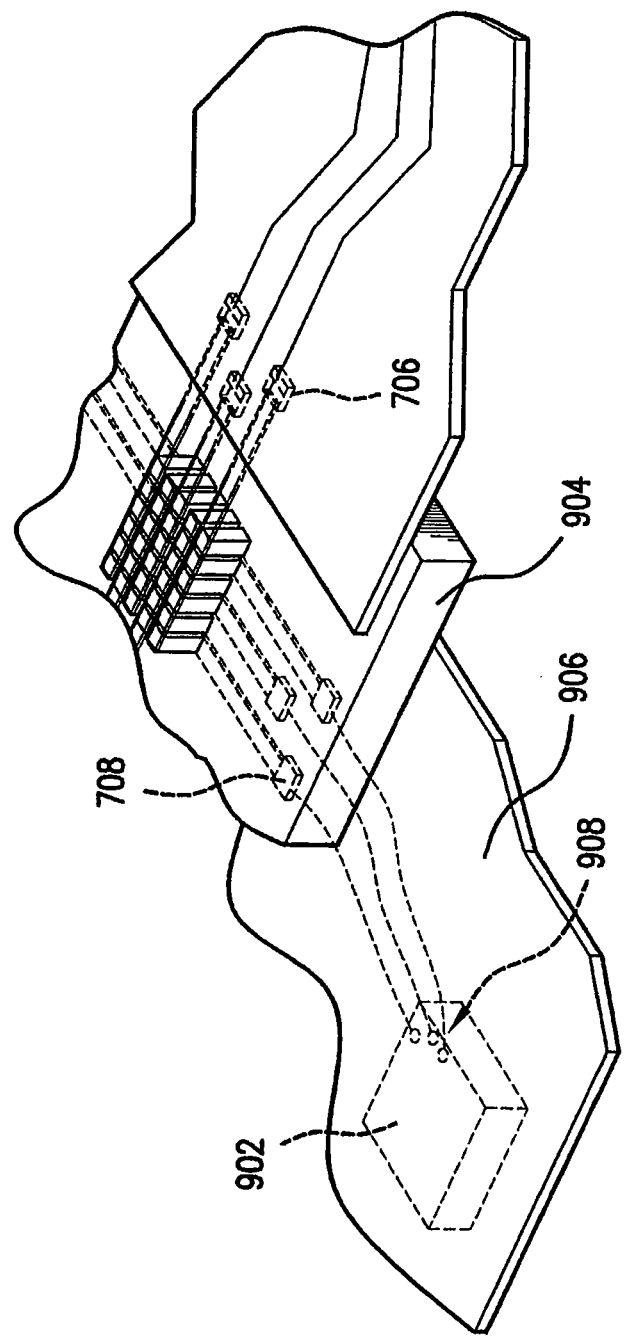
FIG. 9 illustrates how the sensor array of FIG. 8 is connected to an application specific integrated circuit.

FIG. 9 illustrates how sensor array 700 can be connected to an application specific integrated circuit. As described herein, an individual piezo ceramic element (m, n) of sensor array 700 can be addressed by selecting (addressing) conductor m on the top of sensor array 700 and conductor n on the bottom of sensor array 700. Other conductors can be either grounded or open (high impedance state), particularly those conductors used to address elements in the neighborhood of the element being selected, in order to reduce cross-talk. Parasitic currents in the neighborhood of the selected element are minimized mechanically by the interstitial filler 602, described above with regard to FIGS. 6 and 7A. Since in one embodiment, the spacing between elements (pitch) is about 50 microns and standard bonding technologies require a pitch of about 100 microns, alternate rows on an "East" and "West" and alternate columns on a "North" and "South" sides of sensor array 700, as shown in FIG. 9, connect the sensor to the "outside world". As shown in FIG. 9, These conductors can be terminate in a "Bump" technology around three edges 908 of an ASIC multiplexer 902. In an embodiment, side 908 of ASIC multiplexer 902 is about 3 mm.

In an embodiment, ASIC multiplexer 902 is connected to a high density flex 906. High density flex 906 is connected to an epoxy substrate 904. Conductors can be formed or attached to the high flex to couple the conductors of the array to ASIC multiplexer 902. For example, a conductor on high density flex 906 is shown in FIG. 9 coupling conductor 708 to ASIC multiplexer 902. Conductor is coupled to ASIC multiplexer 902 by bump soldering. Anisotropic glue can be used to couple the conductor on high density flex 906 to conductor 708 of the sensor array. Other means for connecting and electrically coupling ASIC multiplexer 902 to sensor array 700 are known to persons skilled in the relevant art, and these means also can be used in accordance with the invention.

Figure 10:
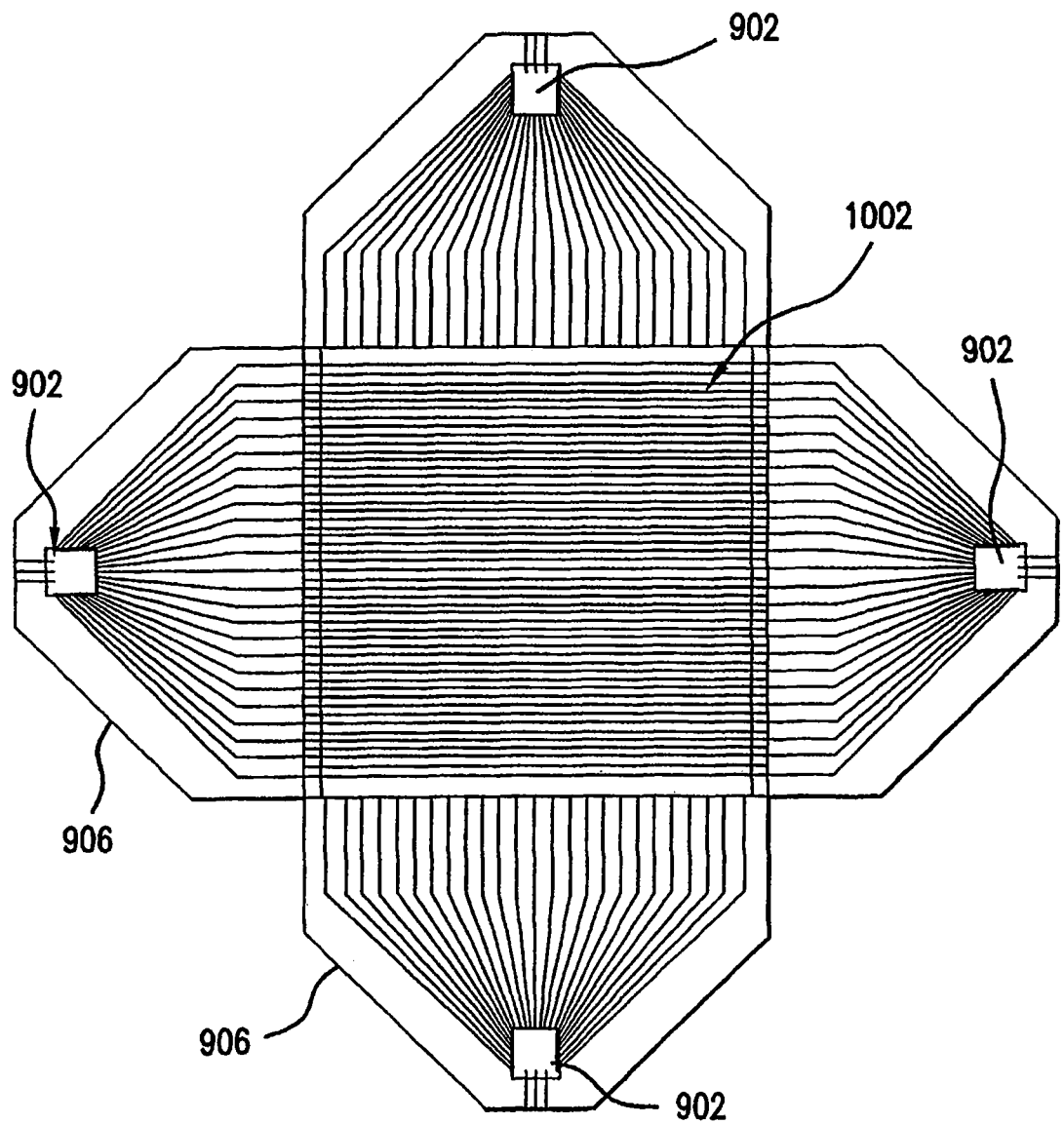
FIG. 10 illustrates how to connect a sensory array to multiplexers according to an embodiment of the invention.

FIG. 10 illustrates how to connect a sensory array 1002 to four ASIC multiplexers 902 according to an embodiment of the invention. As described herein, electrode lines or conductors can be vapor deposited on both sides of the substrate 902 (not shown in FIG. 10) and then etched into the desired pattern. Before the line and row pattern is etched, substrate 902 should be polarized in a manner similar to that of medical transducers.

A polarized substrate is connected to a socket or multi chip module case that is compatible with available printed circuit board technologies. The piezo ceramic matrix or sensor array 1002 can be backed by an air equivalent foam or aluminum oxide. Either backing is designed to miss-match the composite piezo material at 8 Mrayls to cause any energy coupling to occur only at the front face of sensor array 1002, where for example a fingerprint can be scanned. It should be noted in FIG. 10 that the conductors on both the top and bottom of sensor array 1002 are interleaved in the manners described above to facilitate bonding technologies requiring a pitch of about 100 microns.

Figure 11:
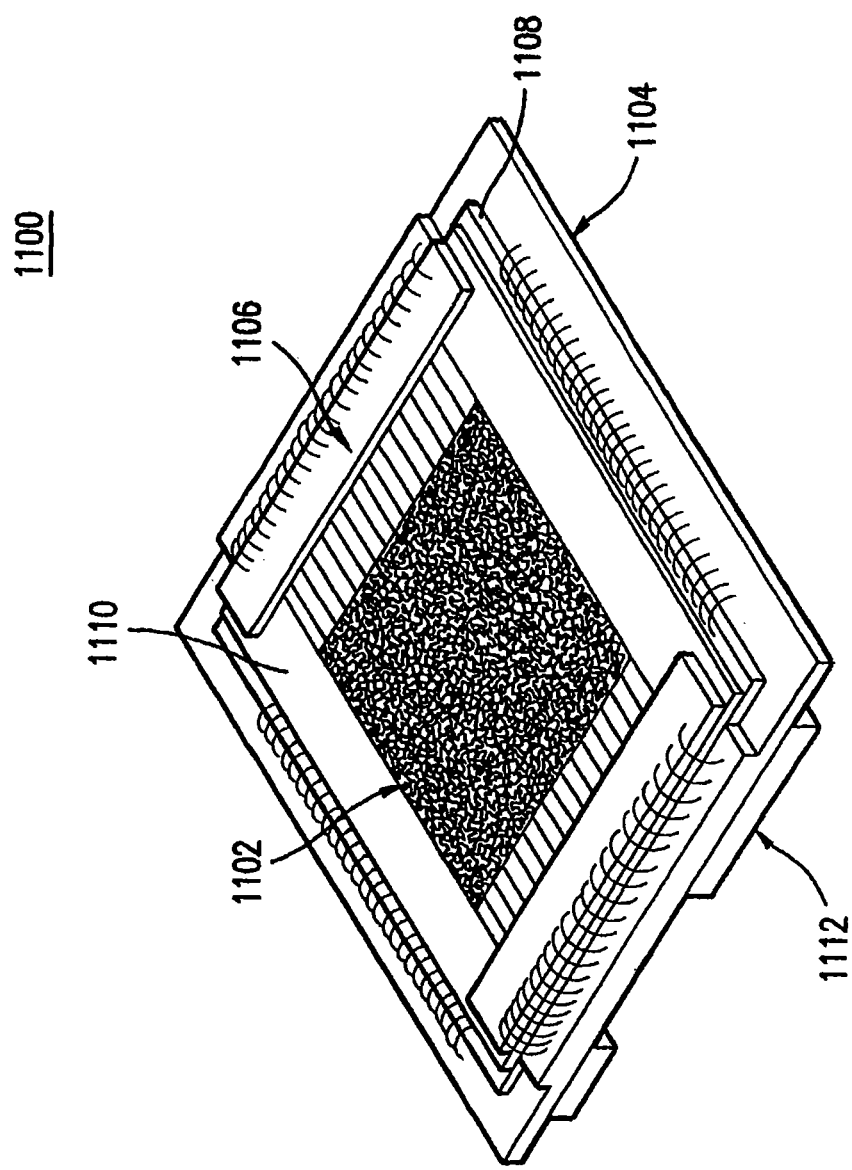
FIG. 11 illustrates an identification device according to an embodiment of the invention.

FIG. 11 illustrates an identification device 1100 according to an embodiment of the invention. In a preferred embodiment, device 1100 has a piezo ceramic sensor array 1102 that is physically lager enough to capture any fingerprint placed without accuracy on sensor array 1102 (e.g., about 25 mm square). Sensor array 1102 is preferably compliant with CJIS ANSII NIST standards in resolution (500 points per 25.4 mm), and it has a pixel dynamic range sufficient to provide 256 distinct shades of gray.

As show in FIG. 11, in an embodiment, substrate 1110 is attached to a printed circuit board 1104. The conductors of sensor array 1102 are coupled to two integrated circuits 1106 and two integrated circuits 1108, which couple sensor array 1102 to other circuits, which are described elsewhere herein. Integrated circuit 1112 is a wireless transceiver that enables embodiments of the invention to communicate with other devices as part of a personal area network. This connectivity permits embodiments of the invention to supply, for example, a standard secure identification and/or authorization token to any process or transactions that need or require it. The connection scheme shown is FIG. 11 is an alternative connection scheme that can be used to implement embodiments of the invention.

The above sensor array descriptions are illustrative and not intended to limit the present invention. For example, piezo layer 752 can be any material exhibiting a piezoelectric effect including, but not limited to, piezoelectric polymers. Conductor grids 706, 708, 754 and 756 can be any electrically conductive material including, but not limited to, metals. Likewise, other types of protective material can be used for shield layers 702 and 758 as would be apparent to a person skilled in the art given this description. Other types of supportive material can be used in place of support 704 or foam substrate 760.

Example Identification Device

Figure 12:
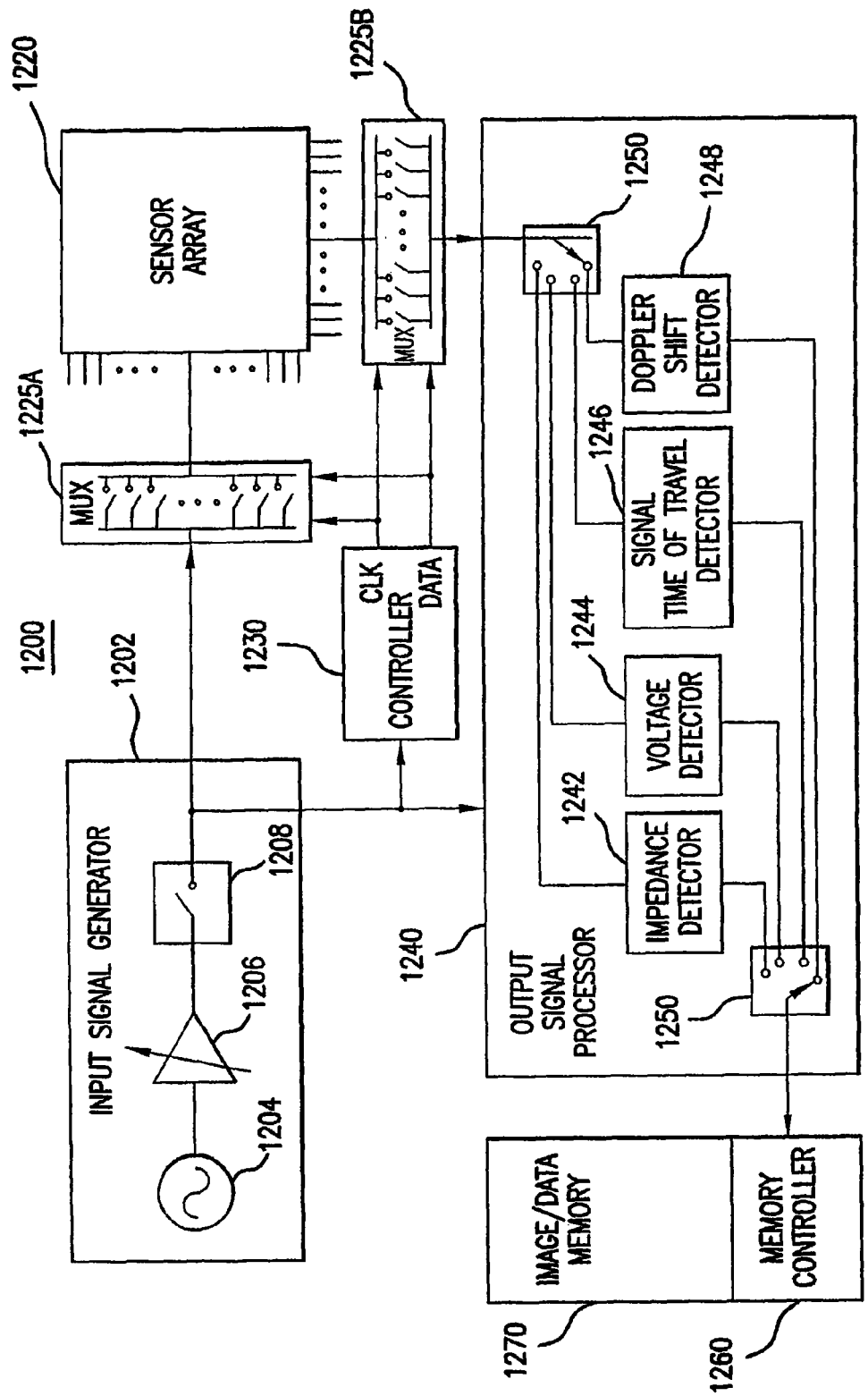
FIG. 12 illustrates circuit components of an identification device according to an embodiment of the invention.

FIG. 12 illustrates an identification device 1200 according to an embodiment of the invention. Device 1200 comprises an input signal generator 1202, a sensory array 1220, an output signal processor 1240, a memory controller 1260, and a memory 1270. Sensor array 1220 is coupled to input signal generator 1202 and output signal processor 1240 by multiplexers 1225A and 1225B, respectively. A controller 1230 controls the operation of multiplexers 1225A and 1225B. The operation of identification device 1200 is further described below.

In an embodiment, input signal generator 1202 comprises an input signal generator or oscillator 1204, an variable amplifier 1206, and a switch 1208. In one embodiment, oscillator 1204 produces a 20 MHz signal, which is amplified to either a low or a high voltage (e.g., about 4 volts or 8 volts) by variable amplifier 1206, depending on the mode in which device 1200 is operating. Switch 1208 is used to provide either no input signal, a pulsed input signal, or a continuous wave input signal. Switch 1208 is controlled to produce the various types of input signals described herein in a manner that would be known to a person skilled in the relevant art. As shown in FIG. 12, the input signal generated by input signal generator 1202 is provided to sensor array 1220, through multiplexer 1225A, and to controller 1230 and output signal processor 1240.

The structure and details of sensor array 1220 are explained above. In a preferred embodiment, sensor array 1220 is a piezo ceramic composite of rectangular elements designed to operate with a 20 MHz input signal.

Example Multiplexer

Figure 13A:
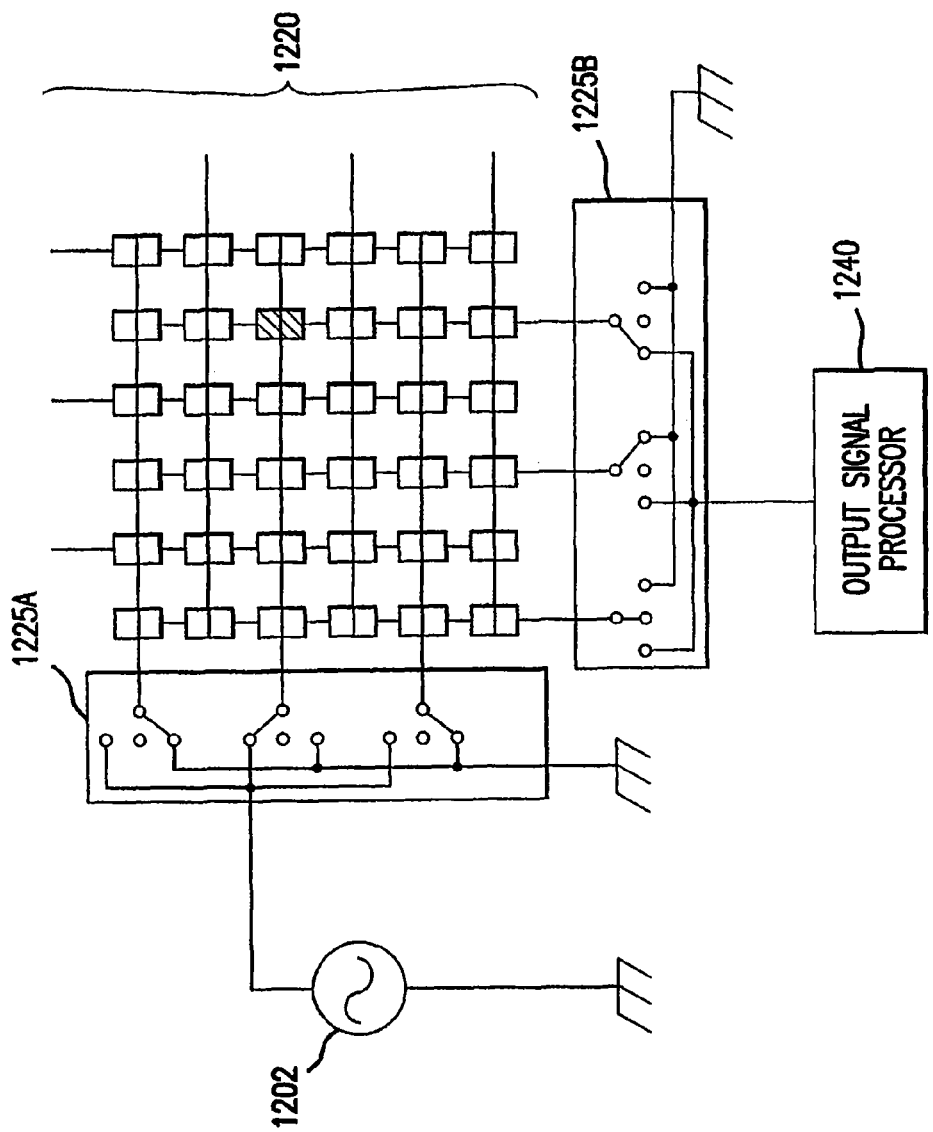
FIG. 13A illustrates how to apply an input signal to the sensor array of FIG. 12 and receive an output signal from the sensor array according to an embodiment of the invention.

FIGS. 13A and 13B illustrate how to apply an input signal generated by input signal generator 1202 to the sensor array 1220, and how to receive an output signal from sensor array 1220 according to an embodiment of the invention. In one embodiment, sensor array 1220 comprises 200,000 elements 200 arranged in a two-dimensional array (i.e., a 500.times.400 element array). The 500 conductors of array 1220 that connect, for example, to the element rows on the bottom of array 1220 must be connected to input signal generator 1202, either one at a time or in various groupings, while the 400 lines that connect to the columns on the top of the array 1220 must be connected, for example, to an impedance meter or Doppler circuit, either one at a time or in various groups. This task is accomplished by multiplexers 1225.

In another embodiment, the sensor array 1220 can include about 25,000 to about 64,000 elements 200 (e.g., with 80.times.80.times.200 micron elements). Yet another embodiment can include about 16,000 elements 200 (e.g., with 200.times.200.times.500 micron elements).

In an embodiment, multiplexers 1225 are incorporated into four identical ASICs (see FIG. 10). These four ASICs comprise analog multiplexers, amplifiers, detection circuits, and logic. In a preferred embodiment, the voltage of the input signal to sensor array 1220 is restricted to less than 8 volts, which permits the ASICs to be constructed using 3-micron geometry, and to attain a switch impedance of less than 5 ohms. The four basic sections of each of these ASIC are: (1) multiplexers as described herein; (2) amplifier/automatic gain controllers; (3) Doppler detectors; and (4) a digital signal processor (DSP) interface. The structure and implementation of items (2) through (4) are known to persons skilled in the relevant art.

In an embodiment, multiplexers 1225 comprise seventeen 16:1 multiplexers, thus giving one output or 16 outputs as selected. The function of each switch in the multiplexer is determined by a shift register 1302 that is 272 bits long and 2 bits wide (see FIG. 13B). The loading and clocking of shift register 1302 is performed by controller 1230, which comprises a counter and logic that would be known to a person skilled in the relevant art. As shown in FIG. 13A, the conductors of sensor array 1220 can be connected to either ground, signal input generator 1202, or they can be unconnected (high impedance). Multiplexer 1225A is designed for lowest "on" resistance. Multiplexer 1225B connects all (256) conductors of one side of sensor array 1220 to one or sixteen sense nodes. Both multiplexers 1225A and 1225B are connected to the same function logic (i.e, controller 1230) so that the proper sensor elements are selected and used, for example, for voltage sensing. Element columns and rows, in the neighborhood of an element or group of elements selected for sensing, can be switched to ground to prevent coupling and interference.

Figure 14:
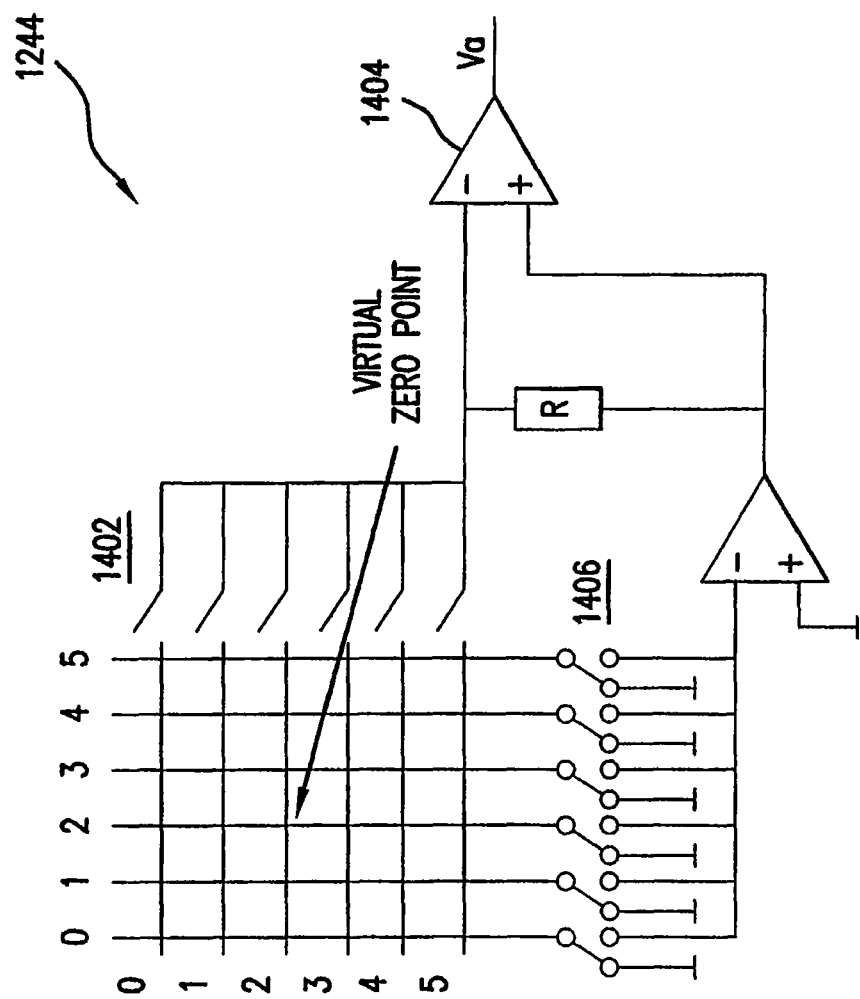
FIG. 14 illustrates an example voltage sensing circuit according to an embodiment of the invention.

FIG. 13B illustrates how to control the switches of multiplexers 1225 according to an embodiment of the invention. As described herein, each switch of multiplexer 1225 connected to a conductor of array 1220 can be in one of three states: connected to ground, connected to signal input generator 1202, or open (high impedance). This can be implemented, for example, using two CMOS gates, as shown in FIG. 14. A 272 bit long by 2 bit wide shift register can then be used to control the position of each switch. Bits from controller 1230 are shifted into shift register 1302 to control the position of the switches of multiplexers 1225. In an embodiment, shift register 1302 is coupled to the switches of multiplexer 1225 using latches so that the position of the multiplexer switches remain constant as new bits are being shifted into shift register 1302. How to implement this embodiment would be known to a person skilled in the relevant art. Other means for implementing the functionality of multiplexers 1225 can be used without departing from the scope of the invention.

FIG. 14 illustrates an example voltage detector 1244 according to an embodiment of the invention. As will be understood by a person skilled in the relevant art, the voltage drop in each conductor of sensor array 1220 is large compared to the voltage drop of the elements of the array because all the elements coupled to a particular conductor are drawing from a signal source (i.e., input signal generator 1202). If each element has an impedance of 500 ohms, the impedance of 400 elements connected in parallel is 1.25 ohms. This situation can be compensated for, however, by using a second multiplexer to measure the true output voltage of the elements. As can be see in FIG. 14, multiplexer 1402 is used to move the virtual zero-point of the amplifier 1404 before the switch of multiplexer 1406.

As explained herein, the choice of apertures, their relative position in sensor array 1220, and the number of apertures intended to be operated simultaneously will affect the complexity of the logic of for multiplexer 1225. Thus, in a preferred embodiment, this logic is implemented using a DSP. The mode of operation of device 1200 can be selected on the four identical ASICs described above using mode switches. These mode switches can be used to operate switches 1250 (see FIG. 12) to direct the output of multiplexer 1225 B to the proper detector of output signal processor 1240.

The operation of impedance detector 1242, signal time of travel detector 1246, and Doppler shift detector 1248 are described below. Circuits to implement the functionality of these detectors will be known to persons skilled in the relevant art given their descriptions herein.

Figure 21:
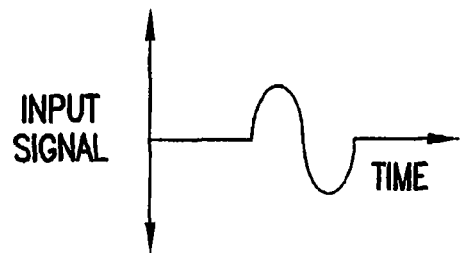
FIG. 21 illustrates a sensor array input signal according to an embodiment of the invention.

The output of output signal processor 1240 is biometric data. This data can be stored in memory 1270 using memory controller 1260. FIG. 21 is a flowchart of a method according to an embodiment of the invention. Use of this biometric data is described below.

Figure 15:
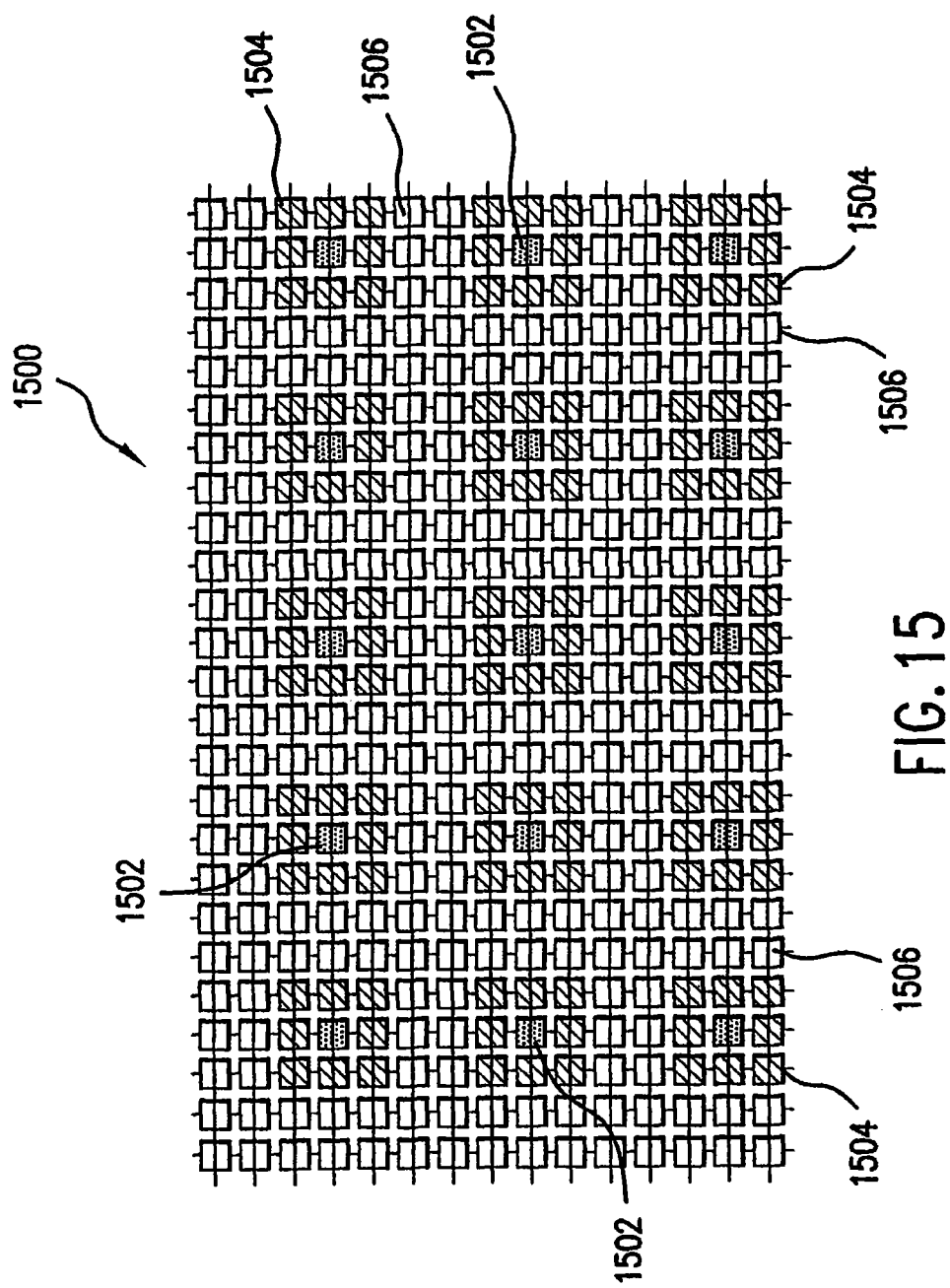
FIG. 15 illustrates how to minimize cross-talk in a sensor array according to an embodiment of the invention.

FIG. 15 illustrates means for increasing scanning speed and minimizing cross-talk in a sensor array 1500 according to an embodiment of the invention. As seen in FIG. 15, multiple elements can be active simultaneously and a first means for minimizing cross-talk is to separate geographically the active elements 1502 of array 1500. As explained herein, a dynamic grounding scheme (i.e., coupling the elements 1504 in the neighborhood of an active element 1502 to ground) can be used that moves with the active elements 1502 as they scan across the sensor array 1500. This reduces the capacitive coupling to ground and electrical cross-talk while maintaining a Faraday Cage for all sensed frequencies. In addition, an interstitial filler can be used to reduce cross-talk and thereby the parasitic currents in the neighborhood of the selected elements 1502. Other elements of array 1500, e.g., elements 1506, are connected to conductors that are open.

Example Method Embodiments of the Invention

Figure 16:
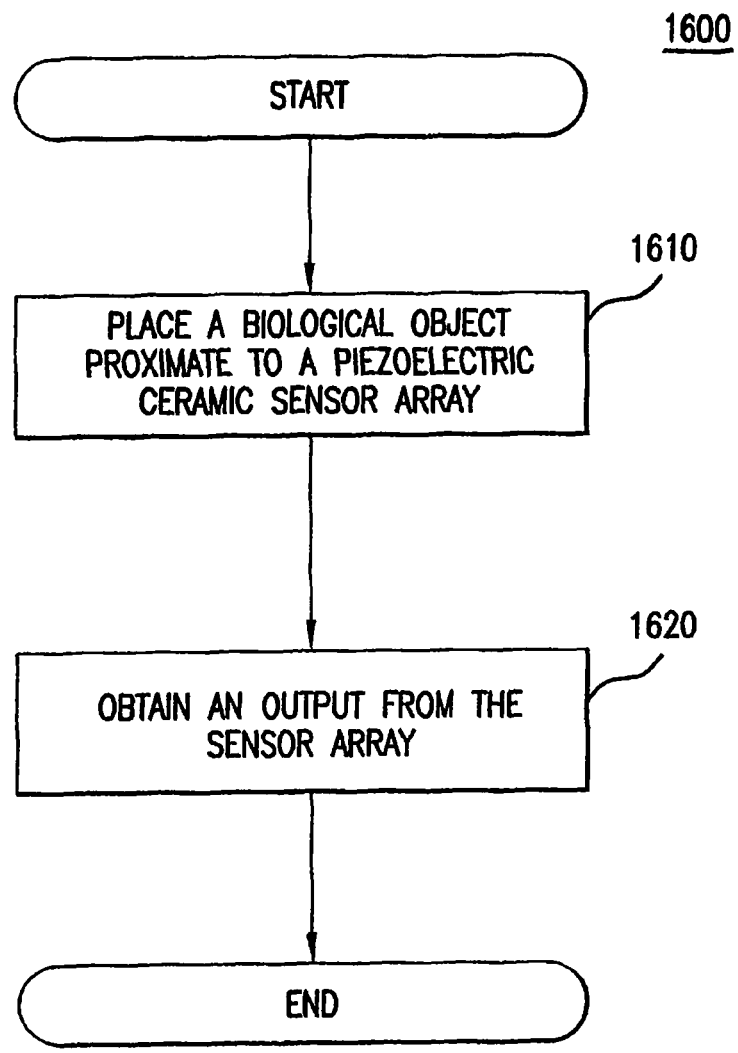
FIG. 16 is a flowchart of a method according to an embodiment of the invention.

FIG. 16 is a flowchart of a method 1600 according to an embodiment of the invention. Method 1600 comprise two steps 1610 and 1620. In step 1610, a biological object, for example, a finger or a hand, is place proximate to a piezoelectric ceramic array. In step 1620, an output is obtained from the sensor array. The obtained output is processed as explained below to obtain biometric data that can be used to recognize or verify the identity of a person, whose finger or hand, for example, was placed proximate to the sensor array.

Each of the steps 1610 and 1620 are described further below with regard to the various operating modes of device 1200, described above.

As described herein, identification device 1200 is operated in different modes depending on the biometric data to be obtained. The biometric data that can be obtained using device 1200 includes fingerprints, bone maps, arteriole blood flow, and/or capillary blood flow.

Figure 17:
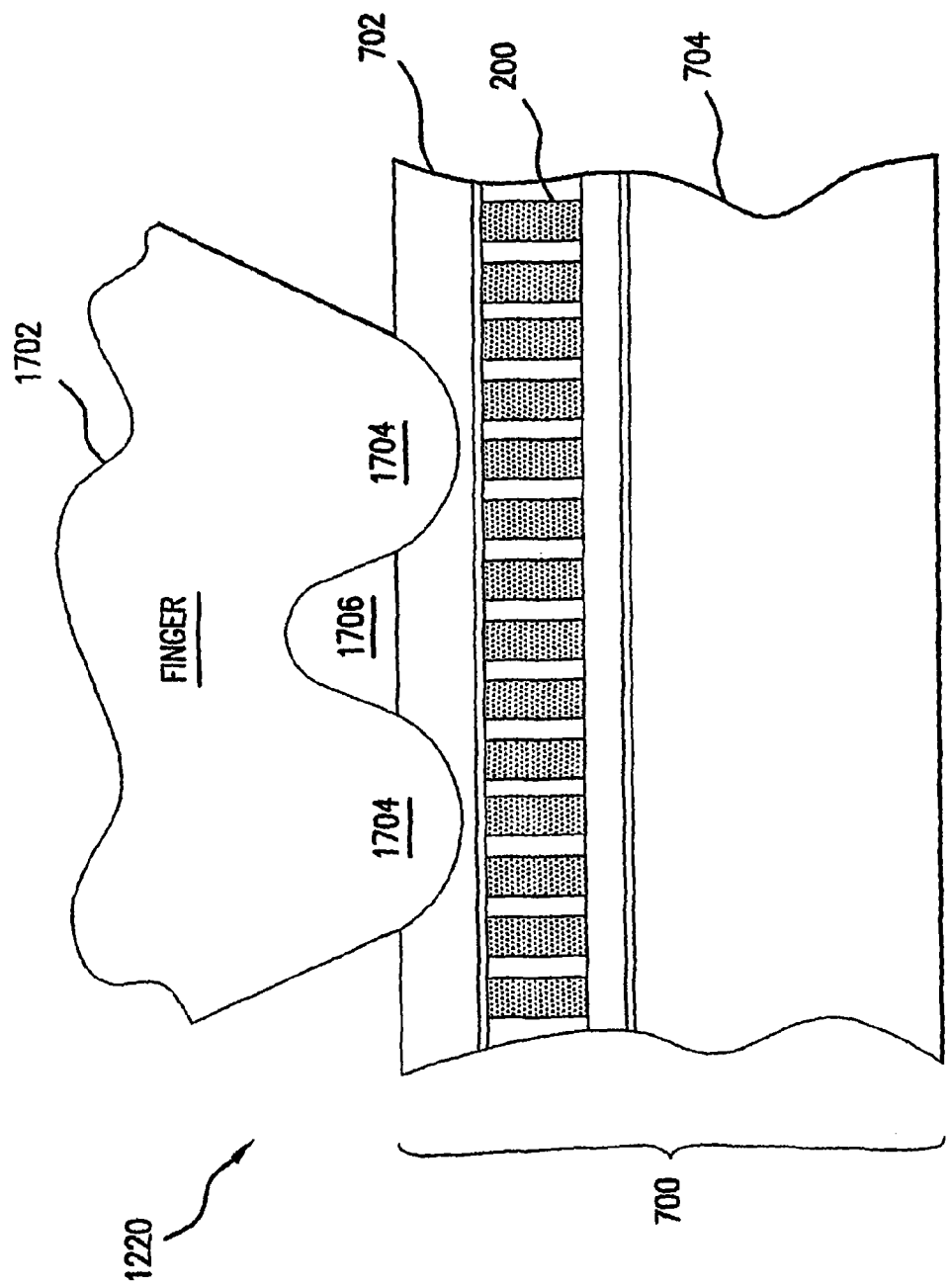
FIG. 17 illustrates using an identification device to obtain biometric information according to an embodiment of the invention.

FIG. 17 illustrates using identification device 1200 to obtain a fingerprint of a finger according to an embodiment of the invention. As seen in FIG. 17, finger 1702 is place proximate to the sensor array 1220 of device 1200. In a preferred embodiment, sensor array 1220 is similar to piezo ceramic sensor array 700.

Two fingerprint ridges 1704 of finger 1702 are in direct contact with protective shield 702. A fingerprint valley (i.e., cavity) 1706 of finger 1702 is not in direct contact with protective shield 702. As can be seen in FIG. 17, there are approximately six piezo ceramic elements 200 between the adjacent fingerprint ridges 1704.

Initially, device 1200 is in a power saving mode. This mode is particularly useful for prolonging battery life in mobile versions of device 1200. When finger 1702 applies a force to sensor array 1220, a wake-up circuit 1800 (see FIG. 18) operates to turn-on device 1200.

Wake-up circuit 1800 comprises a capacitor 1802, a diode 1804, and a switch 1806. When finger 1702 applies a force to piezo ceramic elements 200, a voltage is developed by the elements causing capacitor 1802 to accumulate a charge. When enough charges has been accumulated, the voltage so produced causes switch 1806 to be turned-on. Voltage source 1808 is used to power device 1200 once switch 1806 is turned-on. Power will continue to be supplied to device 1200 until capacitor 1802 is discharged using a turn-off circuit (discharging resister not shown).

After device 1200 wakes-up, device 1200 can be operated in either an impedance detection mode or an attenuation mode (voltage mode) in order to obtain an output from sensor array 1220 that can be processed to obtain the fingerprint of finger 1702. Each of these modes are explained below.

The outputs of the elements of piezo sensor 200 can be summed to determine the centroid of the point of contact of the finger with the device. Any movement of the finger across the device can thus be sensed and the sensor 200 can be used as a pointing device. For example, the centroid of a finger in contact with piezo sensor 200 can be used to point on interconnected viewing devices. The sum of the sensors elements can also used to determine if the user is pressing with too little or two much force and the result fed back to the user.

Figure 18:
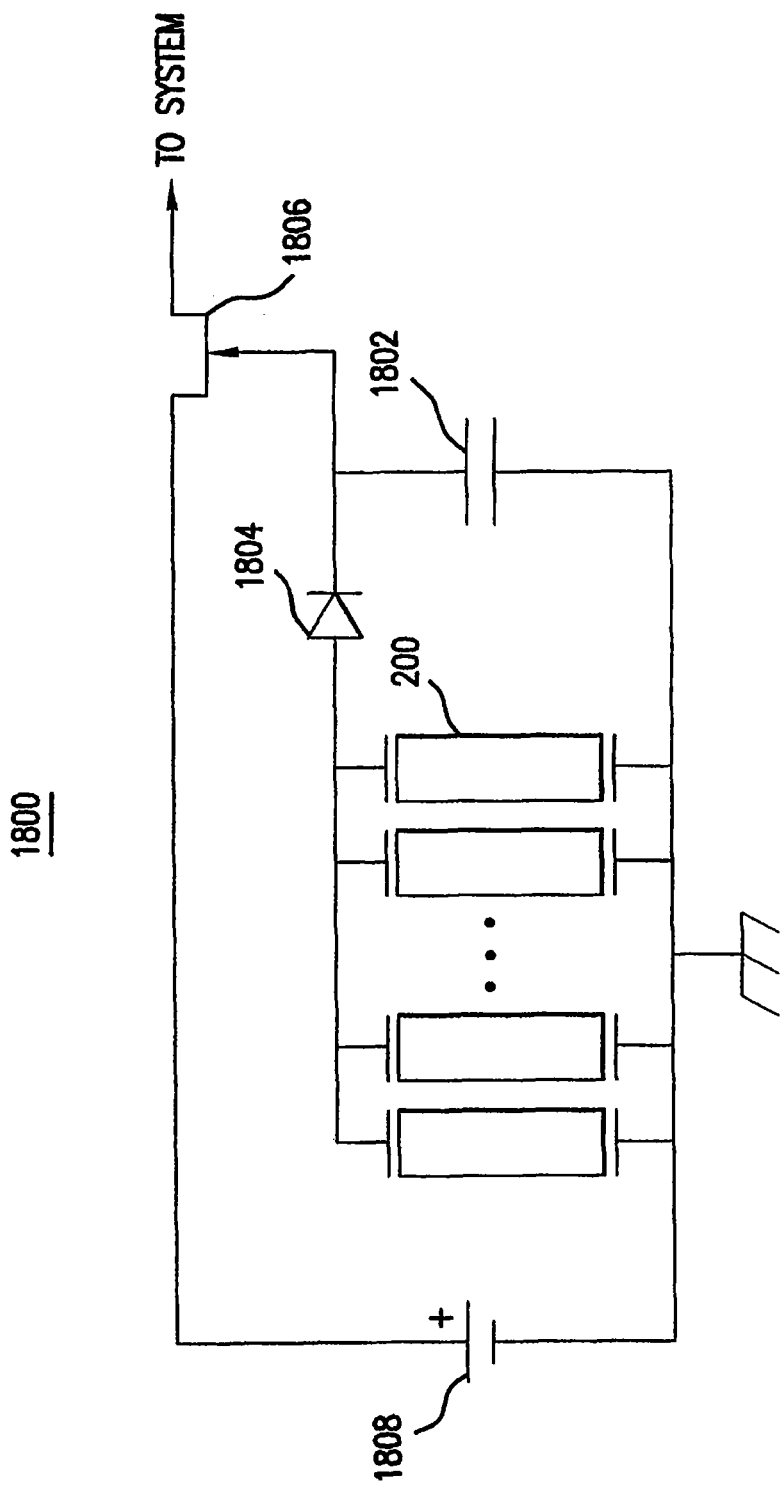
FIG. 18 illustrates an identification device wake-up circuit according to an embodiment of the invention.

The embodiment shown in FIG. 18 can also be used as a switch to make a selection on an interconnected viewing device. For example, if an analog-to-digital converter (not shown) is coupled to capacitor 1802, the voltage across capacitor 1802 is converted to a digital signal that can be used interactively to make the selection by a user. As a user varies the pressure applied to sensor 200, the voltage across capacitor 1802 will vary. The analog-to-digital converter converts this time varying voltage, for example, to a series of numbers between 00000000 (base 2) and 11111111 (base 2). The output of the analog-to-digital converter is periodically sampled and used to make and/or indicate a selection (e.g., the number can be input to a processor and used to make and/or indicate a particular selection). A graphical user interface on a viewing device provides feedback to the user and indicates to the user which of the possible selections is being selected by the user based on the pressure applied to sensor 200. To change a selection, the user simply applies either more or less pressure to sensor 200.

Impedance Mode

FIG. 19 illustrates the impedance of a single piezo ceramic element 200 loaded by a fingerprint valley 1706 according to an embodiment of the invention. At a frequency of about 19.8 MHz, the impedance of an element 200 loaded by a fingerprint valley is approximately 800 ohms. At a frequency of 20.2 MHz, the impedance is approximately 80,000 ohms. At a frequency of 20 MHz, the impedance is approximately 40,000 ohms. As can be seen when FIG. 19 is compared to FIG. 20, both the absolute impedance of an element 200 loaded with a fingerprint valley and the change in impedance with frequency of an element 200 loaded with a fingerprint valley is significantly different from that of an element 200 loaded with a fingerprint ridge. This difference can be used to obtain an output from sensor array 1220 that can be processed by output signal processor 1240 to produce fingerprint data.

FIG. 20 illustrates the impedance of a single piezo ceramic element 200 loaded by a fingerprint ridge 1704 according to an embodiment of the invention. As can be seen in FIG. 20, at a frequency of about 19.8 MHz, the impedance of an element 200 loaded by a fingerprint ridge is approximately 2,000 ohms. At a frequency of 20.2 MHz, the impedance is approximately 40,000 ohms. At a frequency of 20 MHz, the impedance is approximately 20,000 ohms. Thus, both the absolute impedance of an element 200 loaded with a fingerprint ridge and the change in impedance with frequency of an element 200 loaded with a fingerprint ridge is significantly different from that of an element 200 loaded with a fingerprint valley.

When operating in the impedance mode, identification device 1200 determines the absolute impedance of an element 200 and/or the change in impedance of an element 200 with frequency to determine whether a given element 200 is loaded by a fingerprint ridge 1704 or a fingerprint valley (cavity) 1706. To obtain a measure of the impedance of an element 200, input signal generator 1202 is used to produce low voltage pulses that are input to the elements of sensor array 1220 using multiplexer 1225A.

The output signals obtained at multiplexer 1225B are related to the absolute impedance of the elements 200 of array 1220. These output signals are routed by switch 1250 to impedance detector 1242 to determine a measure of the absolute impedances of the elements of array 1220. To obtain a fingerprint, it is only necessary that impedance detector 1242 be able to determine whether a given element 200 is loaded by a fingerprint ridge or a fingerprint valley. These determinations of whether a particular element 200 is loaded by a fingerprint ridge or fingerprint valley can be used to generate pixel data that represents the fingerprint of finger 1702. The fingerprint is stored in memory 1270. The fingerprint can also be transmitter to other devices as described below.

If the fingerprint of finger 1702 is scanned twice using two different input signal frequencies, the change in the impedances of the elements 200 with frequency can be calculated. As already described herein, the change in the impedances of the elements 200 with frequency is different depending on whether an element 200 is loaded by a fingerprint ridge or fingerprint valley. As can be seen in FIG. 12, the input signal generated by input signal generator 1202 is supplied to output signal processor 1240. Thus, output processor 1240 can determine both the frequency and the voltage of the signals being input to sensor array 1220.

An impedance detector circuit (not shown) can be implemented using an op amp. The output of multiplexer 1225B is supplied to the negative port of the op amp and an amplified signal is obtained at the output port. As would be known to a person skilled in the relevant art, the positive port of the op amp is coupled to ground and a resistance is placed between the negative port and the output port of the op amp.

If the amplified voltage at the output port exceeds a predetermined threshold voltage, the particular element 200 being measured is loaded by a fingerprint ridge. This is due to the fact that the absolute impedance of an element 200 loaded by a fingerprint ridge (for a given frequency) is approximately half of the impedance of an element 200 loaded by a finger print valley. Thus, the voltage of the output signal provided to the op amp from an element 200 loaded by a fingerprint ridge is approximately twice the voltage of the output signal provided to the op amp from an element 200 loaded by a fingerprint valley.

In general, slightly different processing techniques can be used in association with smaller piezo ceramic sensor arrays (e.g., less than about 100,00 elements) that include larger individual elements (e.g., greater than about 40 microns by 100 microns). For example, an exemplary piezo ceramic element can be comprised of a capacitor having PZT as the dielectric. The permitivity of PZT can be relatively high (e.g., above 1500 (coulombs/volt-meter).

At 1500, the piezo electric effect causes the capacitor to mechanically expand or contract under a voltage. At various frequencies, the element will exhibit preferential oscillation or clamping based on the interaction of the wavelength, the speed of sound in the element, and the physical dimensions of the element. The most useful oscillations are the series resonance and parallel resonances which are at 7.6 and 8.3 MHz for in one exemplary embodiment. An expected exponential lowering of the impedance of a capacitor, with increasing frequency, has deviations at these two frequencies, as energy is or is not consumed.

It has been discovered that the point spread fiction of mechanical coupling to a fingerprint ridge is offset for the parallel resonance. This concept facilitates spatial sampling frequencies of up to four times the spatial element frequency. Additionally, the sensitivity to a ridge or valley is very biased as a valley causes no transfer of energy. A ridge, however, will be insonified and a distant valley can be detected through the ridge. The net result is that the a sensor can detect valleys better than ridges and the valleys can be much smaller than the element pitch.

Attenuation/Voltage Mode

As stated above, device 1200 can also operate in an attenuation or voltage mode to obtain the fingerprint of finger 1702. This mode of operation is available whether sensor array 1220 is a piezo ceramic array (e.g., array 700) or a piezo film array (e.g., array 750). The attenuation mode of device 1200 is based on the principle that energy imparted to an element 200 loaded by a fingerprint ridge 1704 can be transferred to finger 1702, while energy imparted to an element 200 loaded by a fingerprint valley 1706 cannot be transferred to finger 1702.

In the attenuation mode, input signal generator 1202 produces a high voltage, pulsed signal that is provided to the elements of sensor array 1220 using multiplexer 1225A. FIG. 21 illustrates a one-cycle input pulse. An input signal is typically longer than one-cycle, however. In an embodiment, an input signal is about ten-cycles long. These input signal causes the elements of the array to vibrate and produce sonic waves. These sonic waves can travel from an element through the shield layer to a fingerprint ridge 1704 above the element. These sonic waves can pass into a fingerprint ridge 1704 because the acoustic impedance of the shield layer is matched to the acoustic impedance of finger 1702. No acoustic barrier to the sonic waves is formed by the interface between a fingerprint ridge 1704 and the shield layer. The energy imparted to an element loaded by a fingerprint ridge is thus dissipated. In the case of an element loaded by a fingerprint valley, the energy imparted to an element remains trapped in the element for a longer period of time. This is because the air in the fingerprint valley acts as an acoustic barrier.

Figure 22:
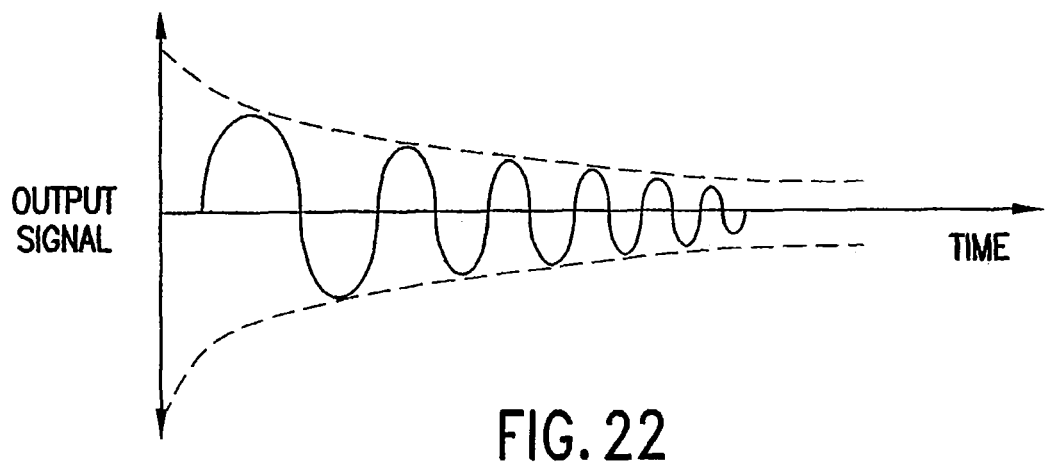
FIG. 22 illustrates a sensor array output signal according to an embodiment of the invention.

After a number of cycles, the voltages of output signals obtained for the array are determined and processed to obtain the fingerprint of finger 1702. FIG. 22 illustrates an example output signal. In an embodiment, since the energy imparted to an element loaded by a fingerprint ridge 1704 is dissipated more quickly that then energy imparted to an element loaded by a fingerprint valley 1706, the voltage of an output signal obtained from an element loaded by a fingerprint ridge 1704 is only about 1/10th of the voltage of the input signal. In this embodiment, the voltage of an output signal obtained from an element loaded by a fingerprint valley 1706 is about 1/2 of the voltage of the input signal. This difference in voltages can be detected by voltage detector 1244 and processed to generate the fingerprint of finger 1702. A means for implementing voltage detector 1244 is described above. Other means will be known to a person skilled in the relevant art.

Doppler-Shift and Echo Modes

Identification device 1200 can be operated in at least two other modes. These modes are signal time of travel (echo) mode and Doppler-shift mode. Echo mode can also be referred to as imaging mode. These modes are used to obtain biometric data such as bone maps, arteriole-veinal maps, arteriole blood flow and capillary blood flow, as described below. Combinations of these biometrics and/or others can also be obtained. For example, a ratio of arteriole blood flow to capillary blood flow can be obtained and used to indicate the emotional state or well-being of a host.

Figure 23:
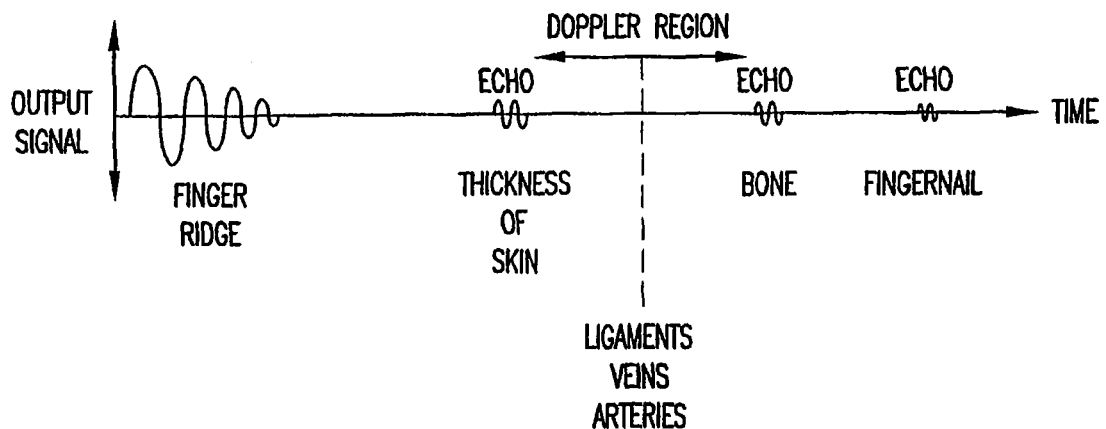
FIG. 23 illustrates how an identification device is used to obtain biometric information according to an embodiment of the invention.

FIG. 23 illustrates how an identification device 1200 operating in echo or Doppler-shift mode can be used to obtain biometric information according to embodiments of the invention. As described herein, a high voltage signal can be input to the elements of sensor array 1220 to produce sonic waves. These sonic waves travel through finger 1702 and are reflected by various features of finger 1702, such as, for example the bone of finger 1702, the fingernail of finger 1702, or the blood flowing in finger 1702.

Figure 24:
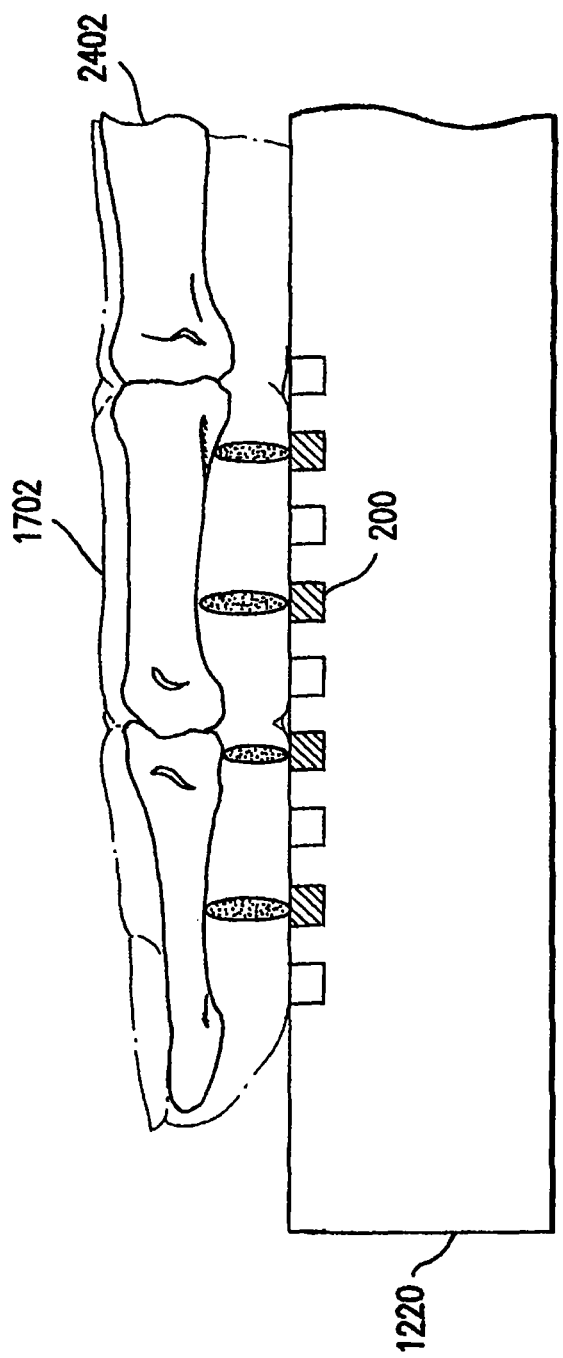
FIG. 24 illustrates how an identification device is used to obtain a bone map according to an embodiment of the invention.

FIG. 24 illustrates how an identification device 1200 is used to obtain a three-dimensional bone map according to an embodiment of the invention. To generate a map of a bone 2402 of finger 1702, device 1200 is operated in its echo mode. Sound waves traveling from the skin surface into finger 1702 will be reflected from the bone structure of bone 2402. This structure can be identified from the large echo amplitude that it causes. Since the echo travel time is a measure of the sensor to bone distance, a three-dimensional map of the shape of bone 2402 can be attained.

To obtain a map of bone 2402, a high voltage, pulsed input signal is generated by input signal generator 1202 and provided to the elements of array 1220. This input signal causes the elements to generate sonic waves that travel into finger 1702. As shown in FIG. 24, only certain elements 200 of array 1220 are actively generating sonic waves at any given time. In accordance with the invention, and as described herein, active sonic wave transmitting and receiving apertures are configured and moved (scanned) across sensor array 1220 using controller 1230 and multiplexers 1225. The generated sonic waves travel through finger 1702 and are reflected by the structure of bone 2402. These reflected sonic waves are then detected by the receiving apertures. The time of travel of the sonic waves are obtained by detector 1246 of device 1200 and used to detect whether bone structure is located at a various distances from array 1220. As would be known to a person skilled in the relevant art, this mode of operation is similar to how radars operate.

Figure 25:
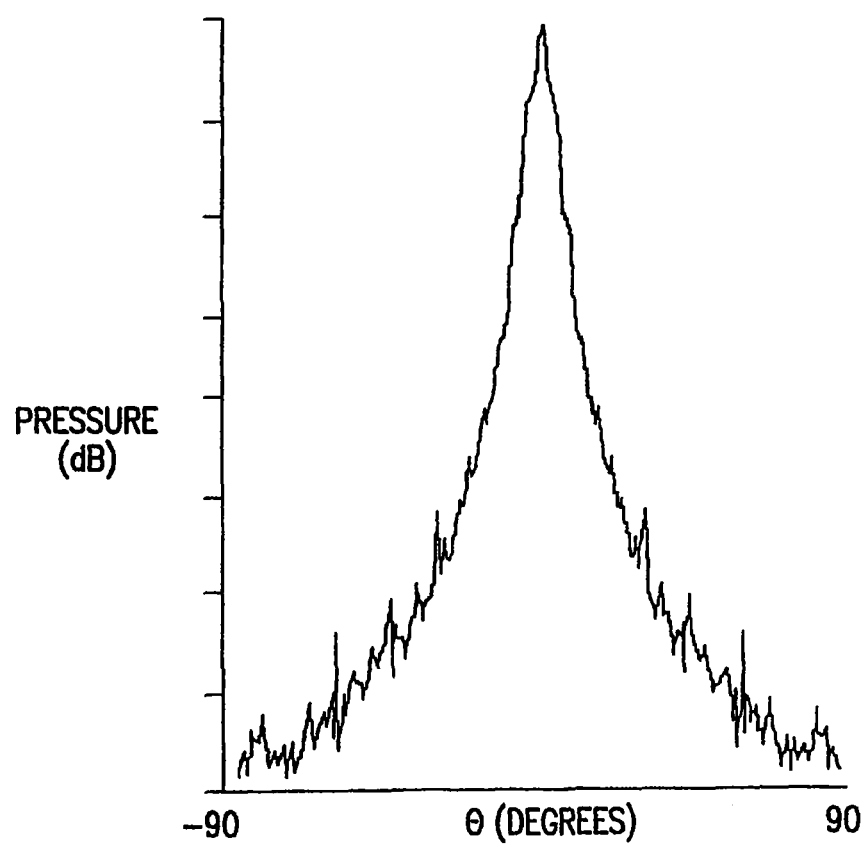
FIG. 25 illustrates a transmitting and/or receiving beam directivity according to an embodiment of the invention.

The wavelength of the sonic waves and the aperture selected define the transmit and receive beam shape. Various aperture sizes and beam directivity can be formed in accordance with the invention. FIG. 25 illustrates a example beam directivity that can be used to obtain a bone map of bone 2402 according to an embodiment of the invention. Other beams can also be used.

Figure 26:
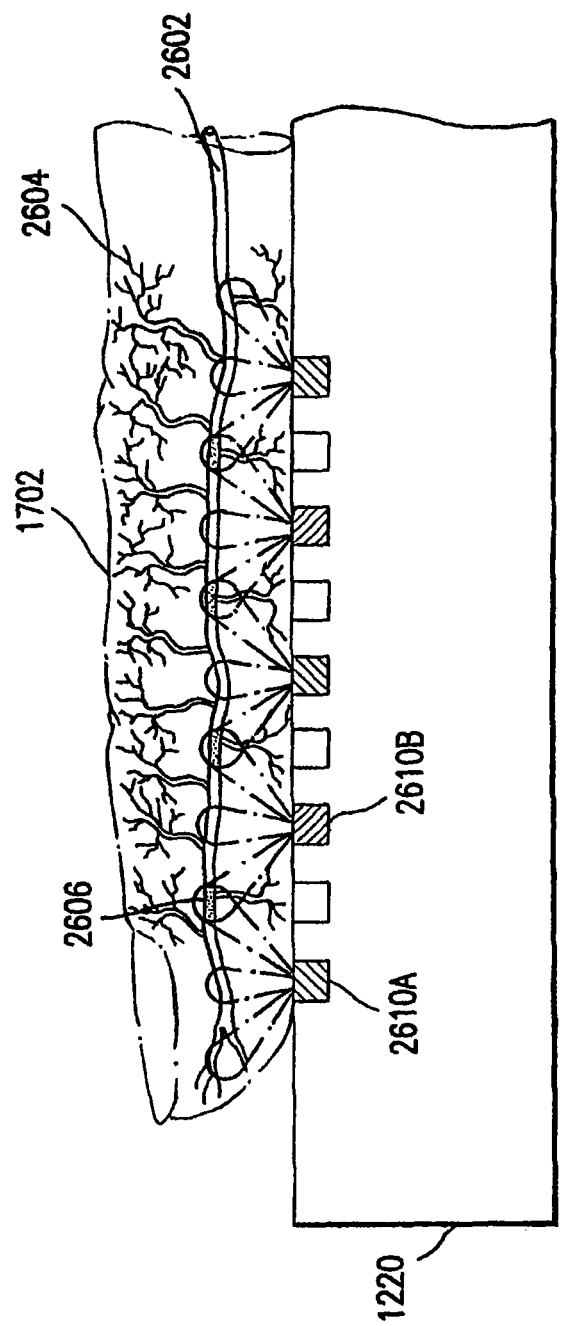
FIG. 26 illustrates how an identification device is used to obtain arteriole blood flow information according to an embodiment of the invention.

FIG. 26 illustrates how identification device 1200 is used to obtain arteriole blood flow information according to an embodiment of the invention. An artery 2602 and capillaries 2604 are shown for finger 1702. As seen in FIG. 26, arteriole blood flow is parallel to the surface of sensory array 1220.

Arteriole blood flow data is obtained from device 1200 while it is operating in Doppler-shift mode. To receive a Doppler-shift signal back-scattered from red blood cells flowing in artery 2602, the transmit and receive directivity beam patterns of sensor array 1220 must form one or more overlapping volumes 2606.

Figure 27:
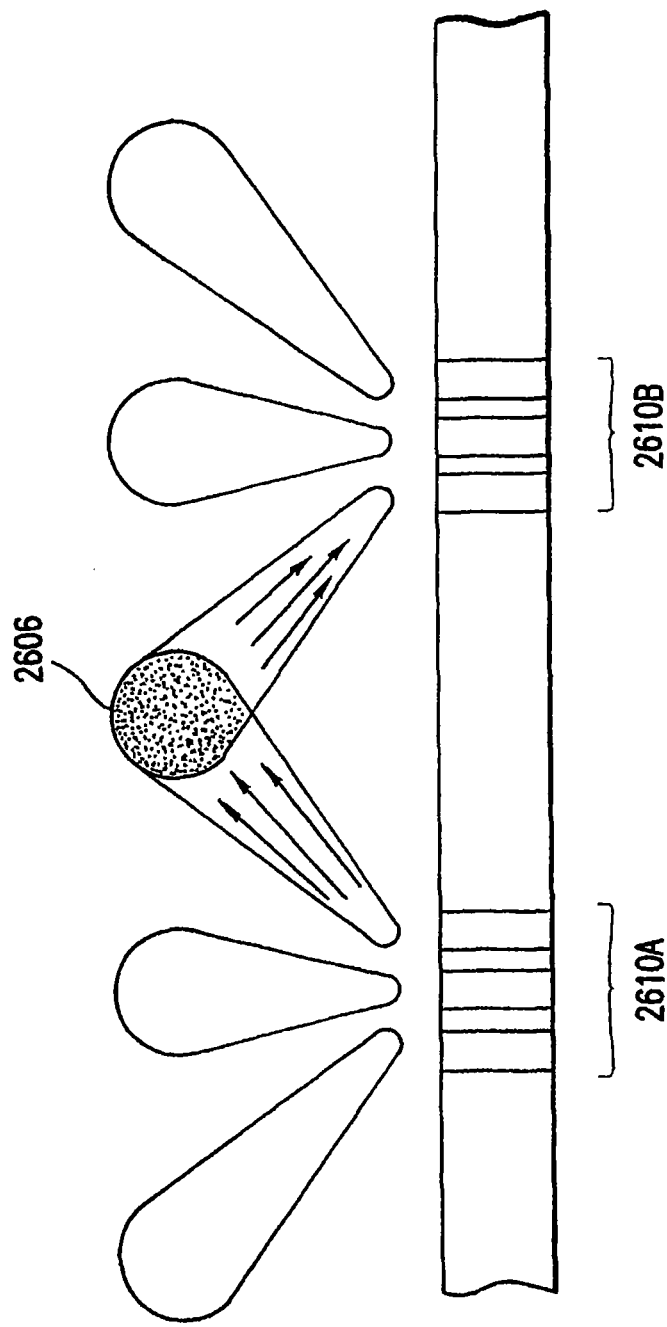
FIG. 27 illustrates a transmitting beam directivity and a receiving beam directivity according to an embodiment of the invention.
Figure 28:
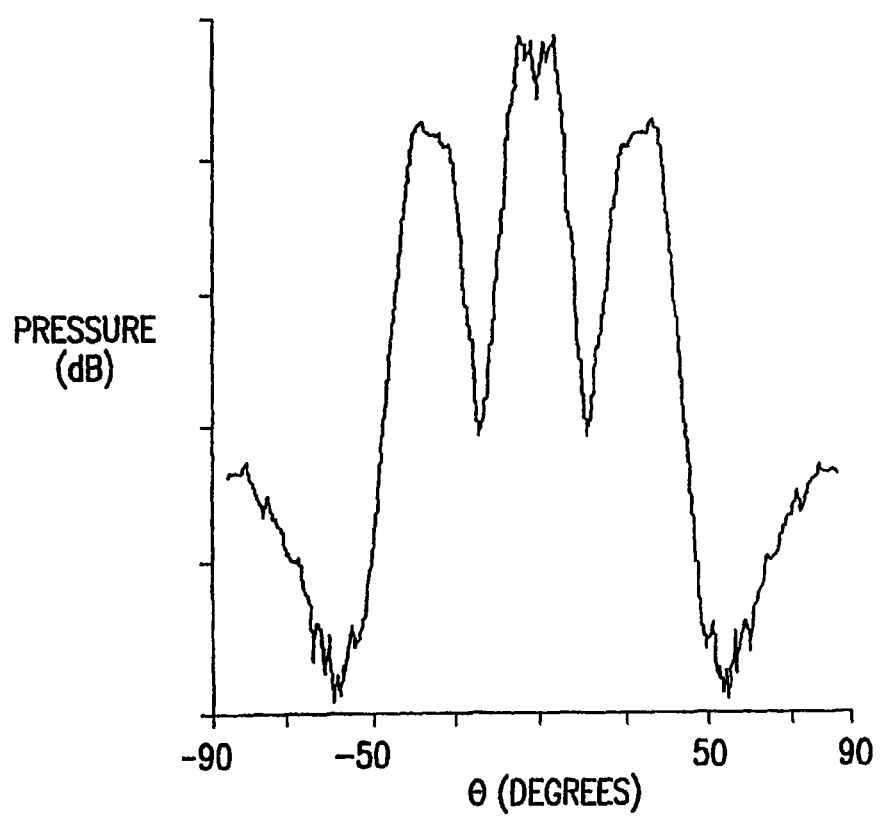
FIG. 28 illustrates a transmitting and/or receiving beam directivity according to an embodiment of the invention.

FIG. 27 illustrates a transmitting aperture 2610A and a receiving aperture 2610B according to an embodiment of the invention that form an overlapping volume 2606. One approach for creating transmitting apertures 2610A and receiving apertures 2610B is to make the apertures less than about six wavelengths square (e.g., 300 microns or six elements on a side) and spaced at a pitch of two wavelengths (600 microns). These apertures create side beams or grating lobes at about 30 degrees and form overlapping regions 2606 at a depth appropriate for detecting arteriole blood flow. FIG. 28 illustrates a transmitting and/or receiving beam formed by such apertures according to an embodiment of the invention. Other apertures can also be used. The angle at which grating lobes can be created are controlled by the ratio of the pitch between apertures and the wavelength of the sonic waves generated, as would be known to a person skilled in the relevant art given the description of the invention herein.

As seen in FIGS. 26 and 27, sonic energy produced by aperture 2610A is scattered by blood cells flowing in artery 2602 and received at aperture 2610B. The input signal provided to the elements of array 1220 that make up aperture 2610A is a high voltage, continuous wave signal. This input signal is also provided to output signal processor 1240 as a reference signal for Doppler-shift detector 1248. This input or reference signal is mixed by Doppler-shift detector 1248 with the output signal received from aperture 2610B to obtain Doppler-shift information. Circuits for implementing Doppler-shift detector 1248 are known in the relevant art, and thus not reproduced here.

Figure 29:
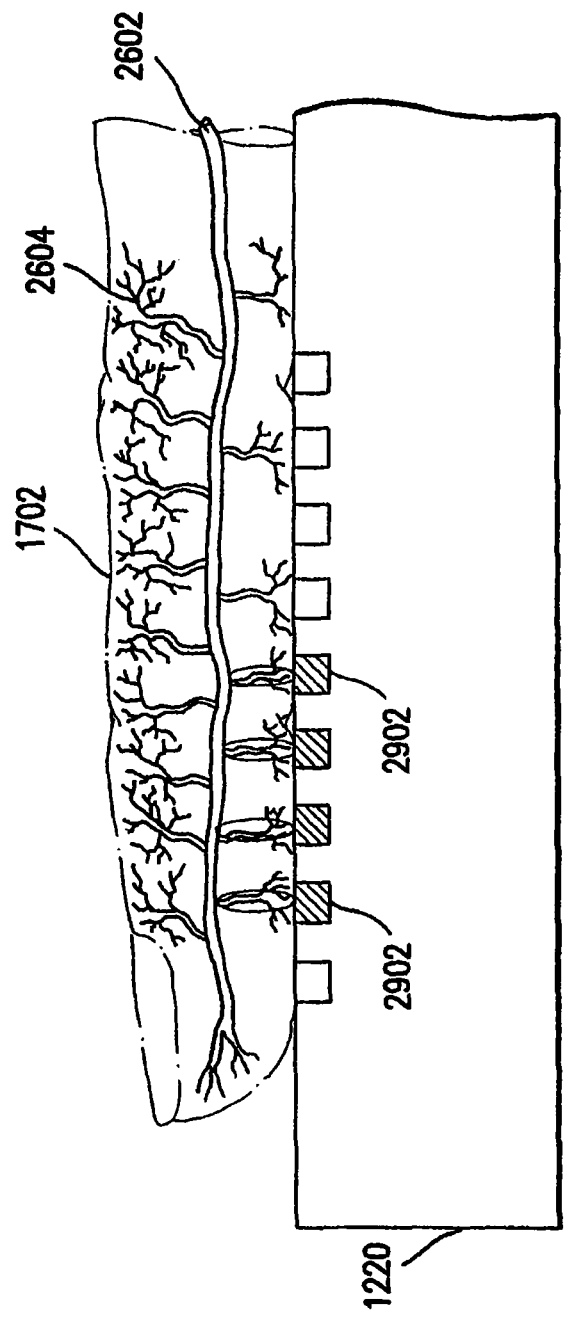
FIG. 29 illustrates how an identification device is used to obtain capillary blood flow information according to an embodiment of the invention.
Figure 30:
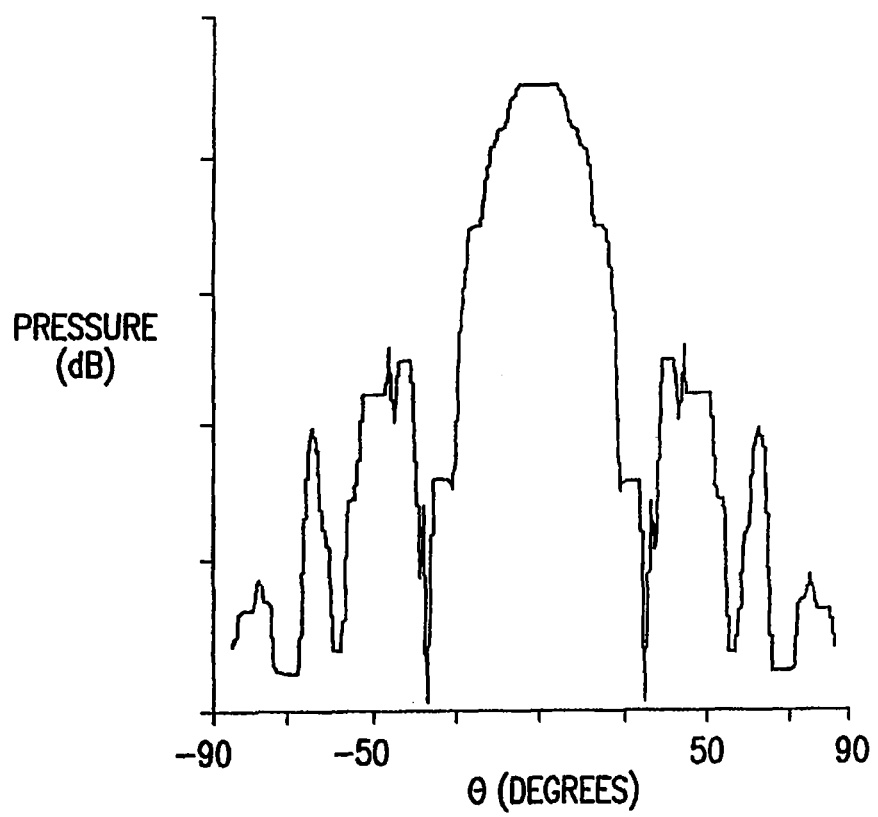
FIG. 30 illustrates a transmitting and/or receiving beam directivity according to an embodiment of the invention.

FIG. 29 illustrates how an identification device 1200 is used to obtain capillary blood flow information according to an embodiment of the invention. As seen in FIG. 29, capillary blood flow is in a direction normal to the surface of sensor array 1220. To separate the capillary flow from the arteriole flow, multiple apertures of nine elements (3.times.3, 150 micron square) can be selected. This aperture will create a very small and close area of sensitivity that can be replicated in many parts of sensor 1220 simultaneously. The sensitivity of the apertures can be increased by adding the Doppler signals of multiple apertures together. The sensitivity apertures is focused in the first half millimeter of finger 1702 closest to the surface of array 1220. FIG. 30 illustrates a transmitting and/or receiving beam directivity that can be used to detect capillary blood flow according to an embodiment of the invention.

When using device 1200 to detect blood flow, using a pulsed Doppler embodiment has the advantage of having the same aperture perform both the transmit and receive functions. In addition, by gating the received signal, only backscattered information resulting from a well-defined sample volume is analyzed to obtain the blood flow pattern.

Figure 31:
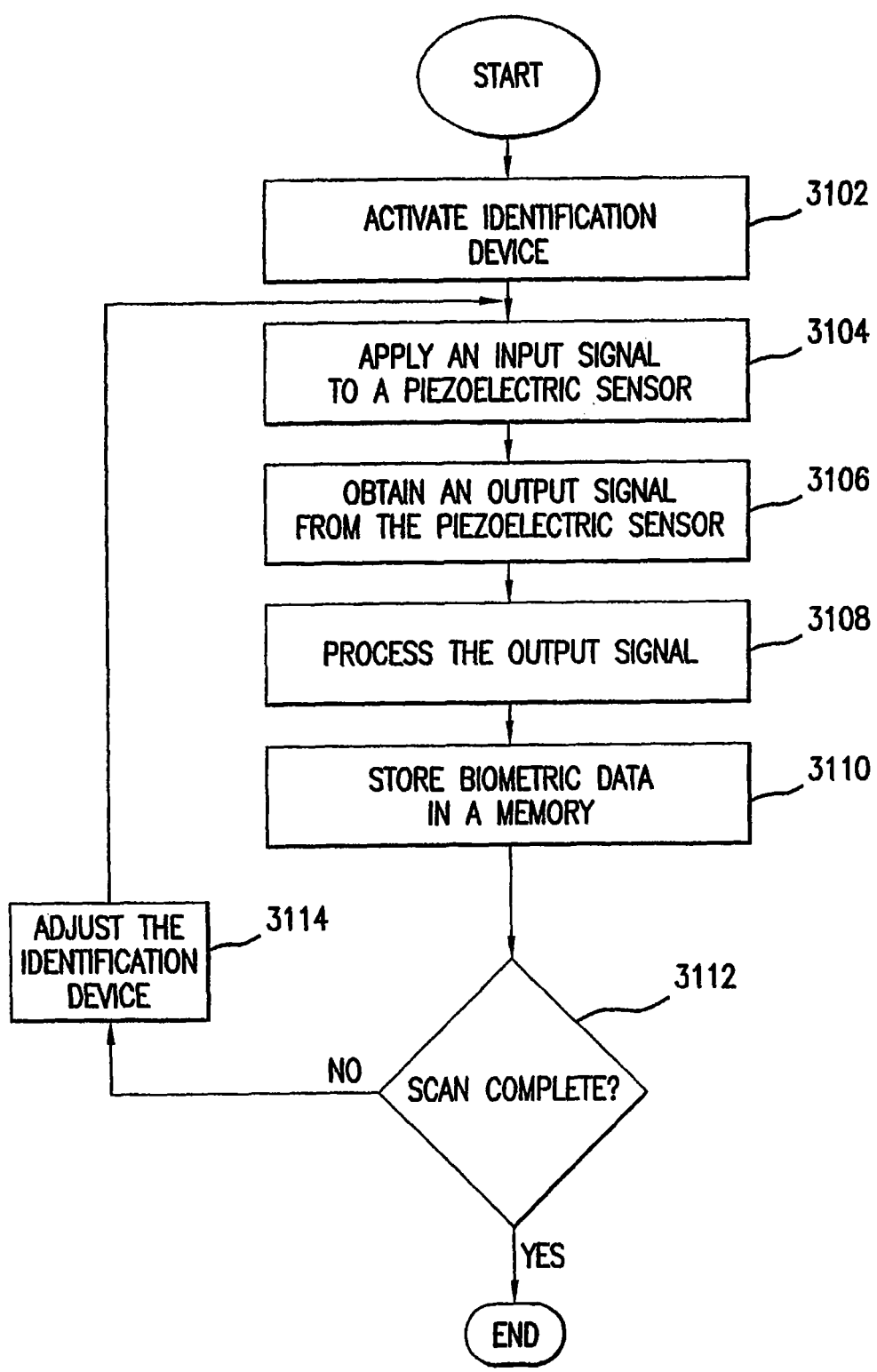
FIG. 31 is a flowchart of a method according to an embodiment of the invention.

FIG. 31 is a flowchart of a more detailed method 3100 for obtaining biometric data using device 1200. Method 3100 is described with reference to a particular embodiment of device 1200 having a piezo film sensor array.

In step 3102, device 1200 is awakened and piezo film sensor array 1220 is switched to detect an initial pixel or a group of pixels. Controller 1230 switches multiplexers 1225A and 1225B to a designated initial pixel or group of pixels. In one example, piezo film sensor array 1220 is a 512.times.512 pixel array. Multiplexers 1225A and 1225B are each used to addressed and/or select a particular grid line (conductor) at a designated address of the initial pixel or group of pixels being detected.

In step 3104, an input signal is applied to piezo film array 1220. A pulse is applied in one 30 MHZ cycle. Oscillator 1204 generates an oscillation signal at 30 MHZ. Multiplexer 1225A forwards the input pulse to an initial pixel or group of pixels. This input signal is also sent to controller 1230 and output signal processor 1240.

In step 3106, an output signal is obtained from piezo film array 1220. Output signal processor 1240 waits a number of cycles before detecting a signal at the pixel. For example, in response to the signal sent from input signal generator 1202, output signal processor 1240 waits a number of cycles after the input pulse is applied to the pixel (or group of pixels). In step 3108, when the wait is complete, a voltage, for example, is evaluated using voltage detector 1244.

For example, one 30 MHZ cycle corresponds to approximately 33 nanoseconds. The wait can be approximately 5 cycles or 150 nanoseconds. Other wait durations (e.g. a greater or smaller number of periods) can be used depending upon the oscillator frequency and/or other design considerations. This wait allows the ring down oscillation due to the presence of a fingerprint ridge to occur, in response to the applied electrical pulse at the pixel, as described above.

In step 3108, a filtered voltage is evaluated by output signal processor 1240 and a grey scale or a binary pixel value is output representative of the detected voltage (step 3110). A filter circuit (not shown) is a band-pass filter that filters the output voltage to detect an output voltage signal in a passband centered about a frequency of approximately 30 MHz. The grey scale or binary pixel value is output to memory controller 1260 for storage in image memory 1270. In one example, the output grey scale or binary pixel value is stored in an address in image memory 1270 that corresponds to the detected pixel.

In step 3112, a check is made to determine if the scan is complete. In other words, a check is made to determine whether each pixel in the 500.times.400 sensor array 1220 has been scanned and a corresponding output value has been stored and accumulated in image memory 1270. If the scan is complete, then the routine ends. A signal or other indication can then be generated and output from device 1200 to indicate, for example, that a fingerprint image has been successfully captured. If the scan is not complete, then the piezo film sensor array 1220 is switched to detect the next pixel or next group of pixels (step 3114). Control then returns to perform steps 3104 through 3112 at the next pixel or next group of pixels.

As described above, piezo film sensor array 1220 can be switched by multiplexers 1225 to detect voltage values at a single pixel or a group of pixels. In general, any pattern for scanning pixels can be used. For example, a raster scan of pixels can be performed. Pixels can be scanned row by row or column by column.

In one preferred example, when multiple groups of pixels are read out at a given instant, each pixel in a group of pixels are separated by a predetermined distance. In this way interfering effects from the ring down oscillation in neighboring pixels are minimized or avoided. In one example, pixels detected in a given cycle are separated by a minimum distance of at least 8 pixels. In this way any ring down oscillations between neighboring pixels are attenuated significantly.

Example Applications of the Invention

Biometric Capture Device

Figure 32:
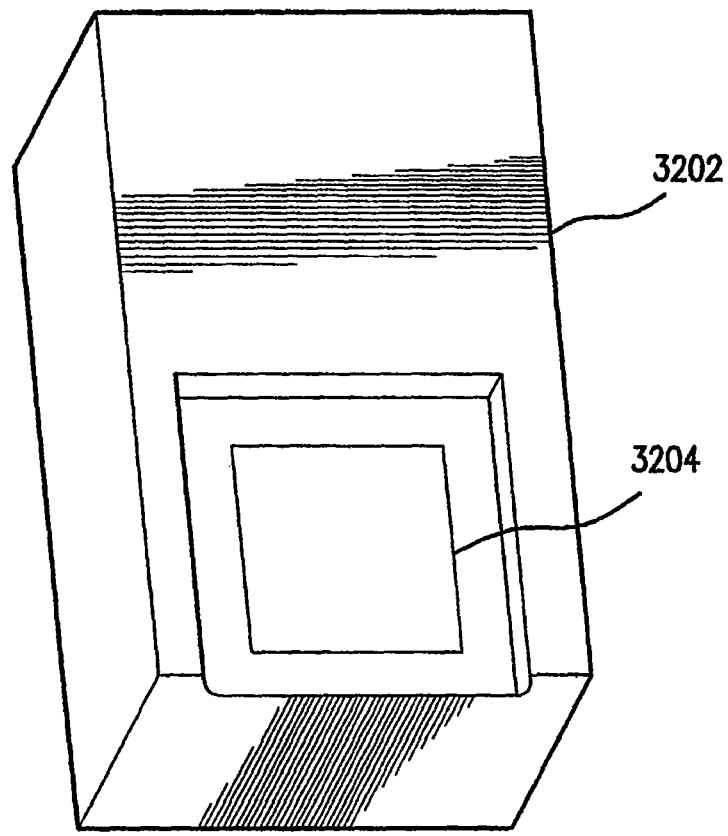
FIG. 32 illustrates a biometric device according to an embodiment of the invention.

FIG. 32 illustrates a biometric device 3202 according to an embodiment of the invention. Device 3202 has a sensor array 3204 according to the invention. Device 3202 is particularly adapted for obtaining and storing fingerprint data according to the invention. Device 3202 is intended, for example, to be used by law enforcement personnel.

Mobile Biometric Capture Device

Figure 33:
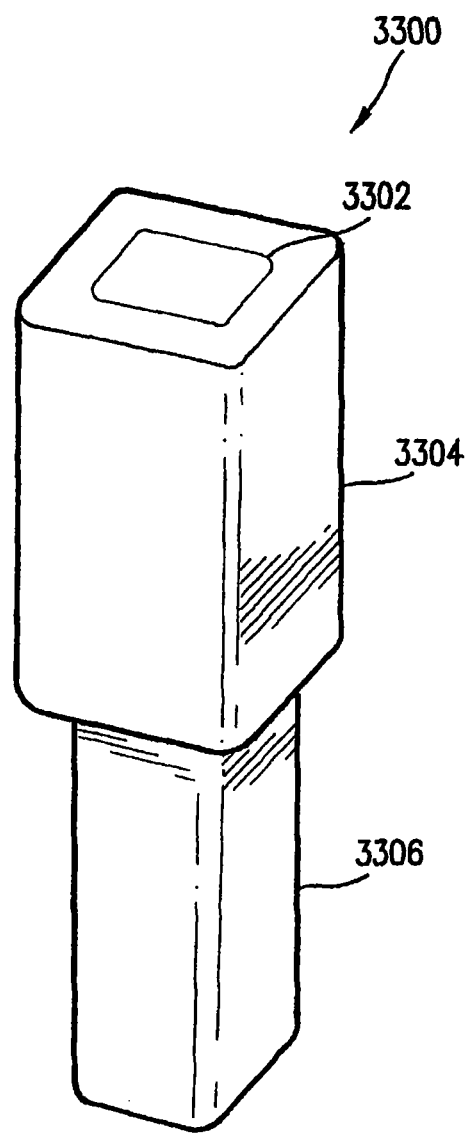
FIG. 33 illustrates a mobile biometric device according to an embodiment of the invention.

FIG. 33 illustrates a mobile biometric device 3300 according to an embodiment of the invention. Device 3300 has a sensor array 3302 according to the invention at one end of the device, and a handle 3306 at an opposite end. The circuitry of the device is located in a portion 3304 of the device. Device 3300 is battery operated. Device 3300 is also intended, for example, to be used by law enforcement personnel.

Wireless Transceiver Biometric Device

Figure 34:
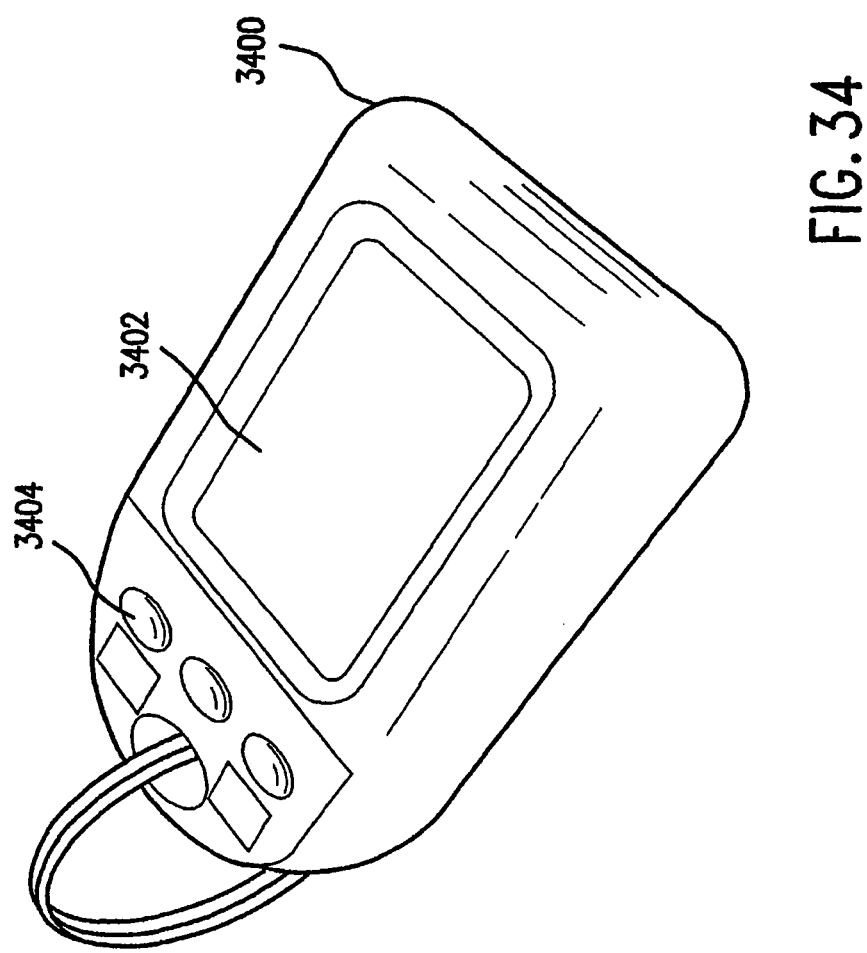
FIG. 34 illustrates a wireless transceiver biometric device according to an embodiment of the invention.

FIG. 34 illustrates a wireless transceiver biometric device 3400 according to an embodiment of the invention. Device 3400 is intended to be used by the general populace, for example, as an electronic signature device.

Device 3400 has a sensor 3402 for obtaining biometric data, such as a fingerprint, according to the invention. Device 3400 is shown as having three indicator lights 3404 for communication information to a user.

Figure 35:
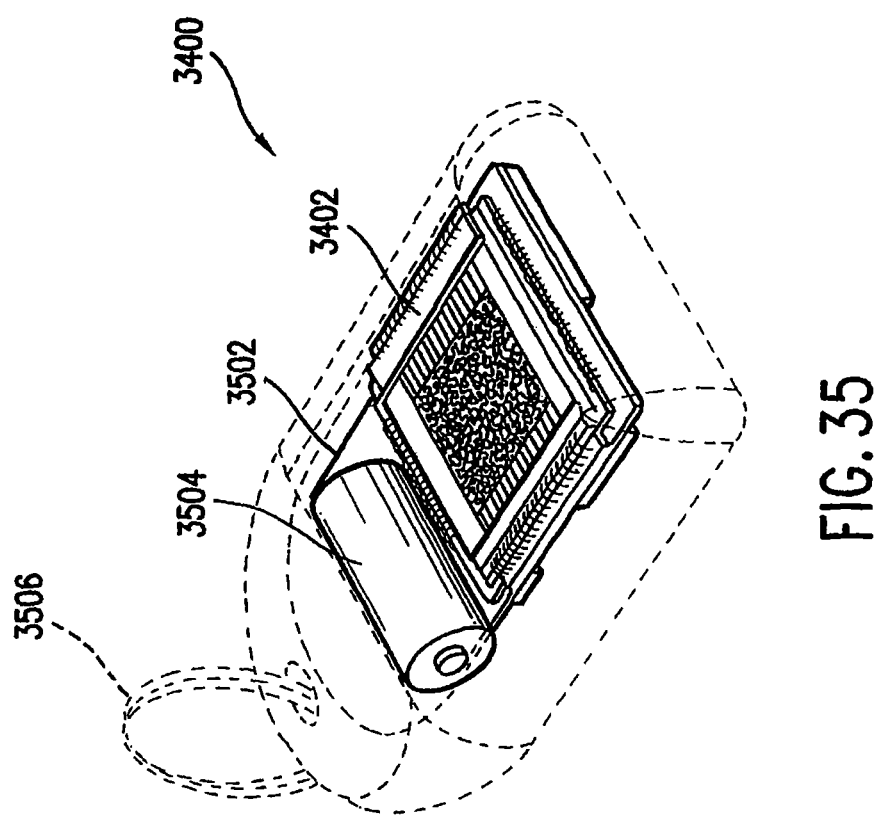
FIG. 35 illustrates a more detailed view of the wireless transceiver biometric device of FIG. 34.
Figure 36:
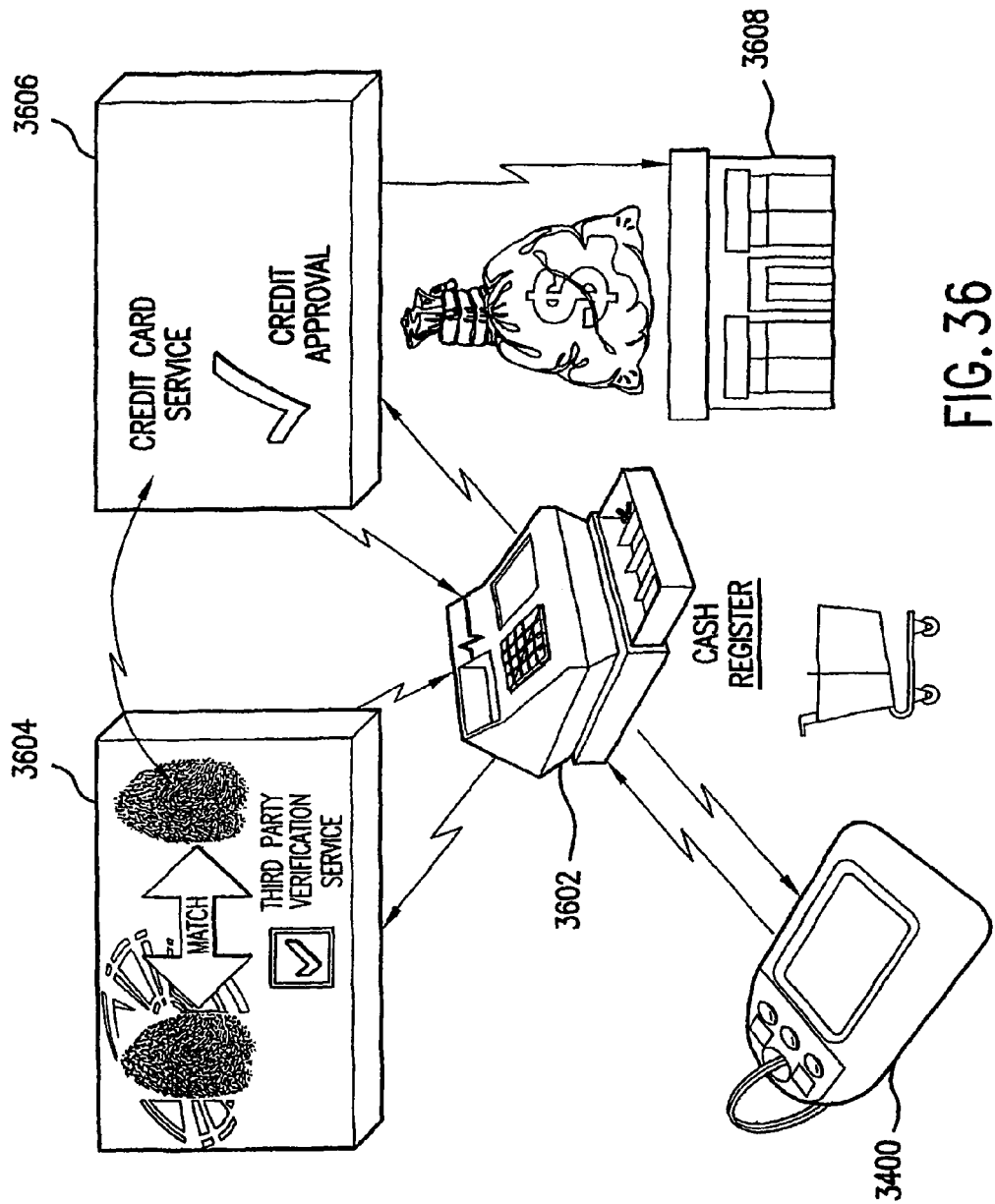
FIG. 36 illustrates using the wireless transceiver biometric device of FIG. 34 to complete an electronic sales transaction.
Figure 37:
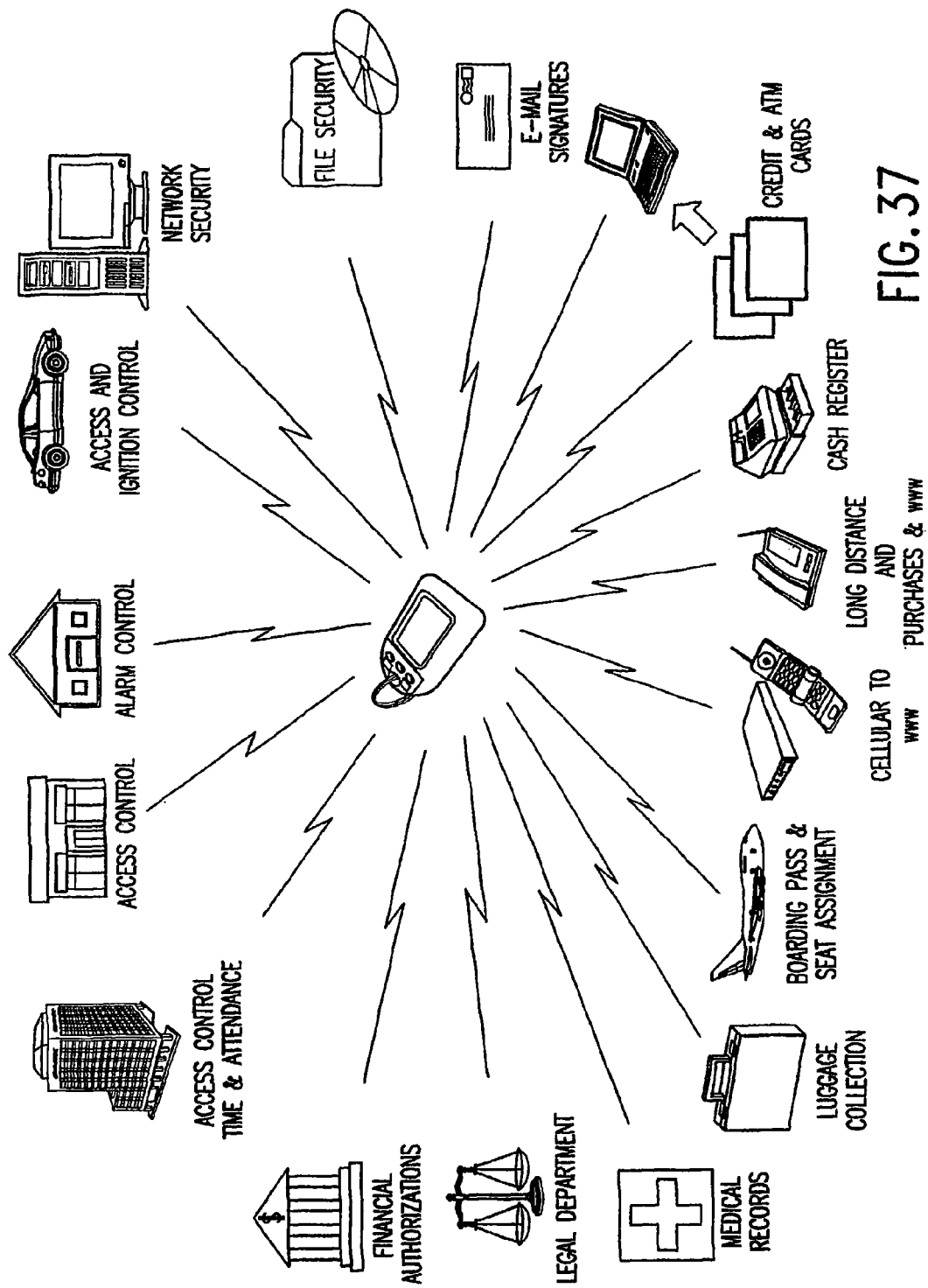
FIG. 37 illustrates various applications for the wireless transceiver biometric device of FIG. 34.

FIG. 35 illustrates a more detailed view of the wireless transceiver biometric device 3400. As can be seen in FIG. 35, sensor 3402 is powered by a battery 3504. Device 3400 has an antenna 3502 that can be used for sending information to and receiving information from other device. Device 3400 can be made to be compatible with BLUETOOTH wireless technology. A key ring 3506 can be attached to device 3400. As illustrated by FIGS. 36 and 37, device 3400 has a multitude of possible uses.

Electronic Sales and/or Transactions

FIG. 36 illustrates using the wireless transceiver biometric device 3400 to complete an electronic sales transaction. In step 1 of the transaction, device 3400 is used to obtain a fingerprint of the individual wanting to make a purchase. Device 3400 then transmits the fingerprint to a device coupled to cash register 3602 (step 2), which sends the fingerprint to a third party verification service 3604 (step 3). The third party verification service uses the received fingerprint to verify the identity of the purchaser (step 4) by matching the received fingerprint to fingerprint data stored in a database. The identity of the purchaser can then be sent to cash register 3602 (step 5) and to a credit card service 3606 (step 6). The credit card service uses the data from the third party verification service to approve sales information received from cash register 3602 (step 7) and to prevent the unauthorized use of a credit card. Once cash register 3602 receive verification of the purchaser's identity and verification that the purchaser is authorized to use the credit card service, cash register 3602 can notify device 3400 to send a credit card number (step 8). Cash register 3602 can then send the credit card number to the credit card service 3606 (step 9), which then transfers money to the sellers bank account (step 10) to complete the sales transactions. These steps are illustrative of how device 3400 can be used as an electronic signature device, and are not intended to limit the present invention.

Other Wireless Transceiver Biometric Device Applications

FIG. 37 illustrates other applications for which the wireless transceiver biometric device 3400 is well suited. For example, device 3400 can be used for: building access control; law enforcement; electronic commerce; financial transaction security; tracking employee time and attendance; controlling access to legal, personnel, and/or medical records; transportation security; e-mail signatures; controlling use of credit cards and ATM cards; file security; computer network security; alarm control; and identification, recognition, and verification of individuals. These are just a few of the many useful application of device 3400 in particular, and the present invention in general. Additional applications for device 3400 and the invention will be apparent to those skilled in the relevant arts given the description of the invention herein.

Personal Area Network Applications

Figure 38:
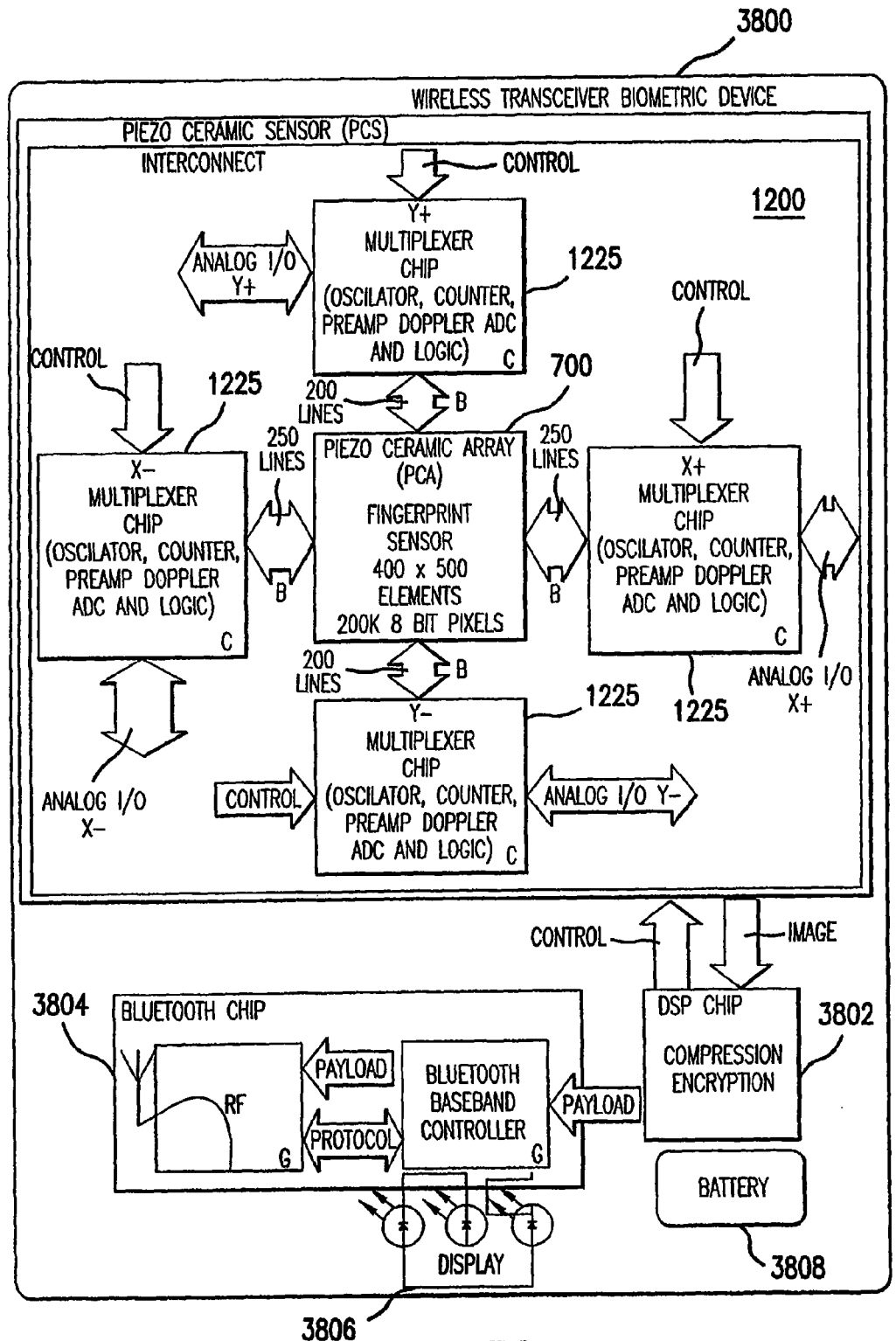
FIG. 38 illustrates a wireless transceiver biometric device according to an embodiment of the invention.

As described herein, embodiments of the invention are capable of interacting with other devices as part of a personal area network. FIG. 38 illustrates one embodiment of a wireless transceiver biometric device 3800 according to the invention. Device 3800 comprises a biometric device similar to device 1200, described above, a DSP chip 3802, a BLUETOOTH chip 3804, a display 3806, and a battery 3808. As described above, device 1200 has a piezo ceramic sensor array 700 and four multiplexers 1225 according to the invention.

Biometric device 1200 is coupled to a DSP 3802. DSP 3802 controls device 1200 and stores biometric data. DSP 3802 is also coupled to BLUETOOTH chip 3804 for sending and receiving data. A display 3806 is used to communicate information to a user of device 3800. Device 3800 is powered by a battery 3808. As would be known to a person skilled in the relevant art, BLUETOOTH is an agreement that governs the protocols and hardware for a short-range wireless communications technology. The invention is not limited to implementing only the BLUETOOTH technology. Other wireless protocols and hardware can also be used.

Wireless transceiver biometric device 3800 enables an individual to be in communication with compatible devices within about 30 feet of device 3800. Device 3800 can connect, for example, with to telephones, cell phones, personal computers, printers, gas pumps, cash registers, Automated teller machines, door locks, automobiles, et cetera. Because device 3800 can connect to and exchange information or data with any compatible device within a personal area network, or piconet, device 3800 is able to supply a standardized secure identification or authorization token to any device, or for any process or transaction that needs or requests it.

Public Service Layer Applications

The present invention provides a "public services layer" (PSL) high up in a BLUETOOTH stack. The PSL layer rationalizes identification and access control for BLUETOOTH devices communicatively coupled to each other. In embodiments, the PSL layer supports authorization and identification based on a fingerprint biometric signal provided by a fingerprint scanner. In one example, a wireless transceiver biometric device 3800 can be used with a BLUETOOTH module including a BLUETOOTH protocol stack to provide the fingerprint biometric signal. See, e.g., the description of BLUETOOTH module, protocol stack, and compliant devices by Jennifer Bray and Charles Sturman, Bluetooth™. Connect without Cables, Prentice-Hall, Upper Saddle River, N.J. 2001 (entire book incorporated in its entirety herein by reference), and Brent Miller and Chatschik Bisdikian, Bluetooth Revealed, Prentice-Hall, Upper Saddle River, N.J. 2001 (entire book incorporated in its entirety herein by reference).

In embodiments, the PSL layer functionality is defined by a protocol (also called a specification). The PSL layer interprets simple requests from devices in the piconet and acknowledges back with capabilities and level of capability in a predefined form. Vendors of BLUETOOTH appliances can add services in the PSL layer of the present invention to enhance the features of their product.

The PSL layer, which would in most cases act transparently to the normal function of the device until a PSL request was broadcast that requested one of the functionality groups that the device supported. One minimum level of support re-broadcasts an unsatisfied request in the aid of extending the scatter net to eventually find a device with the requested function. In this way, other devices outside of the range of a requesting device can be contacted to fulfill the PSL request.

Figure 39:
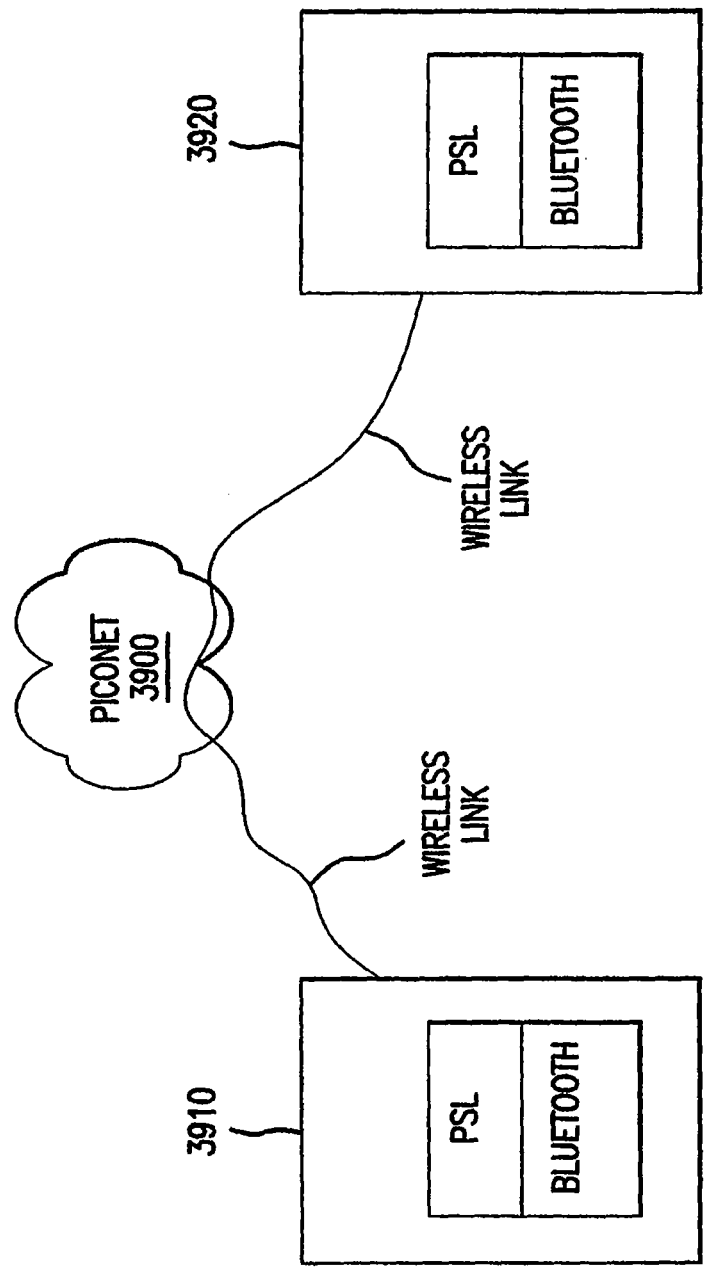
FIG. 39 is a diagram of an example piconet having coupling BLUETOOTH devices with a public service layer. Not applicable.

FIG. 39 is a diagram of an example piconet 3900 coupling BLUETOOTH devices 3910, 39200 according to the present invention. Device BLUETOOTH is a fingerprint scanner with a public service layer and BLUETOOTH stack or chipset. The public service layer can support authorization and identification. Device 3920 is any BLUETOOTH appliance. Device 3920 includes a PSL layer and BLUETOOTH stack or chipset. Piconet 3900 can include any number of BLUETOOTH devices within the area of the piconet, within a scattemet, or coupled to the piconet through other communication links.

Completing a task may require many functions to be performed in concert among a constellation of distributed BLUETOOTH appliances. The user would have to purchase and install sufficient appliances to cover all the functions in a task. The PSL scheme enables efficiency and cost savings as the appliances would be shared amongst users and in some cases providing multiple uses.

One example operation of the PSL layer is physical access control. A PSL layer of wireless transceiver biometric device 3920 sends or broadcasts one or more request access signals. Such request access signals in the PSL layer can include a request for extract/match/access and data representative of detected fingerprint from outside the secured perimeter via BLUETOOTH. The PSL layer in a Desktop PC with BLUETOOTH inside the secured area receives the request from the wireless transceiver biometric device 3920 for extract/match/access and matches the print data to the personnel database which could be stored in a server and sends an access granted to the door. The BLUETOOTH door lock then opens and the task is completed.

The savings are illustrated by: using a desktop PC that is used for other purposes, to perform the function of access control, time and attendance, personnel tracking and security. The only dedicated hardware is the BLUETOOTH door lock as the PC and the wireless transceiver biometric device 3800 are used for other tasks. The installation cost is minimal and the convenience of record keeping and data base management is also minimal. The three appliances involved in this task could be purchased from different vendors who have only communicated to the PSL standard. The function of fingerprint extract/match/access could be pattern, minutiae, local or central or even changed at any time for greater security and convenience etc, without effecting the door lock or wireless transceiver biometric devices 3800. The turning off or on of say lights, air conditioners, telephones, could all be added to this task if desired.

Another advantage in savings is obsolescence. A building fitted with BLUETOOTH door locks, BLUETOOTH air-conditioning, BLUETOOTH smoke detectors, BLUETOOTH lighting etc. could be upgraded with biometric controls without installation costs.

Appliances such a smoke alarms and light fixtures can act as alarms and extend piconets into scatter nets that will bridge gaps in parks, gardens and car parks adding security and functionality to gates in remote areas.

Telephones could be marketed with BLUETOOTH PSL functionality meaning that they can dial 911 if an emergency code is received. BLUETOOTH PSL could signify functionality to be programmed to dial a specific number for private emergency services.

Protocols could be defined which log events in a FIFO so false alarms could be traced and minimized.

In one embodiment, the PSL Specification has the elements identified below.

A decimal filing system is included. A request is broadcast for a function that can be as specific as the number of decimal places in the request. In this way a manufacturer can keep the task in his constellation of devices if the devices are available as is expected. If the request is not serviced by the exact function number (FN) required the next nearest FN in the scatter net is used. Clusters of FN are used around areas of development. For example, a light fixture can have a FN of 551.263, which indicates 500 a facility utility, 550 a light, 551 a plug in, 551.2 a table lamp, 551.26 a halogen low voltage, 551.263 made by a person or company (not exclusive). A request for this specific function of turning on 551.263 may be serviced by 557.789 a wall neon as that is all that is available at the time and the numerically nearest number though limited to the group of 55X lighting. The FN 551.26 can be defined in the PSL specification, digits after this are for manufactures uses and may be registered. In this way a lighting manufacturer may supply software for a PC that orchestrates visual effects.

A requesting device or a PSL manager (Piconet Master Device) could arbitrate in the scatter net to match requests and functions.

The PSL can also define the structure of how functions are allocated. A FN allows one to negotiate with vendors of door locks with minimal effort. The PSL also gives manufacturers of other appliances insight into task implementation where a wireless transceiver biometric device 3800 could play key roles.

Function Numbers in the PSL are grouped for request and function suitability in one example as:

100 Emergency
200 Communications
300 Security
400 Positional
500 Facilities and Utilities
600 Entertainment
700 Computation and Information
800 Transportation
900 Miscellaneous Sub-functional Groups are defined in one example as follows:

210 Internet connection (for transfer of credentials to local DB)
310 Personal identification via PIN
311 Personal identification via Signature
312 Personal identification via Fingerprint
313 Personal identification via Voice
314 Personal identification via Face
315 Personal identification via Eye
342 Fingerprint Feature Extraction Matching
520 Door Locks
550 Lighting Requests and Events can also be used in the PSL specification.

Off/ON/More/Less are universal requests. User specific requests would not be in the specification. Events such as ACK, NAC, can also be added in the PSL specification.

Protocols or the structure of the request and acknowledgment include the following features broadcasted in a packet.

(a) PSL indicates this packet is a PSL function request.
(b) FUNCTION NUMBER indicates the function requested
(c) REQUE indicates the operation to be performed (off/on, lock/unlock)
(d) KEYS authenticates rights of the packet. (e) PAYLOAD data if applicable The PSL specification can but does not need to repeat the BLUETOOTH structure of encryption, error checking et cetera.

The following series of examples serve to illustrate the PSL layer in several real-world applications:

Help I have fallen and I can't get up.
  a) I press my BLUETOOTH alert button and emergency services are requested.
  b) A PC in the scatter net connects to the world wide web and executes a call to a contracting service supplier (a level one (preferred level) BLUETOOTH service) or in addition to or upon a failure the next level occurs.
  c) A telephone with BLUETOOTH calls 911 or a service provider with a recorded message (a level two BLUETOOTH service) or upon a failure the next level occurs.
  d) A fire alarm with BLUETOOTH activates (a level three non preferred but applicable BLUETOOTH service) or upon a failure the next level occurs.
  e) A smoke detector activates is audio alarm in the hopes of attracting attention (a level four non preferred but applicable BLUETOOTH service)
  f) An Automobile within the scatter net activates its horn and flashes its lights to alert personnel to an emergency situation. (a level five non preferred but applicable BLUETOOTH service)

I would like access to my office
  a) I press my wireless transceiver biometric device 3800 wireless transceiver biometric device 3800.
  b) The wireless transceiver biometric device 3800 requests and negotiates fingerprint identification function from a PC with BLUETOOTH connected to the server in the office.
  c) The server then authorized the door lock with BLUETOOTH to be unlatched.

I would like to get through an airport
  a) Baggage check in via kiosk with non reputable ID
  b) Seat allocation and gate pass with ID at kiosk
  c) Baggage claim with ID Television programs could broadcast to BLUETOOTH TV that will add effects to a BLUETOOTH home to assist future versions of Friday the 13th.

I would like to make a sizable trade on margin.
  a) I verify my identity via wireless transceiver biometric device 3800 to my PC
  b) The PC requests additional GPS location for the log of the trade verification.

Other example uses will be apparent to a person skilled in the relevant art given the description of the invention herein. The public service layer according to the present invention can be used with any wireless transceiver biometric device including any type of fingerprint scanner. For example, fingerprint scanners which can be used include, but are not limited to, silicon-based fingerprint scanners, optical fingerprint scanners, piezoelectric fingerprint scanners, piezo-film fingerprint scanners and piezo-ceramic fingerprint scanners.

Fingerprint Sensor Using Acoustic Impediography

There are several different types of Fingerprint sensor electrical system on the market: optical, capacitive, RF, thermal, and Infra-red (amongst others). This patent describes an electrical system for a new fingerprint sensor technology based on the principle of Acoustic Impediography.

Figure 40:
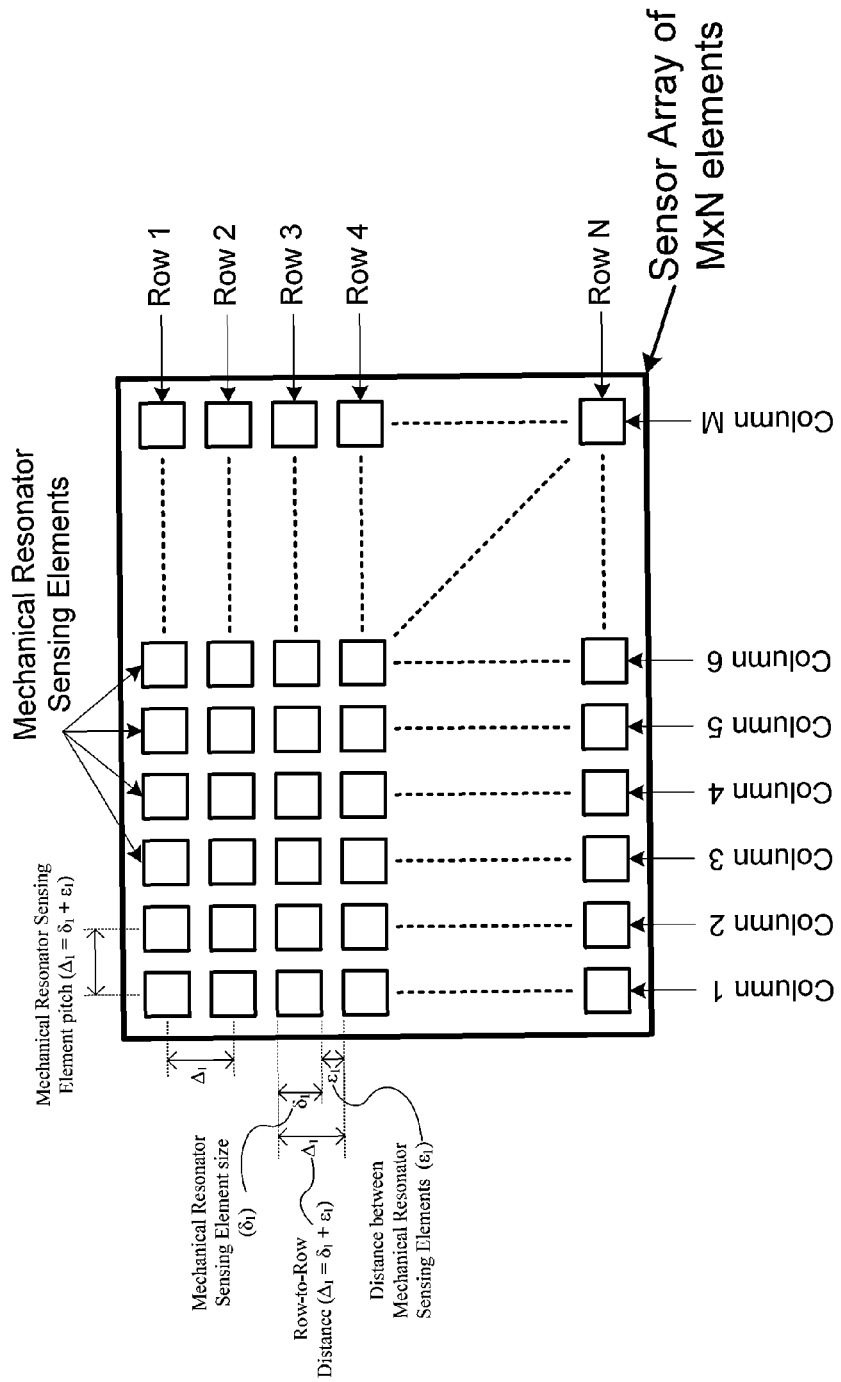
FIG. 40 is a diagram of a sensor array in accordance with the present invention.

A Fingerprint sensor using Acoustic Impediography is comprised of an Application Specific Integrated Circuit (ASIC or IC) and an array of mechanical resonator used as sensing elements. The array of sensing elements contains multiple sensing elements arranged in rows and columns as shown in FIG. 40.

Figure 41:
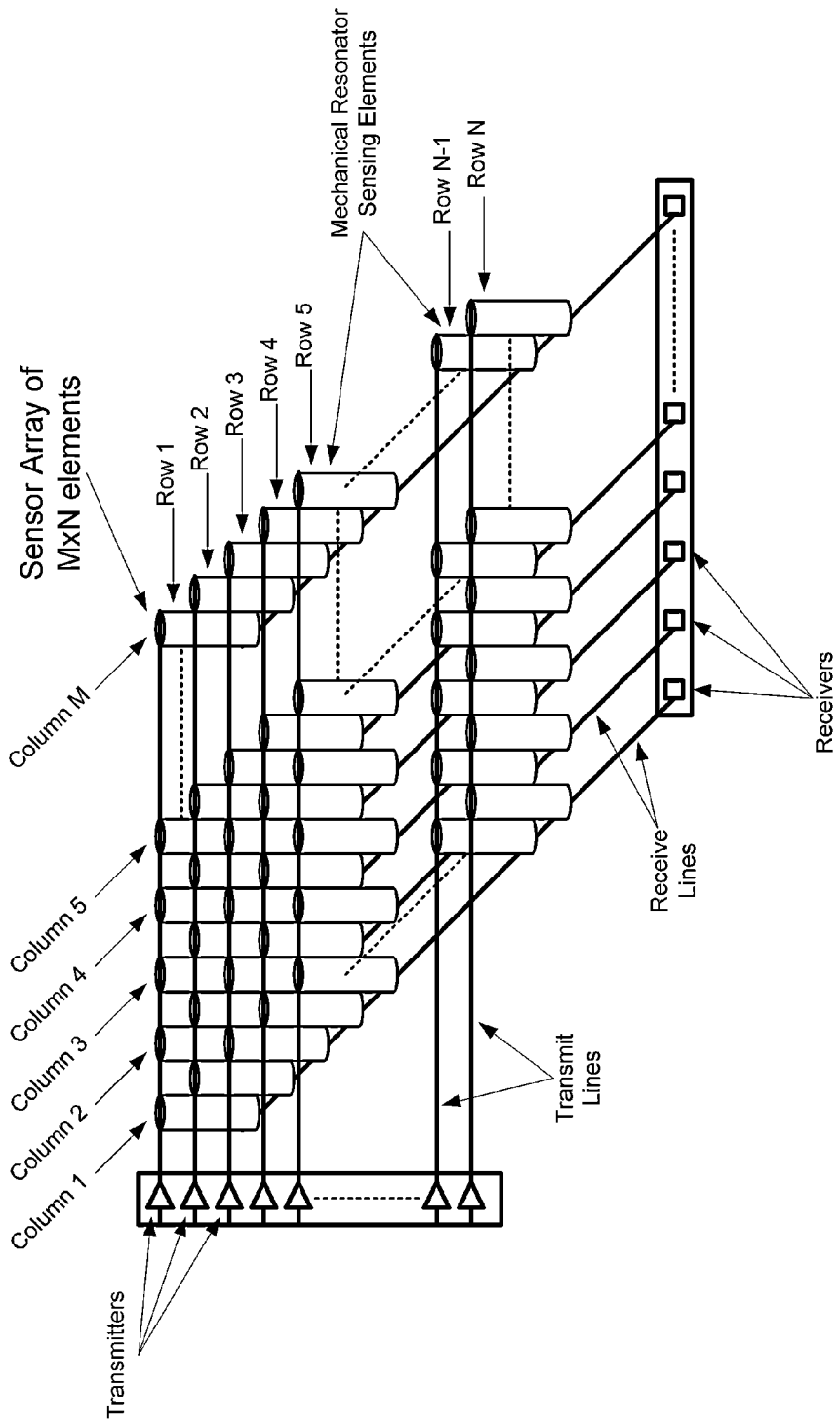
FIG. 41 is a Matrix of Mechanical Resonator Sensing Elements Interconnects to ASIC in accordance with the present invention.

Each sensing element is uniquely addressable by the Integrated Circuit using transmitters and receivers inside the IC. Each row of sensing elements is connected to a single transmitter inside the IC. In addition, each column of sensing elements is connected to a single receiver inside the IC as shown in FIG. 41.

Figure 42:
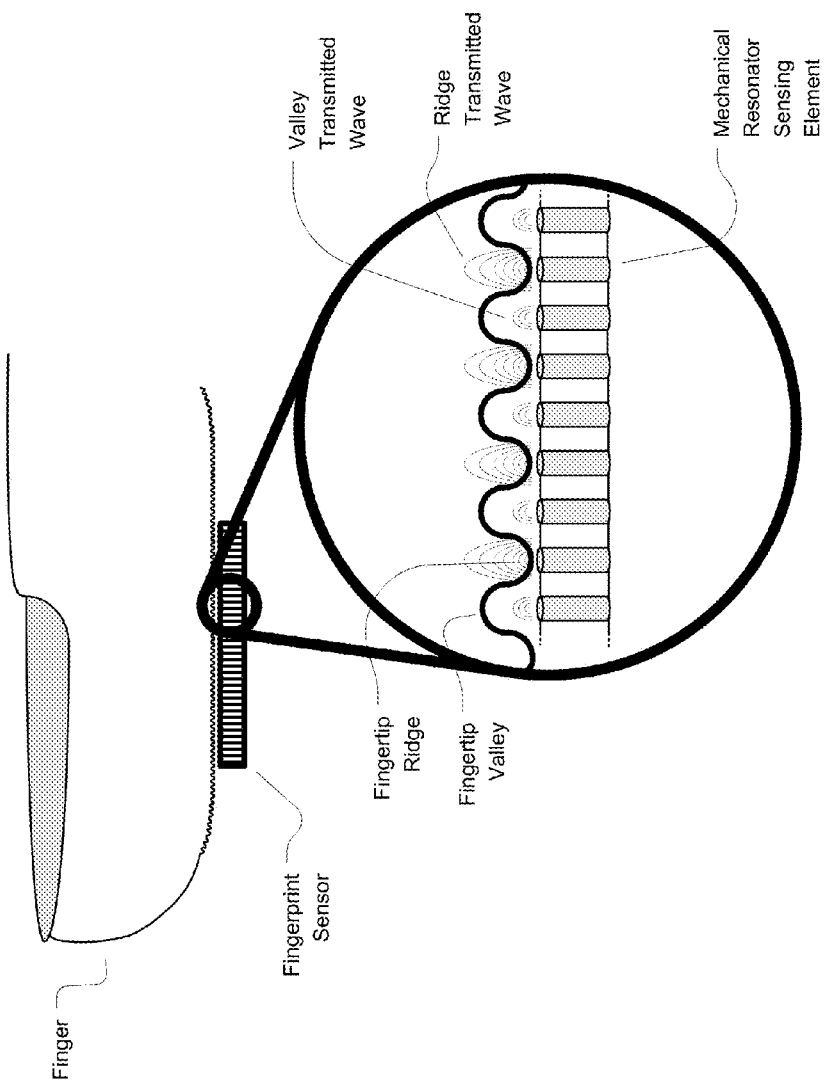
FIG. 42 is an illustration of a digit on an Acoustic Impedance digit Sensor.

The IC uses its integrated transmitters to generate an electrical signal that creates a mechanical oscillation of the sensing elements. This mechanical oscillation generates an acoustic wave above and below each sensing elements. Finger ridge and valleys will present different acoustic load (or impedance) on the individual sensing elements. Depending on this acoustic impedance of the finger ridge and valleys on the sensor, the acoustic wave generated by the sensing elements will be different as shown in FIG. 42.

Figure 43:
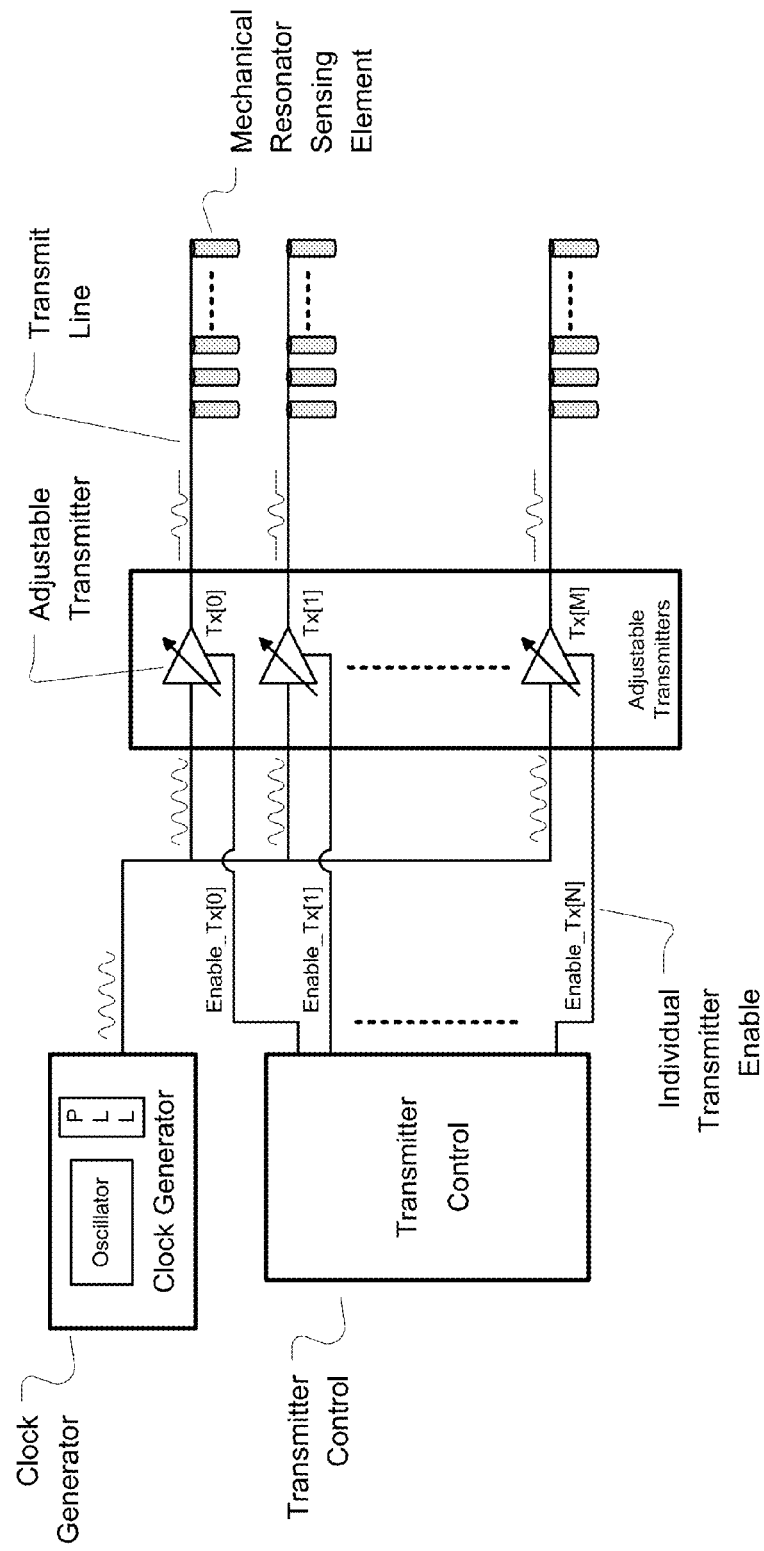
FIG. 43 is a block diagram illustration of ASIC Transmitters.

The ASIC has integrated transmitters connected to each row of the sensor array. Each transmitter is individually controlled by a "Transmitter Control" block. This control block determines the timing of each individual transmitter. It also controls the amplitude of the signal generated by each transmitter. It is advantageous for the transmitters to generate a sinusoidal shaped signal with a frequency matching the resonant frequency of the sensing elements. Either the series or the parallel resonance (or both) of the mechanical resonator sensing elements could be used. A programmable "Phased Lock Loop" (PLL) is used to generate the desired frequency generated the by transmitters as shown in FIG. 43.

The ASIC contains receivers connected to each column of the sensor array. When a single transmitter is enabled, a receiver is used to measure the amount of current flowing through a single sensing elements. Each receiver pipeline is comprised of the following elements:
  An input pin,
  A current-to-voltage converter/amplifier,
  A noise filter,
  Signal conditioning circuits,
  Adjustable gain and offset,
  Analog-to-Digital Converter.

Figure 44:
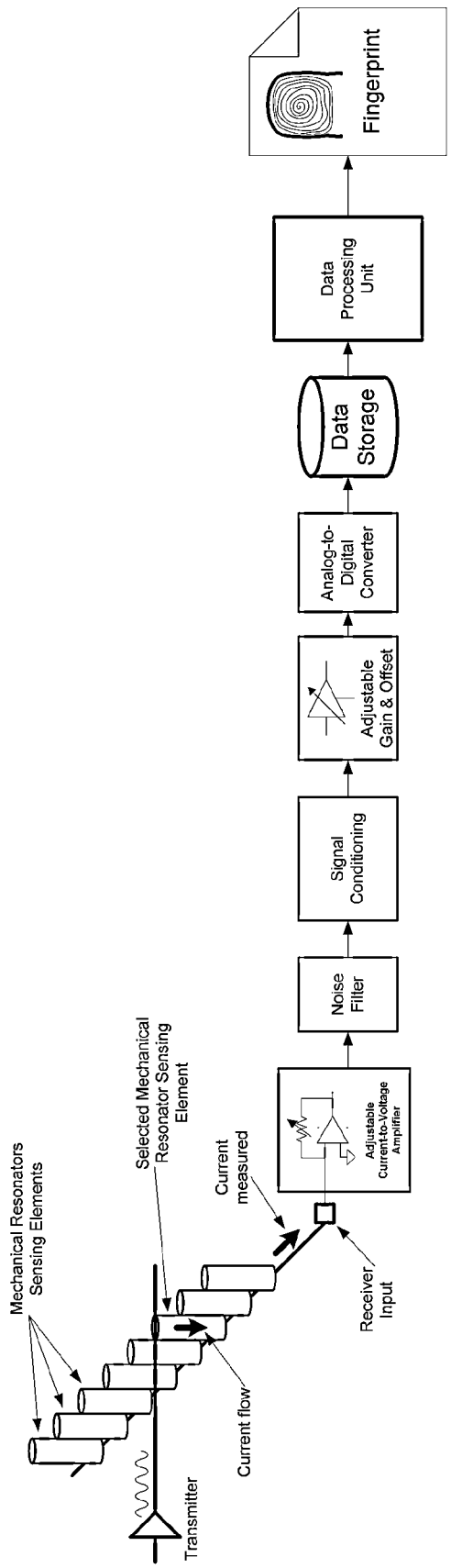
FIG. 44 is a block diagram illustration of an ASIC Receiver Pipeline.

Once the analog signal has been converted to a digital signal by the Analog-to-Digital Converter (ADC), it is stored into a data storage system to be processed and converted into a fingerprint image as shown in FIG. 44.

Figure 45:
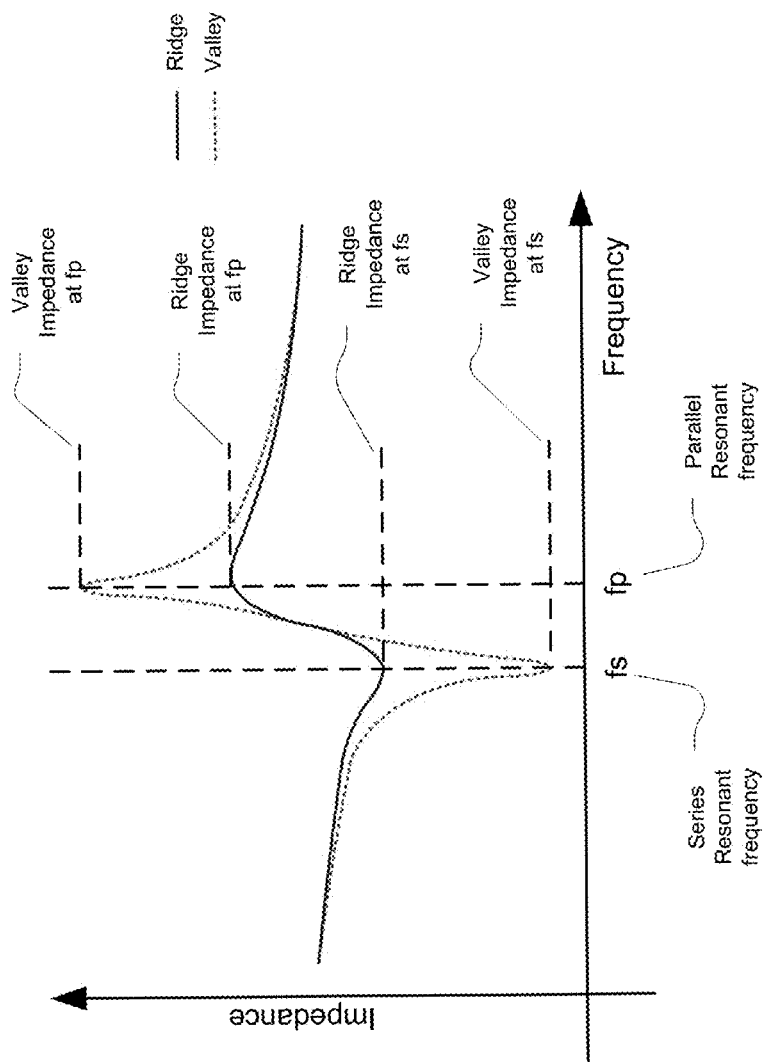
FIG. 45 is a graphical illustration of the performance of Impedance of Damped Mechanical Resonator Sensing Elements in accordance with the present invention.

The amount of current measured by the receiver is inversely proportional to the impedance of the individual sensing element. Which itself is proportional to the acoustic impedance of the ridge or valley on this sensing element. At the series resonant frequency the finger valley impedance is lower then the finger ridge impedance. And at the parallel resonant frequency, the finger ridge impedance is lower then the finger valley impedance as shown in FIG. 45.

Figure 46:
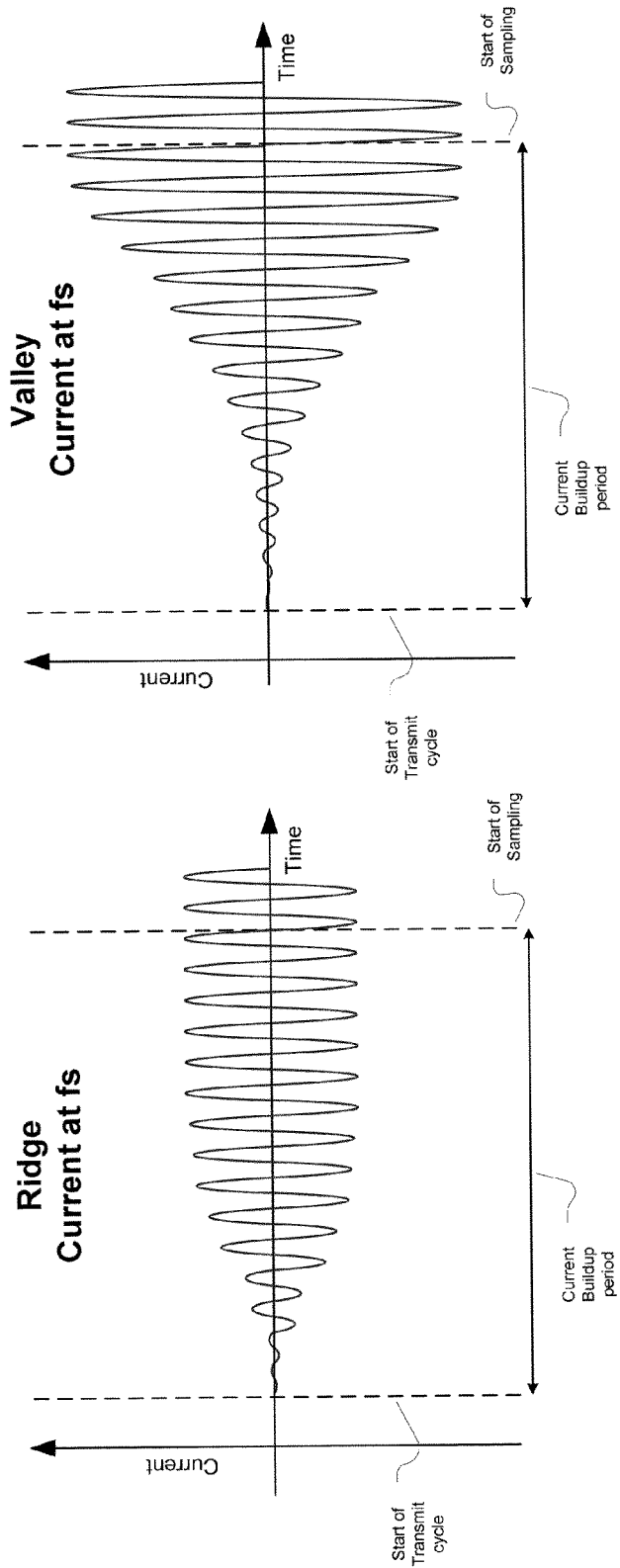
FIG. 46 is a graphical illustration of Current through Damped Mechanical Resonator Sensing Elements Current through Damped Mechanical Resonator Sensing Elements.

The current flowing through the sensing elements will buildup from the time the transmitter is enabled, until it reaches a steady state. This buildup time is due to the mechanical characteristics of the sensing elements. The impedance difference between ridge and valley will create different current amplitudes in the selected sensing elements as shown in FIG. 46.

Figure 47:
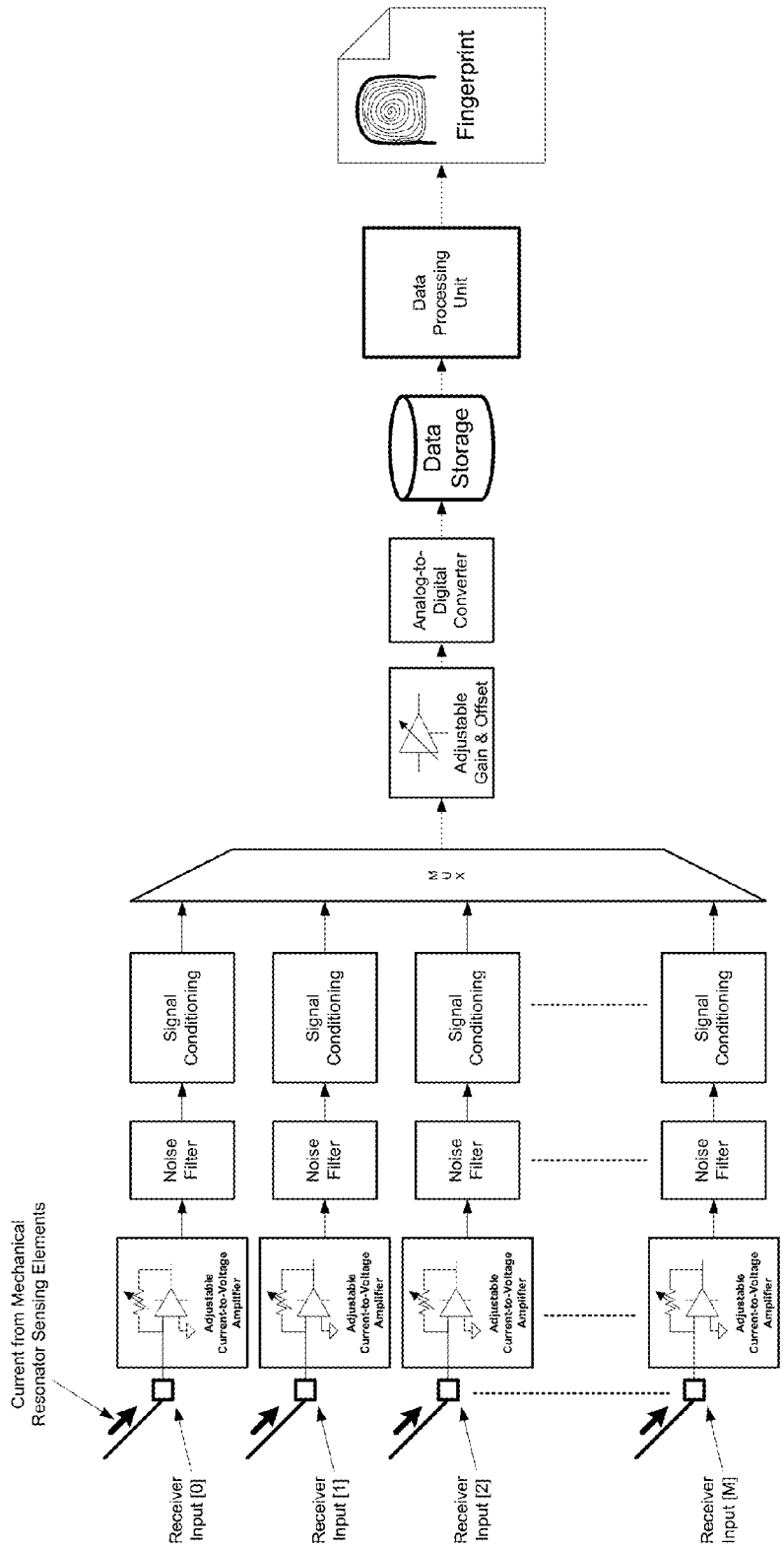
FIG. 47 is a block diagram illustration of an ASIC Receiver Pipeline Multiplexer.

Each component in a receiver pipeline could be shared with other receiver pipelines. The ability to share components reduces the amount of circuitry inside the ASIC. FIG. 47 shows an example where the "Adjustable Gain and Offset", and the "Analog-to-Digital Converter" are shared with other receivers. A multiplexer is used to switch the signals coming from each receiver feeding the "Adjustable Gain and Offset", and the "Analog-to-Digital Converter".

Figure 48:
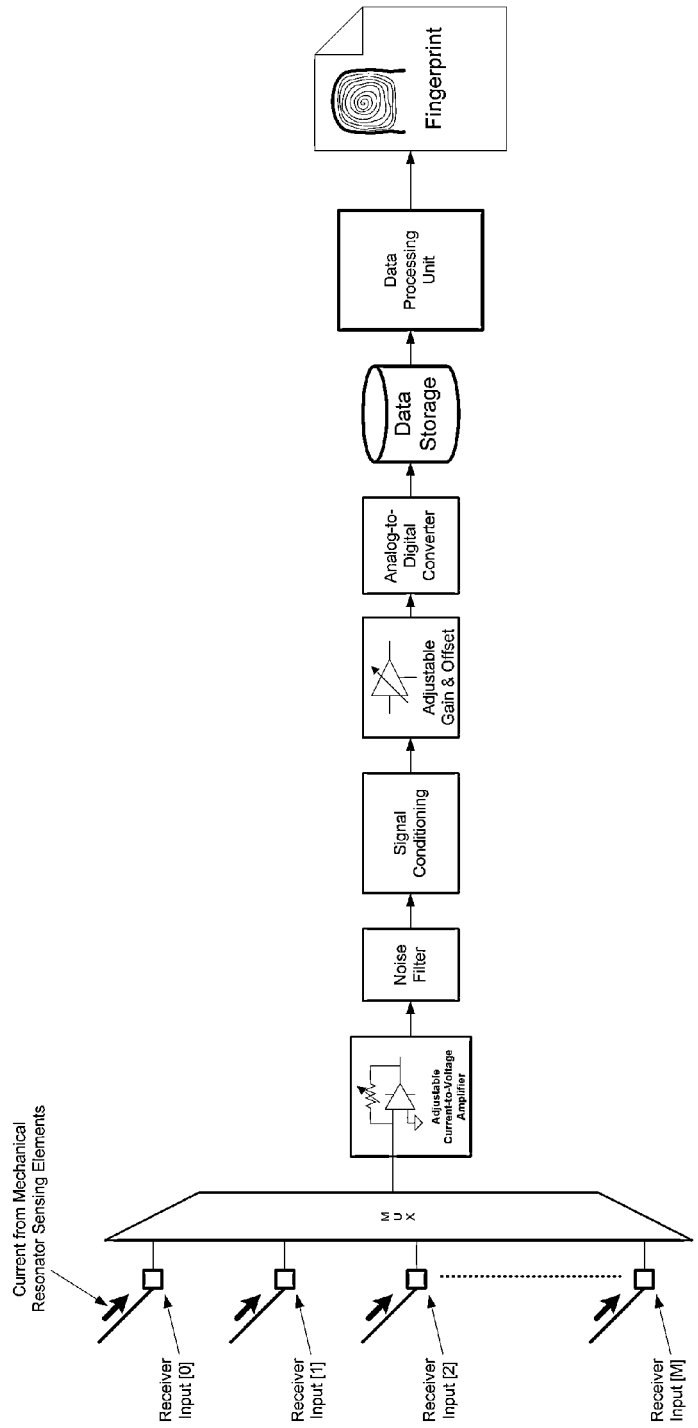
FIG. 48 is a block diagram illustration of an ASIC Receiver Pipeline Multiplexer Alternative Placement in accordance with the present invention.

The multiplexer placement in the pipeline can vary depending on the application and performance requirements. FIG. 48 shows an example where every component in the pipeline except for the input pin is shared between receivers.

Figure 49:
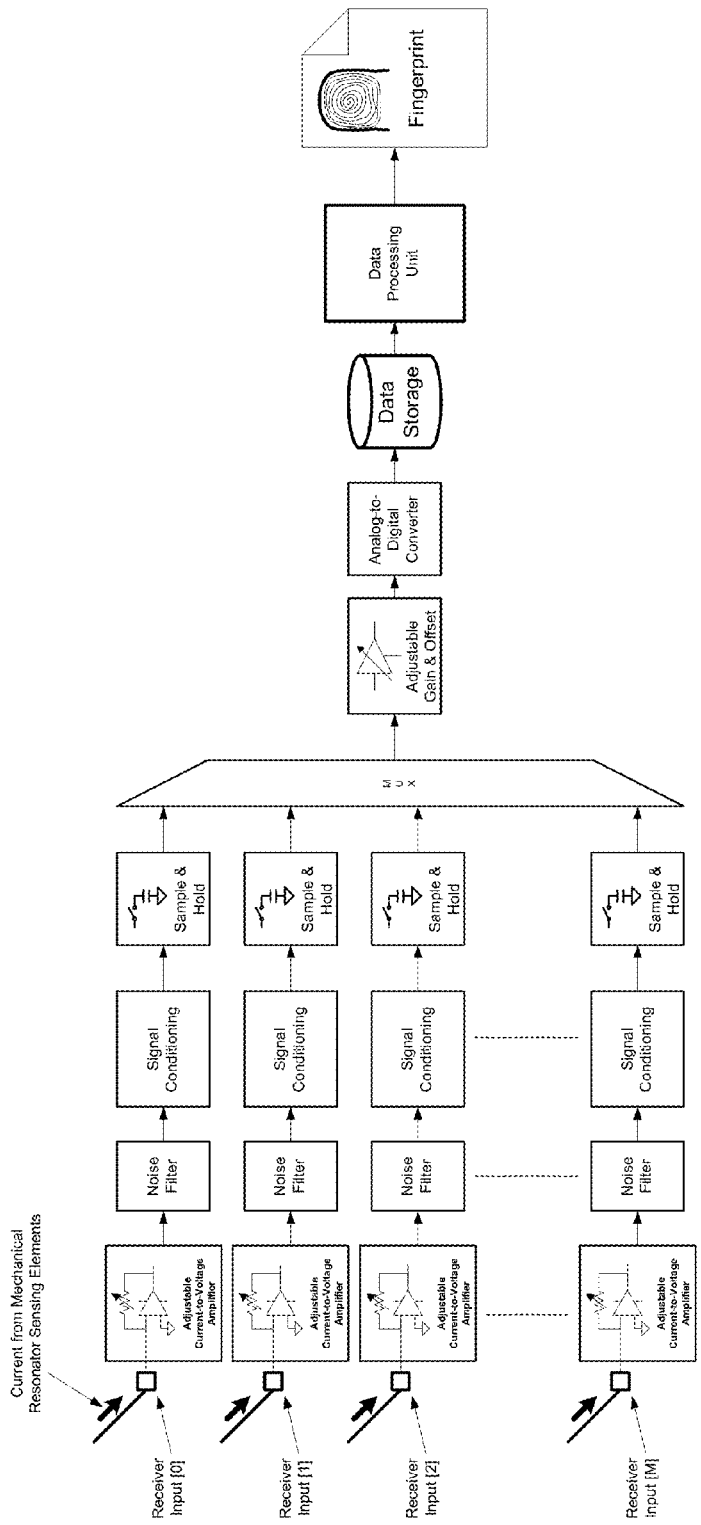
FIG. 49 is a block diagram illustration of an ASIC Receiver Pipeline with Sample-and-Hold for increased performance.

To improve performance sample and hold circuits can be used to break the pipeline into time slices. Different sections of the receiver pipeline can work on different sensing element data at different times. FIG. 49 shows an example where "Sample and Hold" circuits are inserted between the "Signal Conditioning" and "Adjustable Gain and Offset" blocks. Therefore, the section from the receiver input pin to the "Signal Conditioning" block are working on the next sensor element data, while the section from the "Adjustable Gain and Offset" to the "Analog-to-Digital Converter" are working on the current sensor element data.

Figure 50:
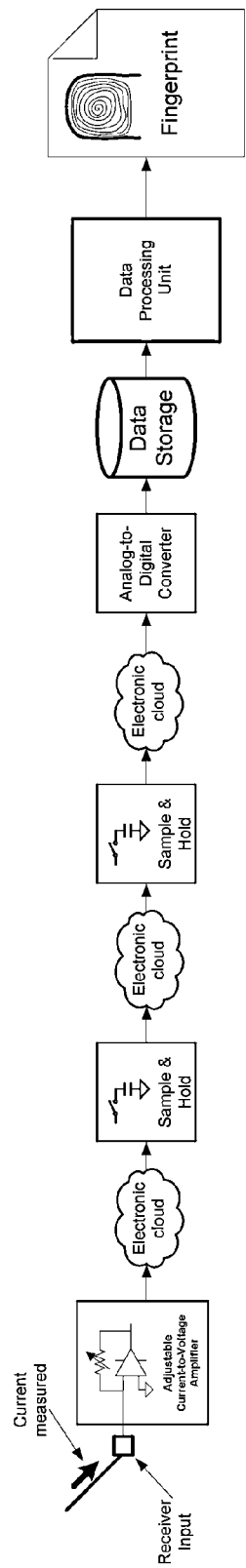
FIG. 50 is an illustration of ASIC Receiver Pipeline with Sample-And-Hold Generalized.

This concept of time slicing the receiver pipeline could be modified and expended as shown in FIG. 50, where multiple "Sample and Holds" are used along the pipeline. The "electronic cloud" represents any electrical component in the receiver pipeline.

Figure 51:
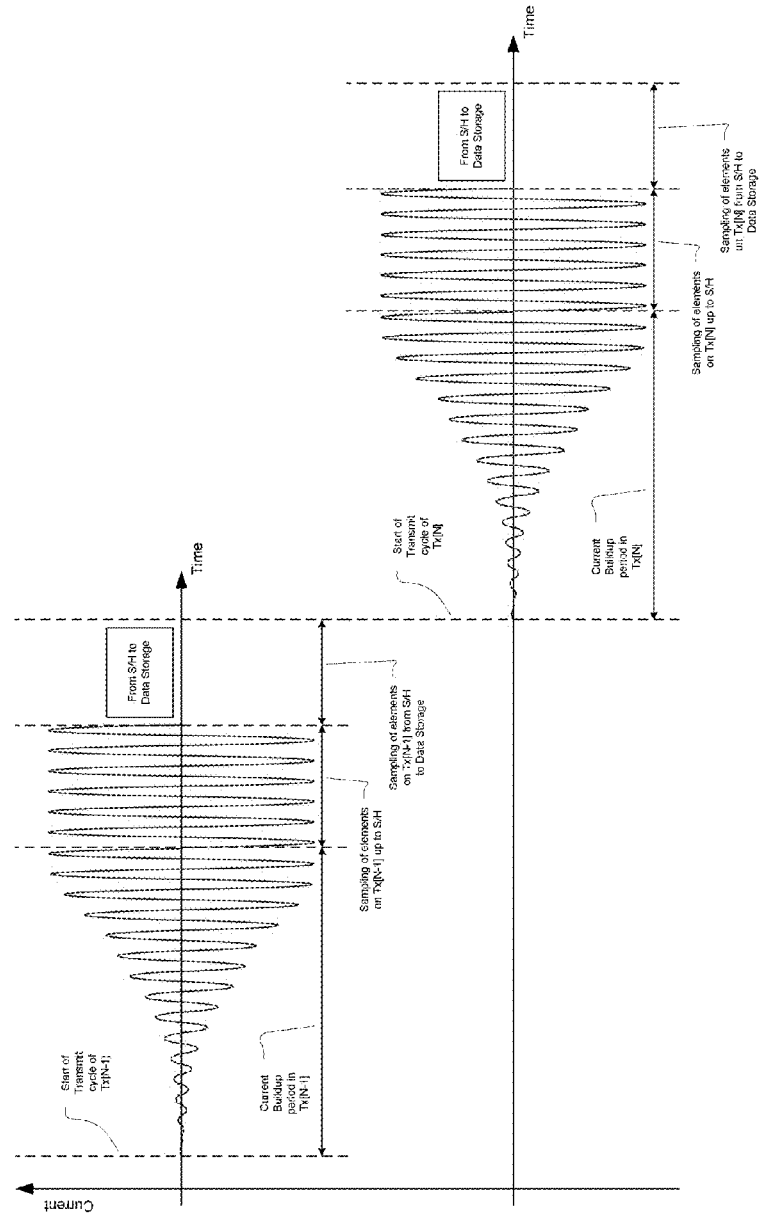
FIG. 51 is an illustration of Sampling of Sensing Elements on Tx[N−1] and Tx[N] without Sample & Hold in accordance with the present invention.

FIG. 51 shows the current from the sensing elements in the receiver pipeline over time without any "Sample and Hold".

Figure 52:
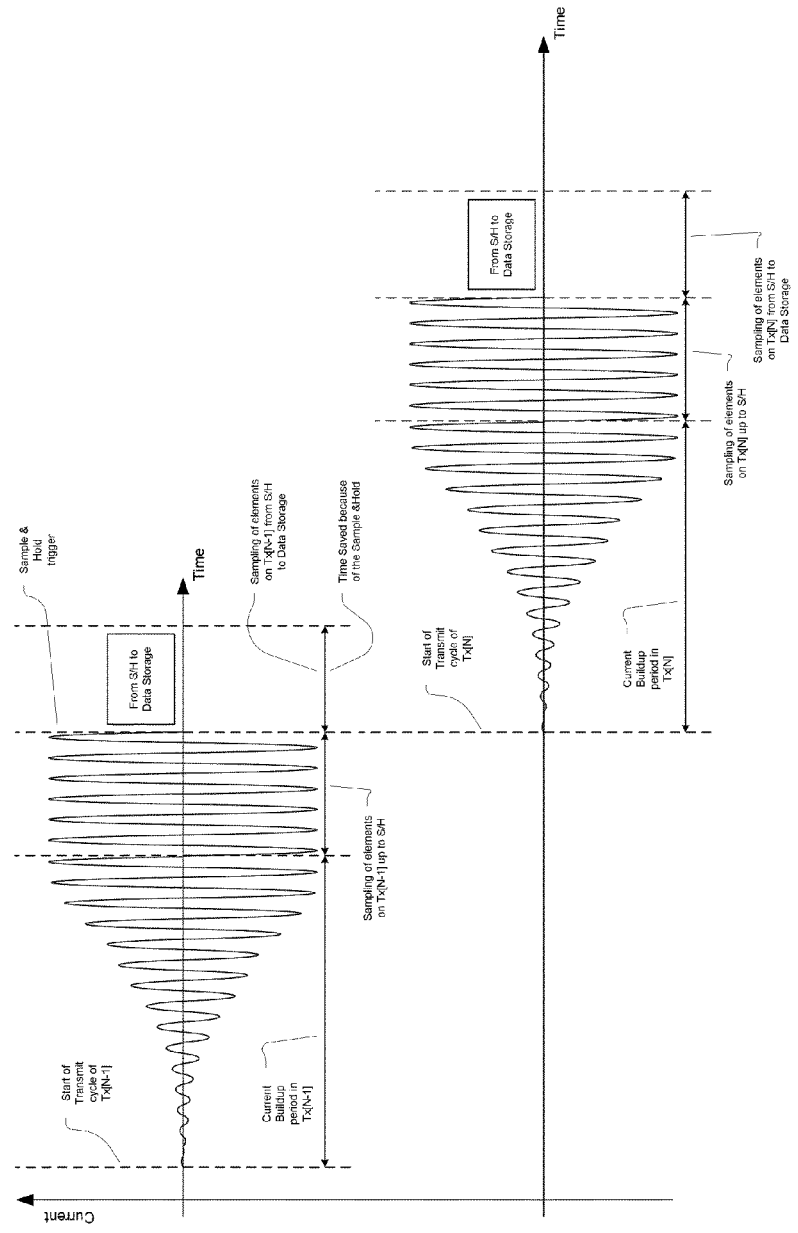
FIG. 52 is an illustration of Sampling of Sensing Elements on Tx[N−1] and Tx[N] with one set of Sample-And-Holds.

FIG. 52 shows the current from the sensing elements in the receiver pipeline over time with the same set of "Sample and Hold" as shown in FIG. 49. One can see the overlap in time between the two sets of data from two different sensing elements. The amount of overlap is proportional to the amount of time it takes to sample every sensing element in the sensor array. Which itself is proportional to the system performance.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A sensing device, comprising:
   an array of sensing elements, and
   wherein said sensing elements operate based upon acoustic impediography principles; and
   wherein said sensing device is configured to measure an acoustic impedance associated with at least one of said sensing elements, said acoustic impedance being measured in proportion to a measured electrical impedance of one or more electrical signals that are passed through said at least one of said sensing elements;
   a first electrical signal having a first frequency, is passed by said sensor device through said at least one of said sensing elements, said first frequency being equal to a serial resonant frequency of a circuit including said at least one of said sensing elements, and
   a second electrical signal having a second frequency, is passed by said sensor device through said at least one of said sensing elements, said second frequency being equal to a parallel resonant frequency of a circuit including said at least one of said sensing elements, and where
   said sensing device is configured to measure an amount of current of said first electrical signal to determine a first electrical impedance, and is configured to measure an amount of current of said second electrical signal second electrical signal to determine a second electrical impedance, and where
   a said first impedance is lower for a finger valley than a finger ridge, and where
   said second impedance is lower for a finger ridge than a finger valley,
   in order to determine an acoustical impedance, and to detect a presence of a finger valley or finger ridge in association with said at least one of said sensing elements.

2. The sensing device of claim 1, wherein the sensing elements are arranged in a two dimensional array of rows and columns.

3. The sensing device of claim 1 wherein the sensing device employs an Application Specific Integrated Circuit.

4. The sensing device of claim 2 wherein at least one transmitter transmits said electrical signal through at least one of said rows, and at least one receiver receives said electrical signal from at least one of said columns.

5. The sensing device of claim 4 wherein said at least one transmitter and said at least one receiver reside within one Application Specific Integrated Circuit.

6. The sensing device of claim 1, wherein a sample and hold circuit is employed to process data received from one or more sensing elements.

* * * * *